(12) United States Patent
Steeg

(10) Patent No.: US 6,493,637 B1
(45) Date of Patent: Dec. 10, 2002

(54) COINCIDENCE DETECTION METHOD, PRODUCTS AND APPARATUS

(75) Inventor: Evan W. Steeg, Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 09/404,714

(22) Filed: Sep. 24, 1999

Related U.S. Application Data

(63) Continuation of application No. PCT/CA98/00273, filed on Mar. 23, 1998, now abandoned.
(60) Provisional application No. 60/041,472, filed on Mar. 24, 1997.

(51) Int. Cl.[7] .............................................. G06F 17/30
(52) U.S. Cl. ........................................................ 702/19
(58) Field of Search ........................................... 702/19

(56) References Cited

FOREIGN PATENT DOCUMENTS

GB   2 283 840 A   5/1995

OTHER PUBLICATIONS

Conner et al. Proc. Natl. Acad. Sci. USA, 80, 278–282, Jan. 1983.*

Steeg et al., "Introduction of Specific Point Mutations into RNA Polymerase II by Gene Targeting in Mouse Embryonic Stem Cells: Evidence for a DNA Mismatch Repair Mechanism," *Proc. Natl. Acad. Sci. USA*, vol. 87, No. 12, National Academy of Sciences USA, Jun. 15, 1990, pp. 4680–4684.

R. Agrawal et al., "Fast Discovery of Association Rules," Chapter 12, *Advances in Knowledge Discovery and Data Mining*, pub. American Association for Artificial Intelligence, Menlo Park, California, ©1996, pp. 307–328.

D. Altschuh et al., "Correlation of Co–ordinated Amino Acid Substitutions with Function in Viruses Related to Tobacco Mosaic Virus," *J. Mol. Biol.*, vol. 193, 1987, pp. 693–707.

R. Bahadur, "A Representation of the Joint Distribution of Responses to n Dichotomous Items," Chapter 9, *Studies in Item Analysis*, ed. H. Solomon, Stanford University Press, 1962, pp. 158–175.

Carr et al., "Templates for Looking at Gene Expression Clustering," Statistical Computing & Statistical Graphics Newsletter, pp. 20–29 (Apr. 1997).

A.F.W. Coulson et al., "Protein and nucleic acid sequence database searching: a suitable case for parallel processing," *The Computer Journal*, vol. 30, No. 5, Oct. 1987, Cambridge, Great Britain, pp. 420–424.

U. Goebel et al., "Correlated Mutations and Residue Contacts in Proteins," *Proteins*, vol. 18, 1994, pp. 309–317.

(List continued on next page.)

*Primary Examiner*—Michael Borin
(74) *Attorney, Agent, or Firm*—Robert H. Wilkes; Carol Miernicki Steeg; Sterne, Kessler, Goldstein & Fox PLLC

(57) ABSTRACT

A method and system for detecting coincidences in a data set of objects, where each object has a number of attributes. Iteratively, equally-sized subsets of the data set of sampled, and coincidences (co-occurrences of a plurality of attribute values in one or more objects in the subset) are recorded. For each coincidence of interest, the expected coincidence count is determined and compared with the observed coincidence count; this comparison is used to determine a measure of correlation for the plurality of attributes for the coincidence. The resulting set of k-tuples of correlated attributes is reported, a k-tuple of correlated attributes being a plurality of attributes for which the measure of correlation is above a predetermined threshold. The method and system (implemented on an array of processing nodes) is suitable for protein structure analysis, e.g. in HIV research.

39 Claims, 18 Drawing Sheets

OTHER PUBLICATIONS

R. Guigó et al., "Inferring Correlation between Database Queries: Analysis of Protein Sequence Patterns," *IEEE Transactions on Pattern Analysis and Machine Intelligence,* vol. 15, No. 10, Oct. 1993, New York, New York, USA, pp. 1030–1041.

D. Heckerman, "Bayesian Networks for Knowledge Discovery," *Advances in Knowledge Discovery and Data Mining,* Chapter 11, pub. American Association for Artificial Intelligence, Menlo Park, California, ©1996, pp. 273–306.

W. Hoeffding, "Probability Inequalities for Sums of Bounded Random Variables," *Journal of the American Statistical Association,* vol. 58, No. 301, Mar. 1963, pp. 13–30.

Klingler, T. et al., "Discovering Structural Correlations in α–Helices," *Protein Science,* vol. 3, 1994, pp. 1847–1857.

B. Korber et al., "Covariation of Mutations in the V3 Loop of Human Immunodeficiency Virus Type 1 Envelope Protein: an Information Theoretic Analysis," *Proc. Natl. Acad. Sci. USA,* vol. 90, Aug. 1993, pp. 7176–7180.

A. Krogh et al., "Hidden Markov Models in Computational Biology: Applications to Protein Modeling," *J. Mol. Biol.,* vol. 235, 1994, pp. 1501–1531.

A.S. Lapedes et al., "Use of Adaptive Networks to Define Highly Predictable Protein Secondary–Structure Classes," *Machine Learning,* vol. 21, No. 1 / 2, Oct.–Nov. 1995, Boston, Massachusetts, USA, pp. 103–124.

C. de Marcken, "Unsupervised Language Acquisition," Ph.D. Thesis, M.I.T. (Sep. 1996) (title page, abstract, and pp. 82–93).

P. Michaud, "Clustering Techniques," *Future Generation Computer Systems,* vol. 13, Nov. 1997, NL, pp. 135–147.

R. Paturi et al., "The Light Bulb Problem," *Information and Computation,* vol. 117, No. 2, Mar. 1995, pp. 187–192.

Steeg, E. et al., "The Efficient Determination of Higher–Order Features in Protein Sequence Data" (Working Paper), Aug. 27, 1993, pp. 1–18. (FIGs. lost).

Steeg, E. et al., "Application of a Noval and Fast Information–Theoretic Method to the Discovery of Higher–Order Correlations in Protein Databases" in Proceedings of the 1998 Pacific Symposium on Biocomuting. Ed. Altman et al., World Scienctific Publishing Co., New Jersey, pp. 573–584 (Jan. 4–9, 1998).

J. Williams et al., "A Process for Detecting Correlations between Dichotomous Variables," B. Kleinmutz, ed., *Clinical Information Processing by Computer,* Holt, Rinehart and Winston, New York, 1969, pp. 100–128.

* cited by examiner

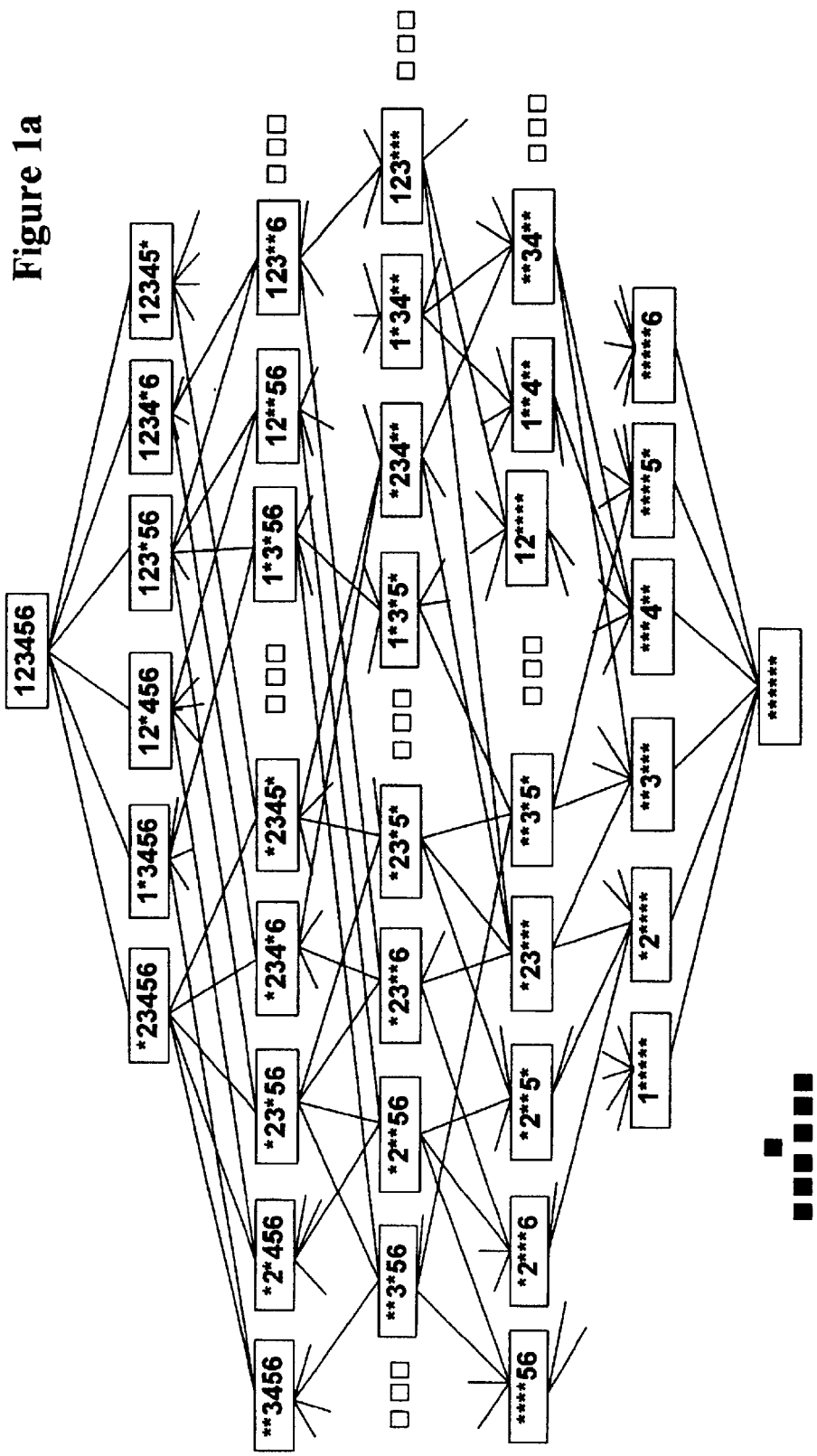

|   |   |   |   |   |   |
|---|---|---|---|---|---|
| ① | A | B | C | D | E | F |
| 2 | W | U | C | V | E | G |
| 3 | Z | L | C | M | W | M |
| 4 | V | U | C | V | A | G |
| ⑤ | A | B | C | D | Z | Z |
| ⑥ | W | L | C | M | E | Z |

```
         1  A  B  C  D  E  F
rows     5  A  B  C  D  Z  Z
         6  W  L  C  M  E  Z
    1 5 6
```

| | |
|---|---|
| 0 0 1 | W@c1, L@c2, M@c4 |
| 0 1 0 | Z@c5 |
| 0 1 1 | Z@c6 |
| 1 0 0 | F@c6 |
| 1 0 1 | E@c5 |
| 1 1 0 | A@c1, B@c2, D@c4 ← |
| 1 1 1 | C@c3 |

|   |   |   |   |   |   |
|---|---|---|---|---|---|
| 1 | A | B | C | D | E | F |
| ② | W | U | C | V | E | G |
| 3 | Z | L | C | M | W | M |
| ④ | V | U | C | V | A | G |
| 5 | A | B | C | D | Z | Z |
| ⑥ | W | L | C | M | E | Z |

```
         2  W  U  C  V  E  G
rows     4  V  U  C  V  A  G
         6  W  L  C  M  E  Z
    2 4 6
```

| | |
|---|---|
| 0 0 1 | L@c2, M@c4, Z@c6 |
| 0 1 0 | V@c1, A@c5 |
| 1 0 1 | W@c1, E@c5 ← |
| 1 1 0 | U@c2, V@c4, G@c6 ← |
| 1 1 1 | C@c3 |

|   |   |   |   |   |   |
|---|---|---|---|---|---|
| ① | A | B | C | D | E | F |
| 2 | W | U | C | V | E | G |
| ③ | Z | L | C | M | W | M |
| 4 | V | U | C | V | A | G |
| 5 | A | B | C | D | Z | Z |
| ⑥ | W | L | C | M | E | Z |

```
         1  A  B  C  D  E  F
rows     3  Z  L  C  M  W  M
         6  W  L  C  M  E  Z
    1 3 6
```

| | |
|---|---|
| 0 0 1 | W@c1, Z@c6 |
| 0 1 0 | Z@c1, W@c5, M@c6 |
| 0 1 1 | L@c2, M@c4 ← |
| 1 0 0 | A@c1, B@c2, D@c4, F@c6 |
| 1 0 1 | E@c5 |
| 1 1 1 | C@c3 |

| Residue | 1 | 2 | ... | i | ... | j | ... | |
|---|---|---|---|---|---|---|---|---|
| Sequence | | | | | | | | |
| 1 | I | L | | W | | G | | |
| 2 | S | C | | G | | W | | |
| 3 | L | C | ... | Y | ... | A | ... | Aligned |
| 4 | A | P | | W | | G | | Family of |
| 5 | S | A | | Y | | A | | Homologous |
| 6 | R | R | | G | | Y | | Sequences |
| . | . | . | | . | | . | | |
| . | . | . | | . | | . | | |
| . | . | . | | . | | . | | |
| M-1 | C | P | | W | | G | | |
| M | L | I | ... | A | ... | Y | ... | |

Large      Small
                        Side-Chain ⇒ Side-Chain

Small      Large
                        Side-Chain ⇒ Side-Chain

Figure 15a

COINCIDENCE DETECTION METHOD, PRODUCTS AND APPARATUS

This is a continuation of International Application PCT/CA98/00273, with an international filing date of Mar. 23, 1998, now abandoned, which claims benefits of the filing date of U.S. Provisional application 60/041472, filed Mar. 24, 1997.

TECHNICAL FIELD

The invention relates to methods, devices and systems for coincidence detection among a multitude of variables. In addition, the invention relates to applying coincidence detection methods to various fields, and to products derived from such application.

BACKGROUND ART k-tuples of Correlated Attributes

The discovery of correlations among pairs of k-tuples of variables has applications in many areas of science, medicine, industry and commerce. For example, it is of great interest to physicians and public health professionals to know which lifestyle, dietary, and environmental factors correlate with each other and with particular diseases in a database of patient histories. It is potentially profitable for a trader in stocks or commodities to discover a set of financial instruments whose prices covary over time. Sales staff in a supermarket chain or mail-order distributor would be interested in knowing that consumers who buy product A also tend to buy products B and C, and this can be discovered in a database of sales records. Computational molecular biologists and drug discovery researchers would like to infer aspects of 3D molecular structure from correlations between distant sequence elements in aligned sets of RNA or protein sequences.

One formulation of the general problem which encompasses many diverse applications, and which facilitates understanding of the principles described herein is a matrix of discrete features in which rows correspond to "objects" (such as individual patients, stock prices, consumers, or protein sequences) and the columns correspond to features, or attributes, or variables (such as lifestyle factors, stocks, sales items, or amino acid residue positions).

Mathematical methods for determining a measure of the type, degree, and statistical significance of correlation between any two, or even three or four, particular variables are widespread and well-understood. These methods include linear and nonlinear regression for continuous variables and contingency table analysis techniques for discrete variables. However, great difficulties arise when one tries to estimate correlation—or just estimate joint or conditional probabilities—over much larger sets of variables. This intractability has one main cause—there are too many joint attribute-value probability density terms—and this manifests itself in two serious problems: (1) computing and storing frequency counts over all terms, over the database, requires too much computation and memory; (2) there is usually an insufficient number of database records to support reliable probability estimates based on those frequency counts.

Let us consider some details. For M records (objects), N variables (attributes, fields), and supposing that each variable has the same set of $|A|$ possible values, there are $$\binom{N}{k} = \frac{N!}{(N-k)!k!}$$

k-tuples of columns. Adding the number of k-tuples for each $k=1, 2, \ldots, N_A$ results in $2^N-1$ such tuples of all sizes. This exponential complexity has been a major obstacle standing in the way of higher-order probability estimation and correlation detection methodologies.

One natural way to think about this complexity is in terms of the power set of the set of column variables. This power set forms a mathematical lattice under the operation $\subset$, a "tower" corresponding to a graph whose nodes are subsets of this set of column variables. (Note that if a set has N members, the power set has $2^N$ members). From this viewpoint, two nodes representing subsets $\sigma_1$ and $\sigma_2$ are connected if and only if either $\sigma_1 \subset \sigma_2$ or $\sigma_2 \subset \sigma_1$. We say that $\sigma_2$'s node is above $\sigma_1$'s if $\sigma_1 \subset \sigma_2$. This gives a natural meaning to the term "higher-order", as appearing higher up the tower. We call the bottom, the null set node, the 0th tier; the single column terms from the first tier, and so on.

Continuing with the tower analogy, we note that each "floor" of this edifice contains $$\binom{N}{k}$$

"suites", and each suite contains $|A|^k$ "rooms". In other words, the kth level of the lattice corresponds to $$\binom{N}{k}$$

different k-tuples of column variables, and associated with each k-tuple is an ($|A|$ by $|A|$ ... by $|A|$) contingency table, each cell of which must store the counted frequency of a particular joint symbol $(a_{j1}, a_{j2}, \ldots, a_{jk})$ were one to use a classical contingency table test for the correlation between those particular k columns. (See FIG. 1a).

For any $k \in \{1, 2, \ldots, N\}$, for any particular k-tuple of columns $(c_{j1}, c_{j2}, \ldots, c_{jk})$, there are $|A|^k$ possible joint values. For any $k \in \{1, 2, \ldots, N\}$, for any particular k-tuple of columns $(c_{j1}, c_{j2}, \ldots, c_{jk})$, the estimation of Kullback divergence or other correlation function using the dataset is at least an $\Omega(Mk)$ or $\Omega(|A|^k)$ computation, depending upon the relative sizes of M, k and $|A|$.

A comprehensive probabilistic model of the database must be able to specify probability estimates for $$\sum_{k=1}^{N} \binom{N}{k}|A|^k$$

terms. This means, for example in the computational molecular biology domain, that for a tiny heptapeptide sequence family, each sequence having a length of seven amino acid residues, there are 1,801,088,540 terms to specify. For an unrealistically small RNA of fifteen nucleotides in length, over the smaller RNA alphabet of four base symbols, there are 30,517,578,124 terms.

Clearly the models can become intractably huge. What about the space of possible models through which a modelling/learning procedure must search? Consider a latent-variable model, which seeks to explain correlations between sets of observable variables by positing latent variables whose states influence the observables jointly.

Since each model must specify a set of k-tuples of variables, and there are $\exp(2, 2^N)$ (i.e., 2 to the power $2^N$) such sets, there are $\exp(2, 2^N)$ possible models in the worst-case search space.

Various methods for determining a measure of higher-order probabilities will circumvent the combinatorial explosion through severe prior restrictions on the width k (See FIG. 3a), the locality (FIG. 2a), the number, or the degrees of correlation of the higher-order features sought, and on the kinds of models entertained (See FIG. 4a).

Three Goals of Probability Estimation

It is useful, before discussing details of existing methods and of the current invention, to delineate three different possible goals of probability estimation in large datasets, each corresponding to a large body of research and current practice:

1. Estimation of the fully-specified, fully higher-order joint probability distribution: Estimate a probability density q that specifies $$q(a_{i1}@c_{i1}, a_{i2}@c_{i2}, \ldots, a_{ik}@c_{ik})$$

for all k-tuples of attributes and possible values.

2. Hypothesis testing, for particular hypotheses concerning particular attributes and particular variables: For example, are the data consistent with the hypothesis that columns $c_{i1}, c_{i2}, \ldots, c_{ik}$ are independent?

3. Feature detection, or "data mining": Detect the most suspicious coincidences, for example, joint attribute occurrences that are more probable than would be predicted from lower-order marginals. Related to this, find the most highly correlated k-tuples of columns.

It is the feature detection and data mining applications that are most relevant to the present invention. However, some of the most successful ways to estimate a full higher-order joint probability distribution of a database require the specification of exactly those higher-order terms which represent high correlations among sets of $k \geq 2$ variables and invoking maximum entropy assumptions, and therefore the current invention is aimed at those applications as well.

Related Work

Various mathematical and computational methods have been proposed and used to estimate higher-order probabilities, to detect correlations, and to model higher-order database relationships. All such prior methods either perform a global, sometimes exhaustive search through all possible k-tuples of variables, which is too costly, or they avoid the complexity altogether by limiting their search to only k-tuples of a specific fixed, small size k. (Often, k=2 so only pairwise correlations are ever considered).

Below are listed some representative examples of related work.

Assuming Independence between Attributes. The easiest way to avoid the complexity of higher-order correlations is just to pretend that they do not exist. Many of the algorithms and computer programs, historically dominant in some fields of application of the current method, simply construct and use a model of the data in which all variables, all attributes, are independent. For example, the modelling of DNA and protein sequences, in computational molecular biology, is often done with consensus sequences and profiles, which assume incorrectly that the different base or amino acid residue positions are independent. Reliance on such models can obscure crucial functional and structural insights into the DNA or proteins being modelled.

Prior Limits on k. One proposal for Gibbs models of databases is based on the use of Gibbs potentials, and it proposes a hashing method for calculating these special terms. Each kth-order potential requires an estimation of a kth-order joint probability density as well as some number of lower-order (typically k-/th-order) densities. The asymptotic time complexity of Miller's pattern-collection subroutine, the major component of the potential calculation, is, when interpreted in our terminology:

$$M \cdot \sum_{k=1}^{K} N_A 2^k \approx O(MN^K)$$

where $K=k_{max}$ is the highest order of features for which one will search and by which one will represent database objects. This exponential blow-up prevents one from searching for higher-order features (HOFs) of any order k much higher than 4 or 5 in databases with hundreds of attributes.

Many methods, in different application areas, simply limit k to k=2. For example, pairwise inter-residue correlation methods discover second-order features that can be useful in the prediction of protein structure and function and that can be built into classifiers more sensitive that first-order sequence classifiers and fold-recognizers. To the extent that k-ary interactions are important, and to the extent that such interactions leave traces in sets of homologous sequences, the pairwise methods are deficient. One can try to infer k-ary correlations from sets of 2-ary correlations [9] (essentially by computing the transitive closure of the "CorrelatesWith" binary relation), but this heuristic can lead to trouble: high pairwise correlations among variables x, y, z do not in general imply, nor are they necessarily implied by, a high 3-ary correlation (as measured by Kullback divergence) of the three variables x, y, z. In other application areas, such as the study of multiple drug interactions, it is similarly true that important higher-order relationships can be missed by pairwise correlation detection methods.

The Paturi et al. Method for Identifying the Most Correlation Pair of Random Variables. A method has been reported for the problem of finding the most highly correlated pair $X_i$, $X_j$ of variables from among a large set of N random binary variables $X_1, X_2, \ldots, X_N$. The method is easily extended to finding the most correlated k-tuple of random binary variables, but at a significant increase in computational complexity, and only for $k \geq 2$ fixed a priori. It uses a definition of correlation that has Correlation $(X_i, X_j) = P[X_i = X_j]$ over some sets of M samples $\{X^m_1, X^m_2, \ldots, X^m_N\}_{m=1,2,\ldots,M}$. (Here $P[X_i = X_j]$ means "the probability that variable $X_i$ has the same value, or state, as variable $X_j$). Much of the computational complexity, both time complexity and sample complexity, of their method can be incurred in trying to separate two or more nearly equally-correlated pairs (or k-tuples) of variables.

The two variants of the Paturi method are asymptotically quadratic and subquadratic in N, respectively, the faster procedure requiring more sampling. When the method is extended to search for the biggest k-ary correlation, where correlation is now defined as $P[X_{i1} = X_{i2} = \ldots = X_{ik}]$, the time complexity grows to approximately $O(k^2 N^k \log^3 N)$. Search for highly correlated attribute cliques of width k much greater than 5 or 6 in very large datasets is once again ruled out.

Hidden Markov Models. Hidden Markov Models (HMMs) have been used widely and with increasing success in recent years, in both automatic speech recognition and in the modelling of protein, DNA, and RNA sequences.

Although some groups have reported significant success in modelling protein sequence families and continuous speech data with HMMs, nonetheless there are great improvements to be made in learning time and model robustness by the "hardwiring" of pre-selected higher-order features into HMMs. (This has been investigated for HMM-like recurrent neural networks, in different domains).

Some of the same reasons why HMMs are very good at aligning the protein sequences or recorded utterances in the first place, using local sequential correlations, make such methods less useful for finding the important sequence-distant correlations in data that has already been partially or completely aligned. The phenomenon responsible for this dilemma is termed "diffusion".

A first-order HMM, by definition, assumes independence among sequence columns, given a hidden state sequence. Multiple alternative state sequences can in principle be used to capture longer-range interactions, but the number of these grows exponentially with the number of k-tuples of correlated columns.

The Agrawal et al. Method for Discovery of Association Rules. This method was developed in perhaps the purest data mining context, the automatic extraction of knowledge-base rules from databases. It considers a database of M transactions (objects, rows) and N items (attributes, columns) and seeks to extract rules of the form a=>b. It therefore seek pairs of attributes a, b such that "transactions that contain a tend to contain b", hence those pairs with high values for p(b|a). "People who buy CD players tend to buy CDs", is just one example suggesting the potential commercial interests in such methods. (More generally, one can search for sets of attributes with high $p(b_1, b_2, \ldots, b_k | a_1, a_2, \ldots, a_j)$).

A rule a=>b is said to have:

1. confidence c if c % of transactions containing a also contain b (hence, roughly, if $$\left(\frac{p(a,b)}{p(a)}\right) \geq \frac{c}{(100)});$$

2. support s if s % of transactions contain a and b (hence, roughly, if $$p(a,b) \geq \frac{s}{100}).$$

The goals behind this method are different from the objectives of the current invention. However, the different objectives are brought closer together if one focuses on the Agrawal method's discovery of symmetric rules (so that the search is for attribute pairs displaying high values for both $$\frac{p(a,b)}{a} \text{ and } \frac{p(a,b)}{b}),$$

and if one reduces the emphasis on support (so that coincidences that are suspicious, even if occurring rarely, are sought).

The Agrawal method is shown to have $O(\|S\| \cdot MN)$ time complexity, where $\|S\|$ is the sum of all values Support ($\alpha$) for an exponentially large number of k-tuples $\alpha$ of attributes, of any size $1 \leq k \leq N$, that reach a particular stage of processing in this procedure. Hence the method is $O(2^N)$ in the worst case. A series of empirical tests are performed on what they considered to be realistic datasets for their domain. The running time of the procedure grew only linearly with the number M of transactions, but the number of items, or attributes, was held constant at $N_A=1000$, and their constructed datasets probably contained no correlated k-tuples of width k>10. An analysis of their algorithm, which is based on an incremental build-up of kth-order cliques from k-/th-order cliques, makes clear that the method takes much more computation to find wide HOFs (large k) than narrower HOFs (lower k) of equivalent statistical significance.

Steeg, Robinson, Deerfield, Lappa—1993. Some rough, heuristic methods have been presented for finding k-tuples of correlated residues (positions) in sets of aligned protein sequences. One of the presented methods employed one embodiment of a rudimentary version of the representation and detecting coincidences steps of the described herein.

Alternative methods of, and devices for, finding correlations between attributes, and applications for those correlations, are required.

DISCLOSURE OF THE INVENTION

In a first aspect the present invention provides a coincidence detection method for use with a data set of objects having a number of attributes. The base method includes the following steps:

representing a set of M objects in terms of a number $N_A$ of variables ("attributes"), where an attribute is said to occur in an object if the object possesses the attribute;

sampling a subset of $r_i$ out of the M objects, for each iteration among a predetermined number of iterations;

detecting and recording coincidences among sets of k of the attributes in each sampled subset of objects, a coincidence being the co-occurrence of $1 \leq k \leq N_A$ attributes in the same $h_i$ out of $r_i$ objects in the sampled subset, where $0 \leq h_i \leq r_i$;

determining an expected count of coincidences for any set of k attributes and a predetermined number of iterations of sampling and coincidence-counting as described above, the determining being performed before sampling and collecting, at the same time or after sampling and collecting;

comparing, for any set of k attributes and number of iterations of sampling and coincidence-counting, the observed count versus the expected count of coincidences, and from this comparison determining a measure of correlation (or association, or dependence) for the set of k attributes; and reporting a set of k-tuples of correlated attributes, where a k-tuple of correlated attributes is a set of k of the $N_A$ attributes which have been determined by this process to have a value for a chosen correlation measure above a predetermined threshold value.

In a second aspect the invention provides a coincidence detection method for use with a data set of objects having a number of attributes, the method comprising the steps of:

sampling a subset of the data set for a predetermined number of iterations, each iteration the sampled subset of the data set having for each object the same subset of attributes;

detecting, and recording counts of, coincidences in each sampled subset of the data set, a coincidence being the co-occurrence of a plurality of attribute values in one or more objects in a sampled subset of the data set, where the plurality of attribute values is the same for each occurrence, the detecting and recording counts of coincidences in each sampled subset of the data set being performed before, at the same time or after sampling, detecting and recording counts of coincidences in other subsets;

determining an expected count for each coincidence of interest, the determining being performed before, at the same time, or after sampling, detecting and recording;

comparing, for each coincidence of interest, the observed count of coincidences versus the expected count of coincidences, and from this comparison determining a measure of correlation for the plurality of attributes for the coincidence; and reporting a set of k-tuples of correlated attributes, where a k-tuple of correlated attributes is a plurality of attributes for which the measure of correlation is above a respective pre-determined threshold.

In any of its aspects the comparison of observed and expected counts may be calculated using a Chernoff bound on tail probabilities, and counts may be recorded by storing a running total of the count of each coincidence over all of the sampled subsets.

In a third aspect the invention provides a method for visual exploration of a data set of objects having a number of attributes, the method comprising the steps of:

sampling a subset of the data set for a predetermined number of iterations, each iteration the sampled subset of the data set having the same number of objects although not necessarily the same objects and having for each object the same subset of attributes;

detecting, and recording counts of, coincidences in each sampled subset of the data set, a coincidence being the co-occurrence of a plurality of attribute values in one or more objects in a sampled subset of the data set, where the plurality of attribute values is the same for each occurrence, the detecting and recording counts of coincidences in each sampled subset of the data set being performed before, at the same time or after sampling, detecting and recording counts of coincidences in other subsets;

determining an expected count for each coincidence of interest, the determining being performed before, at the same time, or after sampling, detecting and recording;

comparing, for each coincidence of interest, the observed count of coincidences versus the expected count of coincidences, and from this comparison determining a measure of correlation for the plurality of attributes for the coincidence; and reporting a set of k-tuples of correlated attributes to a user through a graphical interface, where a k-tuple of correlated attributes is a plurality of attributes for which the measure of correlation is above a respective pre-determined threshold.

In a fourth aspect the invention provides a pre-processing method for use with a data modelling unit to capture and report to the data modelling unit higher order interactions of a data set of objects having a number of attributes, the method comprising the steps of:

sampling a subset of the data set for a predetermined number of iterations, each iteration the sampled subset of the data set having for each object the same subset of attributes;

detecting, and recording counts of, coincidences in each sampled subset of the data set, a coincidence being the co-occurrence of a plurality of attribute values in one or more objects in a sampled subset, where the plurality of attribute values is the same for each occurrence, the detecting and recording counts of coincidences in each sampled subset being performed before, at the same time or after sampling, detecting and recording counts of coincidences in other subsets;

determining an expected count for each coincidence of interest, the determining being performed before, at the same time, or after sampling, detecting and recording;

comparing, for each coincidence of interest, the observed count of coincidences versus the expected count of coincidences, and from this comparison determining a measure of correlation for the plurality of attributes for the coincidence; and reporting to the data modelling unit a set of k-tuples of correlated attributes, where a k-tuple of correlated attributes is a plurality of attributes for which the measure of correlation is above a respective pre-determined threshold.

In a fifth aspect the invention provides a correlation elimination method for use with a data set of objects having a number of attributes, the method comprising the steps of:

sampling a subset of the data set for a predetermined number of iterations, each iteration the sampled subset of the data set having for each object the same subset of attributes;

detecting, and recording counts of, coincidences in each sampled subset of the data set, a coincidence being the co-occurrence of a plurality of attribute values in one or more objects in a sampled subset of the data set, where the plurality of attribute values is the same for each occurrence, the detecting and recording counts of coincidences in each sampled subset being performed before, at the same time or after sampling, detecting and recording counts of coincidences in other subsets;

determining an expected count for each coincidence of interest, the determining being performed before, at the same time, or after sampling, detecting and recording;

comparing, for each coincidence of interest, the observed count of coincidences versus the expected count of coincidences, and from this comparison determining a measure of correlation for the plurality of attributes for the coincidence; and eliminating a set of k-tuples of correlated attributes, where a k-tuple of correlated attributes is a plurality of attributes for which the measure of correlation is above a respective pre-determined threshold.

In any of the aspects, the objects may be sales transactions, each transaction comprising one or more purchased products, and the attributes may be instances of sale of particular products or types of products. The objects may be time slices and the attributes may be the status of elements in a system. The objects may be time slices and the attributes may be prices, or price changes of, financial instruments or commodities.

In any of the aspects the steps of the method may be represented by the following pseudo-code:

0. begin
1. read (MATRIX);
2. read (R, T);
3. compute_first_order_marginals(MATRIX);
4. csets :={};
5. for iter=1 to T do
6. sampled_rows :=rsample(R, MATRIX);
7. attributes :=get_attributes(sampled_rows);
8. all_coincidences :=find_all_coincidences(attributes);
9. for coincidence in all_coincidences do
10. if cset_already_exists(coincidence, csets)
11. then update_cset(coincidence, csets);
12. else add_new_cset(coincidence, csets);
13. endif
14. endfor 15. endfor
16. for cset in csets do
17. expected :=compute_expected_match_count(cset);
18. observed :=get_observed_match_count(cset);
19. stats :=update_stats(cset, hypoth_test(expected, observed));
20. endfor
21. print_final_stats(csets, stats);
22. end In a sixth aspect the invention provides a coincidence detection system for use with a data set of objects, each object having a plurality of attributes, the system comprising:
  means for sampling a subset of the data set for a predetermined number of iterations, each iteration the sampled subset of the data set having for each object the same subset of attributes;
  means for detecting, and recording counts of, coincidences in each sampled subset of the data set, a coincidence being the co-occurrence of a plurality of attribute values in one or more objects in a sampled subset of the data set, where the plurality of attribute values is the same for each occurrence, the detecting and recording counts of coincidences in each sampled subset being performed before, at the same time or after sampling, detecting and recording counts of coincidences in other subsets;
  means for determining an expected count for each coincidence of interest, the determining being performed before, at the same time, or after sampling, detecting and recording;
  means for comparing, for each coincidence of interest, the observed count of coincidences versus the expected count of coincidences, and from this comparison determining a measure of correlation for the plurality of attributes for the coincidence; and
  means for reporting a set of k-tuples of correlated attributes, where a k-tuple of correlated attributes is a plurality of attributes for which the measure of correlation is above a respective pre-determined threshold.

In the system of the sixth aspect, the means for sampling a subset of the data set may comprise means for dividing the data set into subsets for sampling. The means for detecting and recording counts of coincidences may comprise an array of processing nodes, each processing node detecting and recording a respective subcount of coincidences, and the means for comparing, for each coincidence of interest, said observed count of coincidences to said expected count of coincidences may comprise means for merging said subcounts to provide said observed count. At least one of said processing nodes may comprise a respective subarray of processing nodes that detect and record respective subsubcounts of coincidences, and said means for merging merges said subsubcounts to provide said subcounts and/or said observed count. Each processing node may comprise memory including an input buffer for storing received subsets of the data set and an output buffer for storing the subcount or the subsubcount; and a memory bus that transfers data to and from the memory.

In a seventh aspect the invention provides coincidence detection programmed media for use with a computer and with a data set of objects having a number of attributes, the programmed media comprising:
  a computer program stored on storage media compatible with the computer, the computer program containing instructions to direct the computer to:
    sample a subset of the data set for a predetermined number of iterations, each iteration the sampled subset of the data set having for each object the same subset of attributes;
    detect and record counts of coincidences in each sampled subset of the data set, a coincidence being the co-occurrence of a plurality of attribute values in one or more objects in a sampled subset of the data set, where the plurality of attribute values is the same for each occurrence, the detecting and recording counts of coincidences in each sampled subset being performed before, at the same time or after sampling, detecting and recording counts of coincidences in other subsets;
    determine an expected count for each coincidence of interest, the determining being performed before, at the same time, or after sampling, detecting and recording;
    compare, for each coincidence of interest, the observed count of coincidences versus the expected count of coincidences, and from this comparison determine a measure of correlation for the plurality of attributes for the coincidence; and
    report a set of k-tuples of correlated attributes, where a k-tuple of correlated attributes is a plurality of attributes for which the measure of correlation is above a respective pre-determined threshold.

In an eighth aspect the invention provides a coincidence detection system for use with a data set of objects having a number of attributes, the system comprising:
  a computer; and
  a computer program on media compatible with the computer, the computer program directing the computer to:
    sample a subset of the data set for a predetermined number of iterations, each iteration the sampled subset having for each object the same subset of attributes,
    detect, and record counts of, coincidences in each sampled subset of the data set, a coincidence being the co-occurrence of a plurality of attribute values in one or more objects in a sampled subset of the data set, where the plurality of attribute values is the same for each occurrence, the detecting and recording counts of coincidences in each sampled subset being performed before, at the same time or after sampling, detecting and recording counts of coincidences in other subsets;
    determine an expected count for each coincidence of interest, the determining being performed before, at the same time, or after sampling, detecting and recording,
    compare, for each coincidence of interest, the observed count of coincidences versus the expected count of coincidences, and from this comparison determine a measure of correlation for the plurality of attributes for the coincidence, and
    report a set of k-tuples of correlated attributes, where a k-tuple of correlated attributes is a plurality of attributes for which the measure of correlation is above a respective pre-determined threshold.

In any of its aspects the methods of the invention may further comprise the step of
  representing the objects and attributes in a matrix of objects versus attributes prior to sampling the data set, the data set being sampled by sampling the matrix.

In a ninth aspect the invention provides a product having a set of attributes selected by:
  sampling a subset of a data set representing objects versus attributes for a predetermined number of iterations, each iteration the sampled subset having the same number of objects although not necessarily the same objects and having for each object the same subset of attributes, detecting, and recording counts of, coincidences in each sampled subset of the data set, a coincidence being the co-occurrence of a plurality of attribute values in one or more objects in a sampled subset of the data set, where the plurality of attribute values is the same for each occurrence, the detecting and recording counts of coincidences in each sampled subset being performed before, at the same time or after sampling, detecting and recording counts of coincidences in other subsets, determining an expected count for each coincidence of interest, the determining being performed before, at the same time, or after sampling, detecting and recording, comparing, for each coincidence of interest, the observed count of coincidences versus the expected count of coincidences, and from this comparison determining a measure of correlation for the plurality of attributes for the coincidence, and reporting a set of k-tuples of correlated attributes, where a k-tuple of correlated attributes is a plurality of attributes for which the measure of correlation is above a respective pre-determined threshold.

In a tenth aspect the invention provides a product defined by applying a set of rules generated from:

sampling a subset of a data set representing objects versus attributes for a predetermined number of iterations, each iteration the sampled subset having for each object the same subset of attributes, detecting and recording counts of coincidences in each sampled subset of the data set, a coincidence being the co-occurrence of a plurality of attribute values in one or more objects in a sampled subset of the data set, where the plurality of attribute values is the same for each occurrence, the detecting and recording counts of coincidences in each sampled subset being performed before, at the same time or after sampling, detecting and recording counts of coincidences in other subsets, determining an expected count for each coincidence of interest, the determining being performed before, at the same time, or after sampling, detecting and recording, comparing, for each coincidence of interest, the observed count of coincidences versus the expected count of coincidences, and from this comparison determining a measure of correlation for the plurality of attributes for the coincidence, and reporting a set of k-tuples of correlated attributes, where a k-tuple of correlated attributes is a plurality of attributes for which the measure of correlation is above a respective pre-determined threshold.

In any aspect the methods of the invention may further comprise the step of applying rules that are defined by the reported correlated attributes.

In an eleventh aspect the invention provides a peptide or peptidomimetic including a structural motif of the V3 loop of HIV envelope protein including spatial coordinates of residues A18/Q31/H33.

In a twelfth aspect the invention provides a pharmaceutical composition comprising a ligand that interacts with a protein having a structural motif identified using the method of claim 2, and a pharmaceutically acceptable carrier or exicipient therefor. The ligand may comprise chemical moieties of suitable identity and spatially located relative to each other so that the moieties interact with corresponding residues or portions of the motif. The ligand, by interacting with the motif, may interfere with function of a region of the protein comprising the motif.

In a thirteenth aspect the invention provides a diagnostic agent comprising a ligand that interacts with a protein having a structural motif identified using the method of the earlier aspects of the invention, and a detectable label linked to the ligand.

In a fourteenth aspect the invention provides a pharmaceutical composition for interacting with an envelope protein of human immunodeficiency virus (HIV), the envelope protein including a structural motif of the V3 loop having spatial coordinates of residues A18/Q31/H33, comprising a ligand including at least one functional group that interacts with the motif, and a pharmaceutically acceptable carrier or exicipient therefor. The ligand may include at least one functional group capable of binding to and being present in an effective position in said ligand to bind to residue 18, at least one functional group capable of binding to and being present in an effective position in said ligand to bind to residue 31, and at least one functional group capable of binding to and being present in an effective position in said ligand to bind to residue 33.

In a fifteenth aspect the invention provides a method of designing a ligand to interact with a structural motif of an envelope protein of human immunodeficiency virus (HIV), the method comprising the steps of: providing a template having spatial coordinates of residues A18, Q31 and H33 in the V3 loop of HIV envelope protein, and computationally evolving a chemical ligand using an effective algorithm with spatial constraints, so that said evolved ligand includes at least one effective functional group that binds to the motif. The ligand may comprise at least one functional group capable of binding to and being present in an effective position in said ligand to bind to residue 18, at least one functional group capable of binding to and being present in an effective position in said ligand to bind to residue 31, and at least one functional group capable of binding to and being present in an effective position in said ligand to bind to residue 33.

In a sixteenth aspect the invention provides a method of identifying a ligand to bind with a structural motif of an envelope protein of human immunodeficiency virus (HIV), the method comprising the steps of: providing a template having spatial coordinates of A18, Q31 and H33 in the V3 loop of HIV envelope protein; providing a data base containing structure and orientation of molecules; and screening said molecules to determine if they contain effective moieties spaced relative to each other so that the moieties interact with the motif. A first moiety of the molecule may interact with residue 18, a second moiety of the molecule interacts with residue 31 and a third moiety of the molecule interacts with residue 33.

In a seventeenth aspect of the invention the invention may provide antigens and vaccines embodying the covarying k-tuples described herein.

In an eighteenth aspect the invention provides a product being defined by its interaction with a set of attributes selected by:

sampling a subset of a data set representing objects versus attributes for a predetermined number of iterations, each iteration the sampled subset of the data set having the same number of objects although not necessarily the same objects and having for each object the same subset of attributes, detecting, and recording counts of, coincidences in each sampled subset of the data set, a coincidence being the co-occurrence of a plurality of attribute values in one or more objects in a sampled subset, where the plurality of attribute values is the same for each occurrence, the detecting and recording counts of coincidences in each sampled subset being performed before, at the same time or after sampling, detecting and recording counts of coincidences in other subsets, determining an expected count for each coincidence of interest, the determining being performed before, at the same time, or after sampling, detecting and recording, comparing, for each coincidence of interest, the observed count of coincidences versus the expected count of coincidences, and from this comparison determining a measure of correlation for the plurality of attributes for the coincidence, and reporting a set of k-tuples of correlated attributes, where a k-tuple of correlated attributes is a plurality of attributes for which the measure of correlation is above a pre-determined threshold.

In any of the aspects the objects may be compounds and the attributes may comprise particular chemical moieties. The objects may be peptides or proteins and the attributes may comprise particular structural or substructural patterns or motifs. The objects may be selected from the group consisting of compounds, molecular structures, nucleotide sequences and amino acid sequences and the attributes may be features of the selected objects. The objects may be time slices and the attributes may be biological parameters of genes or gene products. The objects may be documents that are electronically stored and/or electronically indexed and the attributes may be topics. The objects may be customers and the attributes may comprise products purchased or not purchased by those customers. The attributes may further comprise mailings made or not made to the customers. The objects may comprise products and the attributes may comprise customers that have or have not purchased those products. The attributes may further comprise demographic variables of the customers. The objects may be people with a particular disease or disorder and the attributes may be potential contributing factors for the disease or disorder. The objects may be people with a number of different diseases or disorders and the attributes may be potential contributing factors for the diseases or disorders. The objects may comprise factors potentially contributing to a disease or disorder and the attributes may be people with or without those factors, in which case the method associates groups of people of substantially equivalent risk for the disease or disorder.

The objects may be time slices and the attributes may comprise the state of components in a system at time slices prior to failure of the system, in which case the method associates component states that may potentially cause failure of the system.

In the first aspect $r_i$ may be the same for every iteration.

In any of the aspects the method provided may further comprise the steps of first creating a database of transitions between system states, wherein a system state is represented by a value of a state variable, over a chosen time quantum, and presenting the database, in whole or part, as a data set such that each state to state transition set corresponds to one of M objects and so that each state variable corresponds to an attribute.

In any of its aspects the method provided may further comprise the steps of first creating a database of states and actions covering a chosen time quantum and presenting the database, in whole or part, as a data set such that each state/action/state triple corresponds to one of M objects and so that each state variable or action type corresponds to an attribute.

In a nineteenth aspect the invention provides a coincidence detection method for use with a data set of objects having a number of attributes represented in a matrix of objects versus attributes, the method comprising the steps of:

sampling a subset of the matrix for a predetermined number of iterations, each iteration the sampled subset of the matrix having for each object the same subset of attributes;

detecting, and recording counts of, coincidences in each sampled subset of the matrix, a coincidence being the co-occurrence of a plurality of attribute values in one or more objects in a sampled subset of the matrix, where the plurality of attribute values is the same for each occurrence, the detecting and recording counts of coincidences in each sampled subset being performed before, at the same time or after sampling, detecting and recording counts of coincidences in other subsets;

determining an expected count for each coincidence of interest, the determining being performed before, at the same time, or after sampling, detecting and recording;

comparing, for each coincidence of interest, the observed count of coincidences versus the expected count of coincidences, and from this comparison determining a measure of correlation for the plurality of attributes for the coincidence; and reporting a set of k-tuples of correlated attributes, where a k-tuple of correlated attributes is a plurality of attributes for which the measure of correlation is above a respective pre-determined threshold.

In the first aspect numerical correlation values may be reported along with the set of k-tuples of correlated attributes.

BRIEF DESCRIPTION OF DRAWINGS

For a better understanding of the present invention and to show more clearly how it may be carried into effect, reference will now be made, by way of example, to the accompanying drawings which show the preferred embodiment of the present invention and in which:

FIG. 1a is a depiction of a power set of a set with N=6 objects, arranged as a lattice under a subset operation, representing all possible K-triples of columns from the power set.

FIG. 1b is a depiction of the relative portions of all lattice nodes shown (dark squares) or omitted (light squares) by FIG. 1a.

FIG. 2a is a depiction of n-grams for all sizes n=1,2, ..., 6 for the power set of FIG. 1a.

FIG. 3b illustrates the relevant correlations from FIG. 3a out of the powerset of FIG. 1a.

In FIG. 4a, the observables are formed into three cliques: $(C_1, (C_2, C_5, C_6),$ and $(C_3, C_4))$.

FIG. 4b illustrates the partition of FIG. 4a out of the power set of FIG. 1a.

FIG. 5a is a depiction of three iterations of sampling of a dataset in accordance with one embodiment of the invention.

FIG. 5b is a depiction of the three iterations of sampling of FIG. 5a with explanatory notes.

FIG. 15a is a diagram of residues for given sequences for the sample 3D structure of FIG. 15b where coincidence of sequences may indicate conserved, physical or structural relationships.

MODES FOR CARRYING OUT THE INVENTION

Figure 2A:
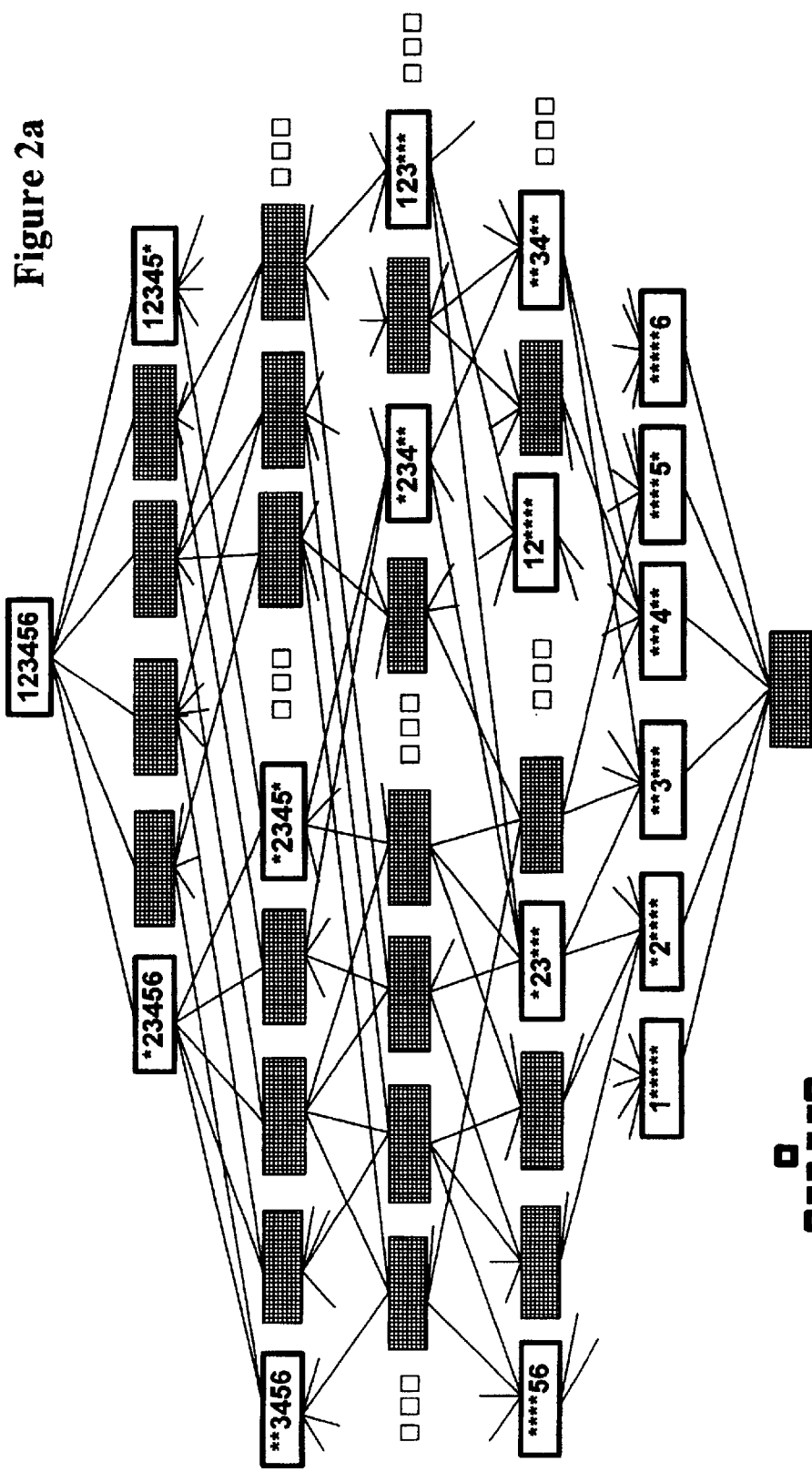
Figure 2B:
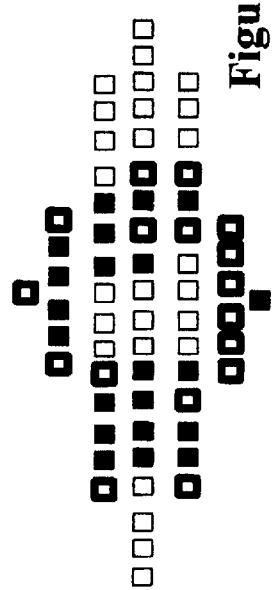
FIG. 2b is a depiction of the relative portion of all lattice nodes shown or omitted in FIG. 2a with a subset of the terms highlighted.
Figure 3A:
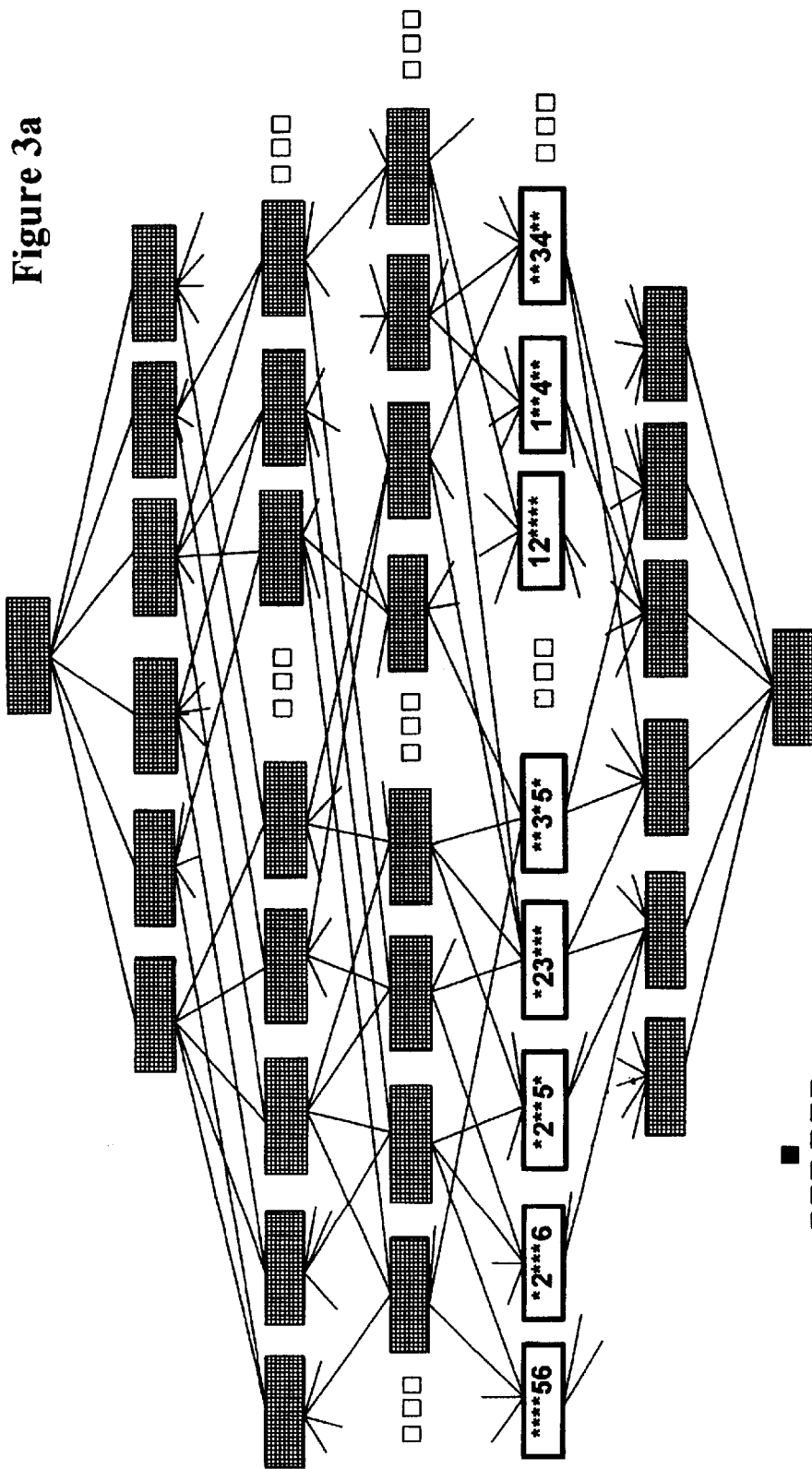
FIG. 3a is a depiction of all possible pairwise correlations for the power set of FIG. 1a, corresponding to analysis of the third tier up from the bottom of the lattice. This is a shortcut taken in work on inter-residue correlations in protein and RNA sequence families, for example. In another example, this Figure represents the approach taken by a method that simply finds all pairs of sales items that tend to be purchased together by consumers.
Figure 3B:
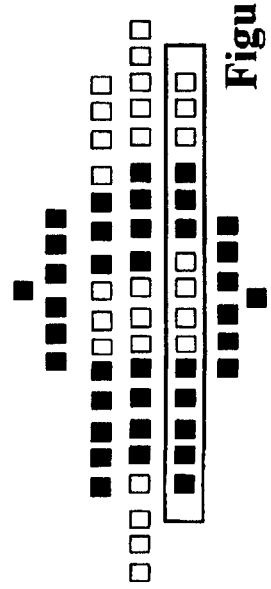
Figure 4A:
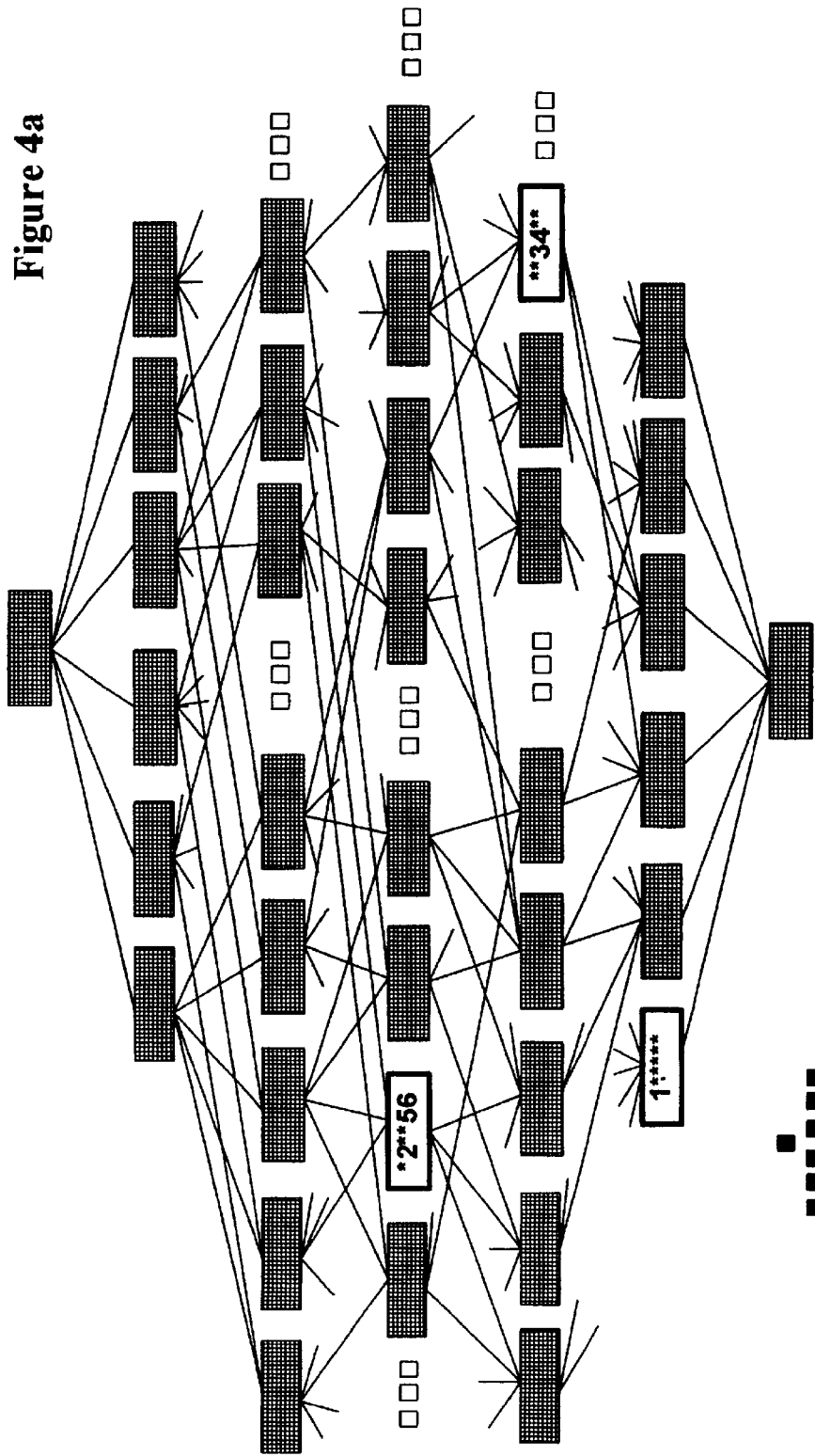
FIG. 4a is a depiction of a partition of the variables of the objects of the power set of FIG. 1a. A partition is one particular and important kind of componential model of a sequence family or other aligned dataset. In a componential model, a set of $N_Y$ latent $y_i$ variables is found to "generate" or "explain" a larger set of N observable variables $c_j$. In a partition model, $N_Y \leq N$, each $c_j$ is generated by exactly one of the $y_i$, and typically $N_Y < N$. The observables corresponding to one latent variable form a kind of clique, and presumably are highly correlated with each other and relatively uncorrelated with variables outside the clique.
Figure 4B:
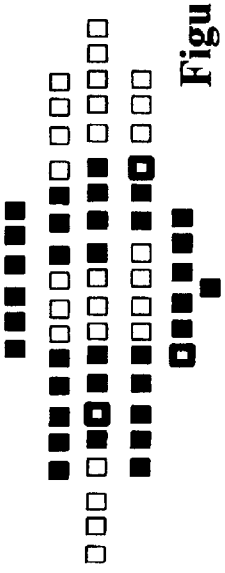

As previously set out, a base method described herein employs the steps of:

representing a set of M objects in terms of a number $N_A$ of variables ("attributes"), where an attribute is said to occur in an object if the object possesses the attribute;

sampling a subset of $r_i$ out of the M objects, for each iteration among a predetermined number of iterations;

detecting and recording coincidences among sets of k of the attributes in each sampled subset of objects, a coincidence being the co-occurrence of $1 \leq k \leq N_A$ attributes in the same $h_i$ out of $r_i$ objects in the sampled subset, where $0 \leq h_i \leq r_i$;

determining an expected count of coincidences for any set of k attributes and a predetermined number of iterations of sampling and coincidence-counting as described above, the determining being performed before sampling and collecting, at the same time or after sampling and collecting;

comparing, for any set of k attributes and number of iterations of sampling and coincidence-counting, the observed count versus the expected count of coincidences, and from this comparison determining a measure of correlation (or association, or dependence) for the set of k attributes; and reporting a set of k-tuples of correlated attributes, where a k-tuple of correlated attributes is a set of k of the $N_A$ attributes which have been determined by this process to have a value for a chosen correlation measure above a predetermined threshold value.

An alternative base method can include the following steps:

sampling a subset of the data set for a predetermined number of iterations, each iteration the sampled subset of the data set having for each object the same subset of attributes;

detecting, and recording counts of, coincidences in each sampled subset of the data set, a coincidence being the co-occurrence of a plurality of attribute values in one or more objects in a sampled subset of the data set, where the plurality of attribute values is the same for each occurrence, the detecting and recording counts of coincidences in each sampled subset of the data set being performed before, at the same time or after sampling, detecting and recording counts of coincidences in other subsets;

determining an expected count for each coincidence of interest, the determining being performed before, at the same time, or after sampling, detecting and recording;

comparing, for each coincidence of interest, the observed count of coincidences versus the expected count of coincidences, and from this comparison determining a measure of correlation for the plurality of attributes for the coincidence; and reporting a set of k-tuples of correlated attributes, where a k-tuple of correlated attributes is a plurality of attributes for which the measure of correlation is above a respective pre-determined threshold.

The modes described herein provide extensions to the base methods described above and employ similar principles. The principles of one application as described herein may be applied to the others as appropriate. Thus, the description of all elements of an application will not always be repeated for each application.

In the preferred embodiment it is preferred for simplicity of programming and interpretation to use a matrix where the objects are rows and the attributes are columns; however, this is not strictly required and any of the embodiments can utilize a data set of objects and attributes that are not represented in the form of a matrix by sampling subsets of the data set directly. As known to persons skilled in the art, any relational database can be easily transformed into a 2-dimensional matrix format.

The embodiments described herein lend themselves particularly well to parallel processing as the steps of detecting, recording and counting coincidences for each of the r samples can be performed simultaneously across many different samples or other subsets of the data set.

Each of the features or variables describing an object may be numerical or qualitative. If qualitative, a feature or variable described in terms of some number z of levels or qualities may be transformed into a numerical variable with z possible values or states. A numerical variable with z possible values or states may be transformed into z binary variables, termed attributes. A numerical variable or feature with a continuous range of possible values or levels may be transformed into, or represented by, a variable with z possible values or states and therefore may also be transformed into, or represented by a set of z binary attributes.

More formally, assume that we are given a database of M objects $O_1, O_2, \ldots, O_M$ each of which is characterized by particular values $a_{ij} \in A_j$ for each of N discrete-valued variables $v_j$. A particular value for a particular variable is denoted $a_1 @ v_j$. One may start with continuously-valued variables and use any of several known methods to quantize them into discrete variables. We also note that, in many applications, the same alphabet A of possible values is used for all the variables. Each object might be a particular record in a database, or may be a sample from a random source.

If the initial N variables are not binary then they can be converted into a set of $N_A$ attributes. For example, in the input listing attached in Appendix "B" each amino acid position is a variable that has 20 possibilities corresponding to the 20 naturally occurring amino acids represented by a subset of letters from the alphabet. In order to turn the variables into binary attributes, each variable becomes 20 different attributes having 1 of 2 states, such as "A" or "not A", "B" or not "B", and so on. An embodiment for representing variables of this type is included in the source code listing in Appendix "A". Other techniques for representing data as attributes could be used.

The principles set out in this description can also be extended to higher orders of attributes, for example trinary attributes to be used with higher order computing machines. The binary examples used herein are the simplest to implement.

This situation can be represented by a table in which each row stands for an object, each column stands for an attribute, and in which therefore each table entry $a_{ij}$ stands for the fact of the ith object having value written at $a_{ij}$ for the jth variable. We can also write $c_j$ (for "column j") and an attribute as $a_i @ c_j$.

For example, consider this small matrix of six rows (objects) and six columns (variables).

| col1 | col2 | col3 | col4 | col5 | col6 |
|------|------|------|------|------|------|
| A | B | C | D | E | F |
| W | U | C | V | E | G |
| Z | L | C | M | W | M |
| V | U | C | V | A | G |
| A | B | C | D | Z | Z |
| W | L | C | M | E | Z |
|   | ↑ |   | ↑ |   |   |

Object number 1 has value 'A' for variable 1, 'B' for variable 2, 'C' for variable 3, and so on. For some applications, it might be useful to find out that, for example, variables 2 and 4 are correlated. In the toy (small fictional) matrix example above, this correlation appears plausible, because whenever an object has B@2, it also has D@4; whenever an object has L@2, it has M@4; and whenever an object has U@2, it also has V@4. Attribute number 3 does not vary—every object has the attribute C@3, and therefore it does not correlate in an interesting way with any other variable.

Given a matrix of data, we further assume that there is some "true" underlying probability distribution q( ) which, for all order $k=1, 2, \ldots, N_A$ specifies the probabilities for each possible k-tuple of attributes. For example, for k=1, we have $q(c_j): A_j \rightarrow [0, 1]$, and we might have for some dataset $q(B@2)=0.33$. A distribution also specifies higher-order probabilities, like, for example, $q(B@2, F@6)=0.166$. Inherent in the particular problems posed is the problem of estimating or approximating the distribution q( ), or at least parts of it.

The problem is to find some, or all, k-tuples of columns $(c_{j1}, c_{j2}, \ldots, c_{jk})$, for $k=2 \ldots N_A$, whose correlation is greater than some predetermined value. For example, one may want a procedure which, given an M-by-N table of values, returns a list of k-tuples of column indices $(j_1, j_2, \ldots, j_{kj})$ such that $D(q(v_{j1}, v_{j2}, \ldots, v_{jk}) \| \Pi_{l=1 \ldots k} q(v_{j1})) > \rho_k$ for some real number $\rho_k$. Here $D(p_1 \| p_2)$ is the Kullback divergence measure, which in this case estimates the difference between the observed distribution of values over the column variables versus the distribution wherein all the column variables are statistically independent. The Kullback measure is just one of many possible measures of correlation or association applicable to this type of problem.

For our purposes we consider correlation in terms of deviation from statistical independence. One can compare an observed number of occurrences of some event in viewing the database versus the number of expected if an underlying hypothesis of independent variables were true. That is, the problem is: Given the table of values, for all $k=2 \ldots N_A$, return a list of all k-tuples of attributes $(a_{i1}@c_{i1}, a_{i2}@c_{i2}, \ldots, a_{ik}@c_{ik})$ such that $$P(\text{Observed}(a_{i1}@c_{i1}, a_{i2}@c_{i2}, \ldots, a_{ik}@c_{ik}) | \text{Independent} (c_{i1}, c_{i2}, \ldots, c_{ik}), \text{Model}) < \theta,$$

for some observed behaviour of $(a_{i1}@c_{i1}, a_{i2}@c_{i2}, \ldots, a_{ik}@c_{ik})$, for some real number threshold $\theta_r \in [0, 1]$, and some Model which underlies one's estimation or hypothesis testing method.

The sampling subprocess may be random sampling, and if random it may be subject to any of a number of possible probability distributions over the objects, including a uniform distribution. Similarly, there may be constraints on the statistical independence or dependencies between each of the T samples drawn during the operation of the method, and between each of the r objects drawn within one sample.

Sample Advantages of Preferred Embodiments

There is at least one class of problems, arising in many diverse application areas, on which the comparative advantages of the coincidence detection method and apparatus described above and further to be described below are most apparent. Such problems are characterized by:

1. a large number of attributes (columns, in our representation);
2. the possible existence of some number of cliques of highly mutually correlated attributes in the dataset, each member attribute of each such clique being relatively uncorrelated with attributes outside its own clique; and
3. lack of prior knowledge as to the precise number, width (k, as in k-ary correlation and kth-order feature), and location of such attribute cliques.

All other procedures of which we are aware either place prior limitations on the width k of discoverable k-tuples, or implement an exhaustive search, serial or parallel, over all or nearly all possible k-tuples of attributes. To put it more simply, the method of the preferred embodiment takes approximately the same computation time and memory to find a 44-ary correlation as it takes to find a 2-ary correlation in the same very high dimensional dataset. Most prior methods, in contrast, either rule out the discovery of the 44th-order feature or else require the allocation of orders of magnitude more time or space in order to find it.

Sample Applications of Preferred Embodiments

Modellers of very large data sets are thwarted in their attempts to compute very far into a fully higher-order probabilistic model by both the computational complexity of the task and by the lack of data needed to support statistically significant estimates of most of the higher-order terms.

The preferred embodiment computes only a subset of higher-order probabilities, and extracts a limited selection of higher-order feature ("HOFs") for construction of a database model. Efficient use can be made of limited computing resources by pre-selecting sets of higher-order features using the correlation-detection methods described herein, and building the most significant (statistically and in terms of application-specific criteria) into model-based classifiers and predictors based on existing statistical, rule-based, neural network, or grammar-based methods. The pre-selected sets of HOFs can be used to create rules for such systems. For example, a data set may be analysed using the methods set out herein to determine that if a company is filing a patent application then it should file an assignment from the inventor. This rule is then used in the system to generate assignments whenever it is determined that a company is filing a patent application. Many rule-based networks could benefit from pre-processing using the methods described herein, see for example, the System and Method for Building a Computer-Based Rete Pattern Matching Network of Grady et al. described in U.S. Pat. No. 5,159,662 issued Oct. 27, 1992; the inference engine of Highland et al. described in U.S. Pat. No. 5,119,470 issued Jun. 2, 1992; and the Fast Method for a Bidirectional Inference of Masui et al. described in U.S. Pat. No. 5,179,632 issued Jan. 12, 1993.

The discovered HOFs can alternatively be used directly to create products, for example, in the prediction or determination of protein structure, when fed into existing methods based on distance geometry or empirically-estimated patterns of cooperativity and folding, or in marketing schemes based on correlated product sales information.

Later below, practice of the principles described herein using the Los Alamos HIV Database is described. In particular, the principles were applied to study of the V3 loop of envelope proteins of human immunodeficiency virus (HIV). In biochemistry and molecular biology in general, covariation of particular residues of a protein likely indicates the existence of a structural motif characterizing a region of the protein that has a functional, physiological role.

Envelope proteins are partially embedded in the lipid membrane surrounding a virus particle, and project externally from the lipid. When the lipid of an HIV particle fuses with the membrane of a host cell during infection, envelope proteins may also protrude from the membrane of the infected cell. The V in V3 stands for "variable", as the sequence of the V3 loop is highly variable between different virus isolates.

Previously, a Los Alamos group in B. T. M. Korber, R. M. Farber, D. H. Wolpert and A. S. Lapedes, "Covariations in the V3 loop of HIV-1: An information-theoretic analysis", Proc. Nat. Acad. Sci. U.S.A. 90 (1993), the disclosure of which is hereby incorporated herein by reference, described 2-ary covariation mutations in certain residues of the V3 loop of HIV 1 envelope proteins. Practice of the present principles has confirmed some of the Los Alamos group's results, but has further permitted the discovery of other highly covarying groups of residues. Whereas the Los Alamos group could only discover pairwise covariation, we describe herein k-ary residue covariation, where k>2. That is, we have identified previously unrecognized motifs of HIV envelope protein.

For a particular trial, input consisted of the respective amino acid sequences of V3 regions from 657 different virus isolates, and is shown in Appendix "B". Source code used on the input is shown in Appendices "A" and "D", named "File coinc.p1" and "File probsort.p1", respectively. Output is shown in Appendix "C".

Referring to Tables C.1 through C.9 set out elsewhere below, the results of 6 separate trials are shown. Parameter values are as indicated in the respective legends. In each Table, the results are ordered by statistical significance, with the most significant correlation first, and the standard one-letter amino acid code is employed. Thus, referring to Table C.6, the most significant coincidence observed is the occurrence of alanine (A) at residue 18, glutamine (Q) at residue 31, and histidine (H) at residue 33. This, like other coincidences set forth on the cited pages, represents the identification of a structural motif of the HIV-1 V3 loop which comprises these residues.

Continuing with the particular example of A18/Q31/H33, the V3 structural motif comprising these residues presumably exists on the exterior of the virus particle, and that region of the V3 loop likely performs a specific function which requires the particular structural motif. Thus, the structural motif would have to be conserved after mutation (s) to preserve that function. This reasoning is extended to other coincidences identified herein.

The identification of a particular conserved structural motif of HIV has several uses.

Using techniques known in the art, a peptide embodying the motif could be produced for use as an antigen. Accordingly, a vaccine could be prepared. The peptide embodying the motif might be made using known recombinant methods, as are described generally, for example, in Maniatis et al., Molecular Cloning: A Laboratory Manual, Cold Spring Harbor Laboratory, Cold Spring Harbor, N.Y. (1982) and in Sambrook et al., Molecular Cloning: A Laboratory Manual ($2^{nd}$ Edition), Cold Spring Harbor Laboratory, Cold Spring Harbor, N.Y. (1989). Alternatively, the peptide or a peptidomimetic might be chemically synthesized using standard chemical techniques. Monoclonal antibodies to the peptide or peptidomimetic could be generated using standard methods, as described for example, in Harlow, E and Lane, D., Antibodies: A Laboratory Manual, Cold Spring Harbor Laboratory, Cold Spring Harbor, N.Y. (1988). Fragments of such monoclonal antibodies, for example, $F_{ab}$ fragments, that have specific affinity for the novel structural motif could also be generated.

In another embodiment, a ligand that interacts with a structural motif identified according to the invention could be generated. That is, the ligand would be characterized by having chemical moieties of suitable identity and spatially located relative to each other so that the moieties interact with corresponding residues or portions of the motif. In some embodiments, the ligand could be an agent, eg. a drug) that, by binding to the motif; interferes with function of the region. The ligand would therefore be an HIV antagonist with potential therapeutic utility. Alternatively, the ligand could bind to the particular V3 region comprising the identified motif, providing diagnostic utility. Such diagnostic utility can be ex vivo. A ligand with diagnostic utility (e.g., an antibody) might comprise a label, such as a fluor or an enzyme conjugate for use in a colorimetric reaction. Fluorescence-labelled viruses or virus-infected cells could be visualized or counted using fluorescence microscopy of FACS (fluorescence-activated cell sorting).

Methods of designing and identifying ligands that bind to structural motifs identified according to the invention are also provided by the invention.

Thus, in one embodiment, the invention provides a ligand for binding with an envelope protein of human immunodeficiency virus (HIV), wherein the envelope protein includes a structural motif comprising amino acid residues A18/Q31/H33. The ligand includes at least one functional group capable of binding to the motif. In a preferred embodiment, the ligand includes at least one functional group capable of binding to and being present in an effective position in said ligand to bind to residue 18, at least one functional group capable of binding to and being present in an effective position in said ligand to bind to residue 31, and at least one functional group capable of binding to and being present in an effective position in said ligand to bind to residue 33.

In another embodiment, the invention provides a method of designing a ligand to bind with a structural motif of an envelope protein of human immunodeficiency virus (HIV). The method includes providing a template having spatial coordinates of A18, Q31 and H33 in the V3 loop of HIV-1 envelope protein, and computationally evolving a chemical ligand using an effective algorithm with spatial constraints, so that said evolved ligand includes at least one effective functional group that binds to the motif. In a preferred embodiment, the ligand includes at least one functional group capable of binding to and being present in an effective position in said ligand to bind to residue 18, at least one functional group capable of binding to and being present in an effective position in said ligand to bind to residue 31, and at least one functional group capable of binding to and being present in an effective position in said ligand to bind to residue 33.

In another embodiment, the invention provides a method of identifying a ligand to bind with a structural motif of an envelope protein of human immunodeficiency virus (HIV). The method includes: providing a template having spatial coordinates of A18, Q31 and H33 in the V3 loop of HIV-1 envelope protein; providing a data base containing structure and orientation of molecules; and screening said molecules to determine if they contain effective moieties spaced relative to each other so that the moieties interact with the motif. In a preferred embodiment, a first moiety of the molecule interacts with residue 31, a second moiety of the molecule interacts with residue 31 and a third moiety of the molecule interacts with residue 33.

The principles described herein encompass similar respective embodiments, including antigens and vaccines, for the other covarying k-tuples described herein, that is, both residues of the V3 loop that covary, and particular amino acids at certain residues that covary.

The method of the current invention can be viewed as a "high-pass filter" for detection of higher-order features. Such HOFs play an important role in database modelling, machine learning, and perception and pattern-recognition. In database mining and modelling contexts, a procedure for discovery of these features might serve any of several major roles, including:

1. Preprocessing of large, complex datasets: Many of the best modelling methods, including Gibbs models, Hidden Markov Models and EM, MacKay's density networks, and related factorial learning methods from the neural network community, could be helped significantly in capturing higher-order interactions without exhaustive search or combinatorial explosion of parameter space if preceded by a fast preprocessing procedure, such as one provided by implementing the principles described herein, that found plausibly correlated variables in the database.
2. Visual exploration of large complex data sets: If coupled to even a simple graphical display interface, a procedure such as ours permits a user to view quickly (with small number of r-samples) the most plausibly interesting higher-order features in high-dimensional data.
3. Pre-conditioning and redundancy elimination: Thus far, we have stressed the utility of finding inter-attribute correlations in order to use them in the building of models; but in many optimization, learning and data-fitting applications, one requires that correlations between variables be found and eliminated, through any of a number of subspace methods like principal components analysis (PCA).

An Embodiment Using a Programmable Digital Computer

Components for Digital Computer Embodiment

Data Matrix, Sampling, and Coincidences. Given a set of M objects, each of which has either a "Yes" (representable by 1) or "No" (representable by 0) value for each of a fixed set of $N_A$ attributes, the input dataset can be arranged into an M-by-$N_A$ table of values, which we shall call the data matrix or simply matrix, and this matrix, as well as its sub-matrices and related vectors that comprise functional parts of the system/process described below, are stored in memory locations within a programmable computer. In this representation the rows of the matrix correspond to objects, and the columns correspond to attributes. The matrix may be labelled as $V_{ij}$ and each element of this two-dimensional table labelled by $v_{ij} \epsilon \{0, 1\}$, where i refers to the ith object (row) $o_i$ and j refers to the jth attribute (column) $a_j$. The set of objects may be listed, for the purposes of this description, as $O=o_1, o_2, \ldots, o_M$ and the set of attributes may be listed as $A=a_1, a_2, \ldots, a_{NA}$.

FIG. 5*b* illustrates these terms as applied to the example illustrated in FIG. 5*a* discussed in more detail below with regard to the program method description of a preferred embodiment.

A particular attribute $a_i$ may be said to occur in a particular object (row) i if $a_{ij}=1$.

Given an ordered list of $1 \leqq m \leqq M$ objects (rows) 5, an incidence vector 2 for an attribute $a_j$ may be defined as the binary vector or string of length m such that the gth bit is 1 if and only if the attribute $a_j$ occurs in the gth object in the given list of objects. The incidence vector 2 is a simple representation of the pattern of occurrence of the attribute over some set of objects, for example, the set of all M objects or the set of objects corresponding to one r-sample as described below.

An r-sample, for example the three rows identified by reference numeral 4 in FIG. 5A, is a set of r of the M records drawn randomly from some probability distribution. In some preferred embodiments, the rows within sample are considered to be drawn independently from a uniform distribution.

The drawing of an r-samples sample 4 is performed by the system one time within each of a specified number of iterations. In some preferred embodiments, the samples drawn over the total number T or iterations are considered to be drawn independently from a uniform distribution.

In some preferred embodiments, different values of r are used for different sequential iterations of the sampling, and/or for different subsets of the dataset processed by different processing nodes in a parallel computing embodiment. In such cases, we may say that on the ith iteration of in the ith sample, the number of objects sampled is $r_i$. Some advantages of using different sample sizes include: the ability to try, within one run-through of the method, different values of r when one is unsure which values of r are best; and the ability to pick different values of r for different processing nodes in a parallel computing embodiment, in order to make optimal use of different processor sizes/speeds and memory sizes among the different processing nodes. An advantage of using the same, single value of r throughout a run-through of the method is the slight gain in simplicity of the program code.

A coincident set, or cset, may be defined as a pattern comprising the joint appearance of $1 \leq k \leq N_A$ attributes (columns) 1 within some set of objects (rows) 5. That is, given some one or more rows 5 under consideration, there is a cset $a_{j1}, a_{j2}, \ldots, a_{jk}$ if $a_{j1}, a_{j2}, \ldots$ and $a_{jk}$ all occur in the given row or rows. For example, elements A@c1, B@c2, D@c4 identified by reference numeral 3 in FIG. 5b are a coincidence set (cset).

Within the computer memory is stored a data structure termed the cset table, which is a means for storing the identity and occurrence count for each cset that occurs in one or more iterations within the process. The identity of a cset is a list of attributes (columns) comprising the cset; the occurrence count is a number corresponding to the number of occurrences of a cset that have been observed up to a particular iteration within the process, or at the end of all the iterations. In some preferred embodiments, the cset table is implemented as a hash table stored in a computer memory.

A cset has, for a given r-sample, a particular incidence vector, which is its binary-encoded record of occurrences (denoted by '1') non-occurrences ('0') over the r data items in the sample. Therefore a cset, corresponding to a set of k attributes, may have an associated incidence vector; and an individual attribute may have an associated incidence vector.

Figure 5B:
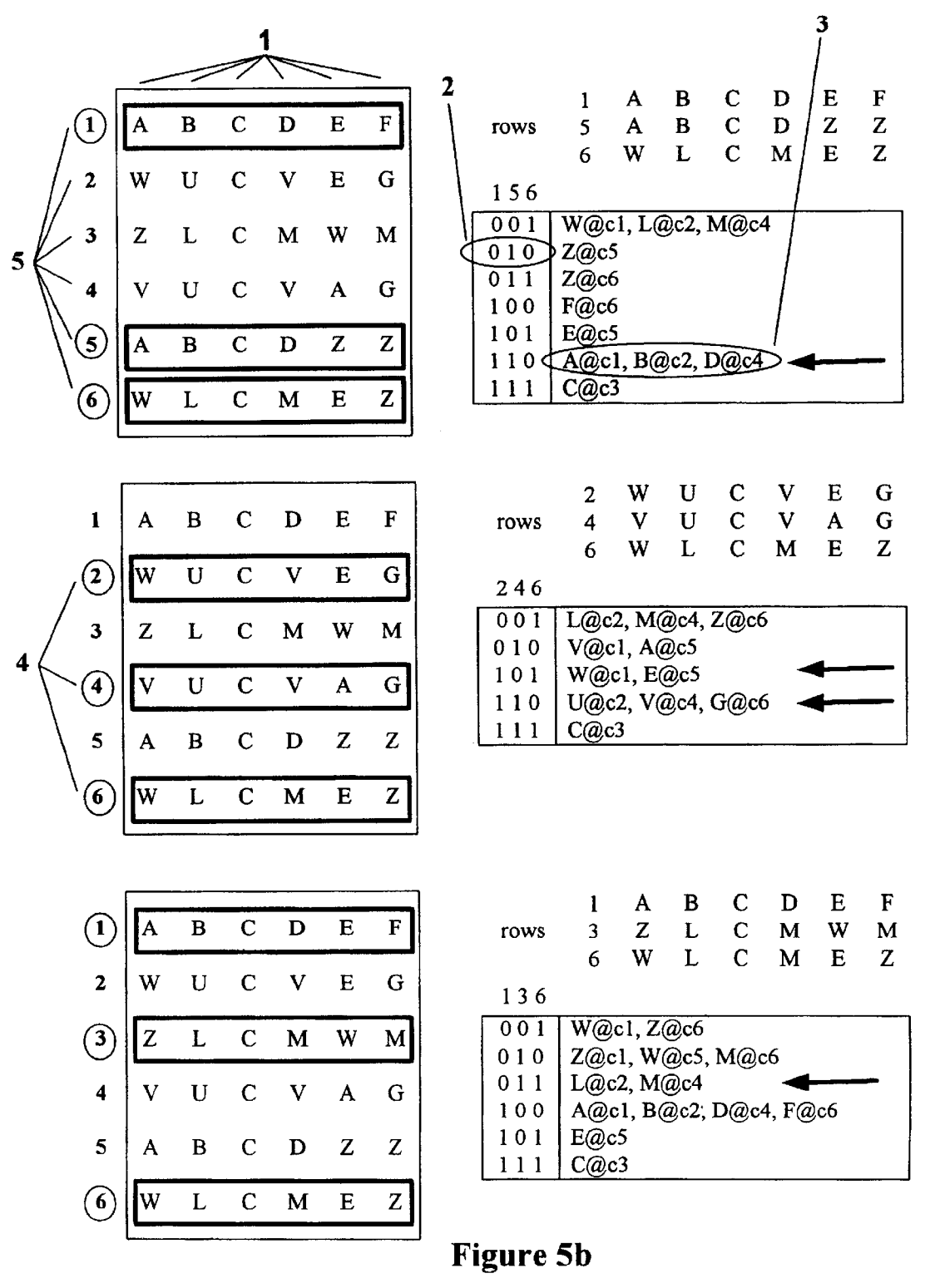

A match (or coincidence) of size h is said to occur, in a given r-sample, for a given cset $\alpha=(a_{i1}, \ldots, a_{ik})$, when $a_{i1}$ appears in h out of the r records, ..., and $a_{ik}$ appears in h out of the r records, and they all appear in exactly the same h out of r records (See FIG. 5b).

Observed Counts of Coincidence. The coincidences are observed, and the corresponding csets stored or updated, by means of a binning method. In each iteration, the attributed are binned, that is, places into separate subsets according to their incidence vectors 2 over the r-sample 4 for the current iteration. In this described matrix-based embodiment of the invention, these vectors act like-r-bit addresses into a very sparse subset of 2' address space. (See FIGS. 5a and 5b).

All the attributes in one bin constitute a cset. The cset is recorded: if the particular cset has occurred in a previous iteration, then its count of occurrences is updated; if it has not occurred previously, then an entry in the cset table is created for it, and then its occurrence count is updated. In this described embodiment, the system stores the number $h: 0 \leq h \leq r$ of occurrences for this and each iteration. After a specified number T of iterations has been completed, the cset table contains a list of all the csets observed, and, for each cset $\alpha$, a total number of observed coincidences, which corresponds to $\Sigma^T_{r=1} h_i(\alpha)$, where $h_i(\alpha)$ is the number of joint occurrences for the k attributes comprising $\alpha$, for the ith iteration.

Expected Count Function. An expected count function is a mathematical function, implemented as a computer program or subroutine, or in electronic or optical circuits, which takes a set of attributes $a_{j1}, a_{j2}, \ldots, a_{jk}$ and a number T and produces a number corresponding to an expected number of coincidences for that set of attributes in a process of T iterations of drawing of r-samples and observing coincidences.

In one particular embodiment of the invention, the function $f_{match}(\alpha, h, r)$ is obtained from the multinomial distribution:

$$f_{match}(\alpha, h, r) = \left(\frac{r!}{h!(r-h)!}\right) p(a_{i1}, \ldots, a_{ik})^h p(\tilde{a}_{i1}, \ldots, \tilde{a}_{ik})^{r-h},$$

This formula gives an estimate of the probability for finding exactly h occurrences of $a_{i1}$, h occurrences of $a_{i2}, \ldots$, and h occurrences of $a_{ik}$, all occurring in the same h rows, in one r-sample.

(This function definition has a simple form because all but two of the large number of p( ) factors in the standard multinomial expression vanish with zero exponents.)

The probability of a match of size h for the k attributes which make up a potential cset has been defined in terms of the joint probability $p(a_{i1}, \ldots, a_{ik})$; the Expected Count Function must employ particular estimates for these joint probabilities. In this preferred embodiment, the joint probability estimates incorporate the hypothesis of independence between the individual attributes. Therefore in the definition formula given above we substitute $$\prod_{l=1}^{k} p(a_{il}) \text{ for } p(a_{i1}, \ldots, a_{ik}) \text{ and } \prod_{l=1}^{k} (1 - p(a_{il})) \text{ for } p(\tilde{a}_{i1}, \ldots, \tilde{a}_{ik}).$$

Hypothesis Test Function and Correlation Measure. An hypothesis test is a mathematical procedure, implemented as a computer program or subroutine, or in special purpose electronic and/or optical hardware, which takes a pair of number $H_{exp}$ and $H_{obs}$, representing the expected and observed numbers of coincidences, respectively, for a particular set of k attributes, and produces a number C representing an estimate of the correlation among the k attributes.

In some preferred embodiments, a Chernoff bound on tail probabilities provides the hypothesis test function, as described below.

Let random variable $X_i$ hold the value $h_i$ for each iteration i, and let $$X = \sum_{i=1}^{T} X_i,$$

and note that $0 \leq X \leq T \cdot r$. The method of Chernoff-Hoeffding bounds [8] provides the following theorem:

Let random variable $X_i$ hold the value $h_i$ for each iteration i, and let $$X = \sum_{i=1}^{T} X_i,$$

and note that $0 \leq X \leq T \cdot r$. The method of Chernoff-Hoeffding bounds [8] provides the following theorem:

Let $X = X_1 + X_2 + \ldots + X_n$ be the sum of n independent random variable s, where $l_i \leq X_i \leq u_i$ for reals $l_i$ ("lower") and $u_i$ ("upper").

Then $$P[X - E[X] > \delta] \le \exp\left(\frac{-2\delta^2}{\sum_i (u_i - l_i)^2}\right). \quad (1)$$

For our purposes, we set n=T and $l_i$=0 and $u_i$=$r_i$ for all i=1, 2, ..., T, and we thereby obtain $$P[X - E[X] > \delta] \le \exp\left(\frac{-2\delta^2}{\sum_i r_i^2}\right) \quad (2)$$

Using this mathematical relationship, an effective procedure for computing a correlation value can be defined:

$$Corr(\alpha) = 1 - \exp\left(\frac{-2(H_{obs} - H_{exp})^2}{\sum_i r_i^2}\right).$$

In the special case wherein the same sample size r is used for every iteration of the sampling, that is, when $r_i$=r for all i=1, 2, ..., T, then the above formulas reduce to the simpler forms:

$$P[X - E[X] > \delta] \le \exp\left(\frac{-2\delta^2}{Tr^2}\right) \quad (2a)$$

$$Corr(\alpha) = 1 - \exp\left(\frac{-2(H_{obs} - H_{exp})^2}{Tr^2}\right).$$

Here the correlation value corresponds to an estimate of 1 minus the probability of having observed $H_{obs}$ coincidences, over T iterations of r-sampling, if the hypotheses underlying the expected count $H_{exp}$ were true. If the assumption of independence between the attributes was used to compute $H_{exp}$ as described above for some preferred embodiments, then this hypothesis test provides a correlation value for each cset that estimates the deviation from independence; that is, it estimates the statistical dependence between the attributes making up the cset.

Operation of the Components Within a Process

Typically, the representation component is performed first within the overall process of the current invention. A plurality of sampling iterations is performed on the representation of the data, and for each r-sample, the detection and recording of coincidences is performed. The sampling iterations may be performed sequentially or in parallel, or in some combination of sequential and parallel steps.

At any stage within the process, the determining of an expected count of coincidences, for some or all of the coincident sets of attributes, is performed. This component of the process may be performed all at once for all coincident sets, or incrementally; sequentially or in parallel, or in some combination. It may be performed for coincident sets (csets) as each coincidence is detected or stored, or may be performed before or after such detection or recording.

After some number of sampling iterations has been performed, the comparing of actual to expected number of coincidences may be performed for some or all recorded coincident sets. This may be done for all csets at once, or for any subsets of them at different points throughout the process. These comparisons for different csets may be performed sequentially or in parallel, or in some combination thereof.

After some number of sampling iterations has been performed, the reporting of sets of correlated attributes may be performed for some or all of the recorded coincident sets that have been determined, in the comparisons, to signal significant correlations between the component attributes. This may be done for all csets at once, or for any subsets of them at different points throughout the process. These comparisons for different csets may be performed sequentially or in parallel, or in some combination thereof.

Program Method Description of a Preferred Embodiment

Below is shown, in pseudocode, a program on appropriate media, for example, a floppy disk, hard drive, RAM or other such media, corresponding to one possible embodiment on a programmable digital computer.

FIG. 5a provides a pictorial example of the application of this embodiment to a fictional toy dataset. Three iterations of r-sampling (for r=3) on the toy dataset are depicted, top to bottom. For each iteration, the left-hand box represents the dataset, with outlined entries representing the sampled rows. The right-hand-box represents the set of bins into which the attributes collide. For example, in the first iteration, A@1, B@2, and D@4 all occur in the first and second of the three sampled rows, so they each have incidence vector 110 and collide in the bin labeled by that binary address. Bins containing only a single attribute are ignored; and "empty" bins are never created at all. All bins are cleared and removed after each iteration, but collisions are recorded in the Csets global data structure.

Procedure to find correlated sets of attributes:
0. begin
1. read (MATRIX);
2. read (R, T);
3. compute_first_order_marginals(MATRIX);
4. csets:={};
5. for iter=1 to T do
6. sampled_rows:=rsample(R, MATRIX):
7. attributes:=get_attributes(sampled_rows);
8. all_coincidences:=find_all_coincidences(attributes);
9. for coincidence in all_coincidences do
10. if cset_already_exists(coincidence, csets)
11. then update_cset(coincidence, csets);
12. else add_new_cset(coincidence, csets);
13. endif
14. endfor
15. endfor
16. for cset in csets do
17. expected:=compute_expected_match_count(cset);
18. observed:=get_observed_match_count(cset);
19. stats:=update_stats(cset, hypoth_test(expected, observed));
20. endfor
21. print_final_stats(csets, stats);
22. end Steps 5 through 21 of the pseudo-code represents the steps of the base method described herein, namely:

sampling a subset of the matrix for a predetermined number of iterations, each subset of attributes being the same, detecting and recording counts of coincidences of attributes in each sampled subset, a coincidence being the occurrence of a plurality of attributes in an object in a sampled subset, where the plurality of attributes is the same for each occurrence, determining an expected count for each coincidence of interest, the determining being performed before, at the same time, or after sampling, detecting and recording, comparing, for each coincidence of interest, the observed count of coincidences versus the expected count of coincidences, and from this comparison determining a measure of correlation for the plurality of attributes for the coincidence, and reporting a set of k-tuples of correlated attributes, where a k-tuple of correlated attributes is a plurality of attributes for which the measure of correlation is above a pre-determined threshold.

Figure 6:
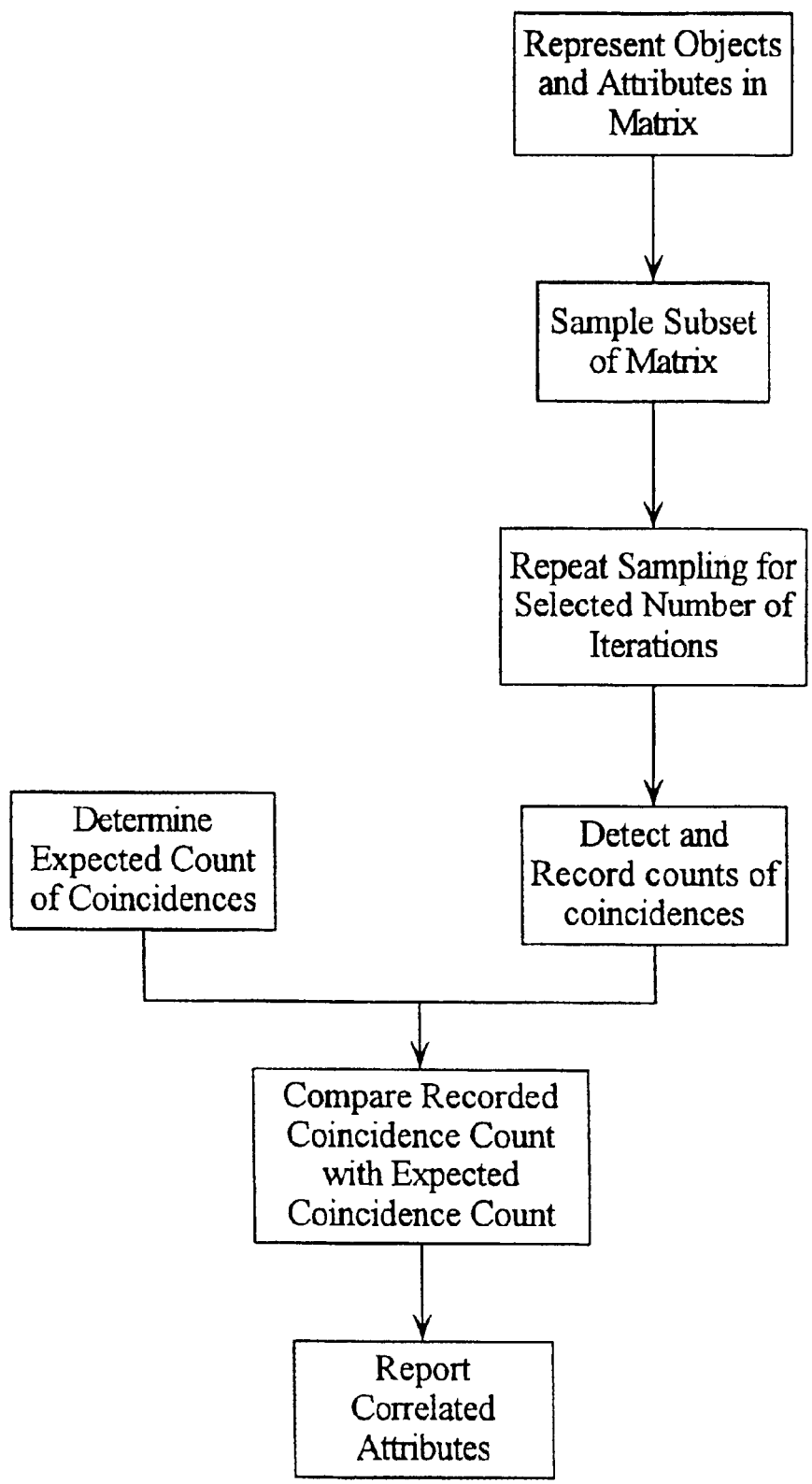
FIG. 6 is a general flow diagram of a program method of a preferred embodiment.
Figure 7:
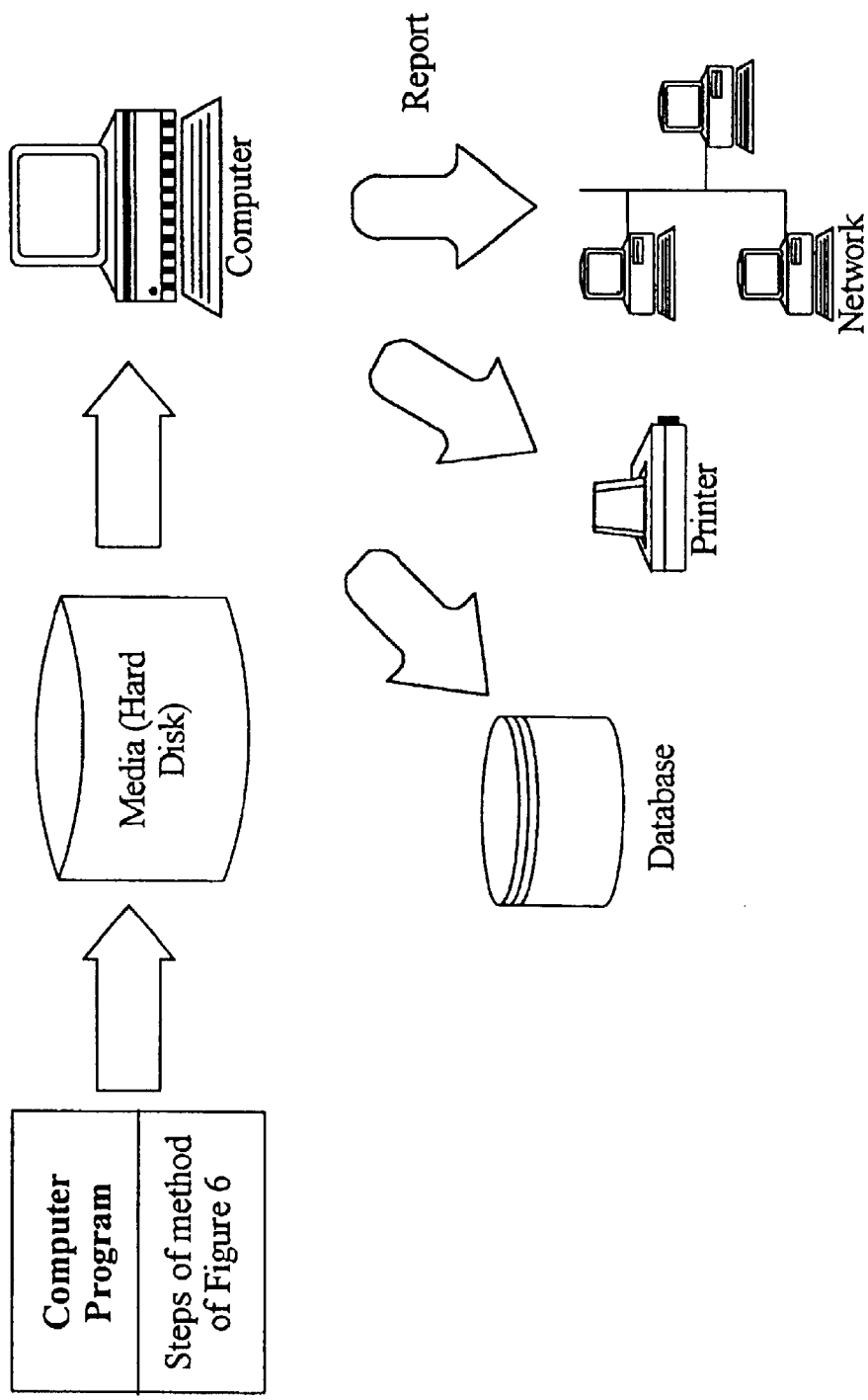
FIG. 7 is a schematic diagram of a system implementing the program method of FIG. 6a, FIG. 8 is a general flow diagram of the program method of FIG. 6a adapted to control a process for production of a product.

Appendix "B" contains actual source code written in the Perl language for running on a Sun4 computer in the Sun UNIX operating system. Sample input data for the code listing in Appendix "B" is listed in Appendix "C" for partial amino acid sequences from V3 loop of HIV envelope proteins. The corresponding output from the code of Appendix "B" for the input of Appendix "C" is shown in Appendix "D". In order to produce the output of Appendix "D", the adjunct Perl language program listed in Appendix "E" was used for clarification and presentation from the main code listing in Appendix "B". A general flow diagram for this embodiment is shown in FIG. 6, while a general block diagram is shown in FIG. 7. The resulting report was stored in a flat file as a relatively unstructured ascii database, which was later printed; it could equally well have been sent to a printer directly or sent across a network for report to other resources.

Alternative Embodiments

Descriptions of alternative embodiments of the present invention may be divided into two categories, described separately below: first, different physical embodiments of the system/process as may be used in many potential problem-specific applications; and, second, different interpretations of the components enumerated in the description above, according to different problem-specific applications of the present invention.

Different Implementations

For example, among the many possible embodiments as programs on programmable digital computers:

The method may be run entirely sequentially, as in the most straightforward interpretation of the pseudocode given above, or the method may be run on parallel (vector or multiprocessor) or distributed computer systems in many possible ways. A set of computations may be run in parallel, in which each computation performs the entire program steps outlined above, but with each separate computation using a different value for r, the sample size; or each separate computation could run the same program steps with same key parameter values, but start with different initial random number seeds for the random r-sampling. Alternatively, the entire program steps outlined above could be run once, but each different r-sample could be forked off into a separate process run on different processors, where in each such process would comprise the detection and optionally recording steps, with the global cset counts later joined into the global process and global data structures. Additionally, the computation of the expected counts, and the comparisons of expected with observed counts, could be performed all at once or incrementally, sequentially or in parallel. Similarly, the reporting of the estimated correlation values can be performed for some or all of the Csets, once at the end of computation or incrementally throughout, in serial or parallel.

The output of the method, which can include the reporting of the significantly correlated k-tuples of attributes (the csets that are deemed sufficiently highly correlated in the comparing, a.k.a., hypothesis testing stage), can be verbal, and/or numerical and/or graphical.

A number of sampling schemes are possible, including deterministic, pseudo-random, or purely random. And if pseudo-random or random, any of a number of random sampling schemes may be used, including hypergeometric and multinomial sampling. The r objects within an r-sample may be sampled "with replacement" or "without replacement". At the next level up, the set of r samples themselves may be drawn "with replacement" or "without replacement".

Different choices for the key sampling parameter r are possible, and it is not necessary to use the same number r for each sample.

Many possible choices exist for T, the number of sampling iterations. It is possible to use any of a number of mathematical methods for choosing T in order to achieve a desired confidence level in the degrees of correlation estimated for the k-tuples of attributes discovered by the method of the current invention. Alternatively, it is possible to run the procedure for a given fixed number of iterations and then print or view the results, or to interleave the running of some number of iterations with the printing or viewing of partial results.

Many possible ways exist for the representation, storage, and accessing of the Csets data structure used during the processing of the algorithm. The Csets data may be stored and accessed via a hash table, a k-d tree, patricia tree (also called a trie), and/or in other ways, known to those skilled in the art, of storing and accessing data efficiently. Whatever data structure is chosen, the structure may be stored physically in registers, in main memory, and/or on secondary or external storage media such as magnetic disks, magnetic tape, or optical storage media.

Alternative to the embodiments of the method on general-purpose computing hardware of various types, there are many possible embodiments on special-purpose electronic, optical, or electro-optical hardware, or some combination of general-purpose and special-purpose architectures and devices.

For example, very efficient special purpose electronic (LSI or VLSI) may be used to implement the matrix representation of the current invention, by the fact that the incidence vectors of attributes are simple binary vectors, by the fact that the coincidence "bins", described earlier in one view of the current invention, correspond to "addresses" to a memory space of size $2^r$ for each r-sample, and by the ability with current technology to design, fabricate and use special-purpose hardware for implementations of random-number generation and sampling, fast-access storage of the Csets data structures, and of the mathematical functions used in the calculation of expected count estimates and hypothesis tests and correlation estimates.

Special Purpose Hardware Method Description of a Preferred Embodiment

1. Overview

Figure 14:
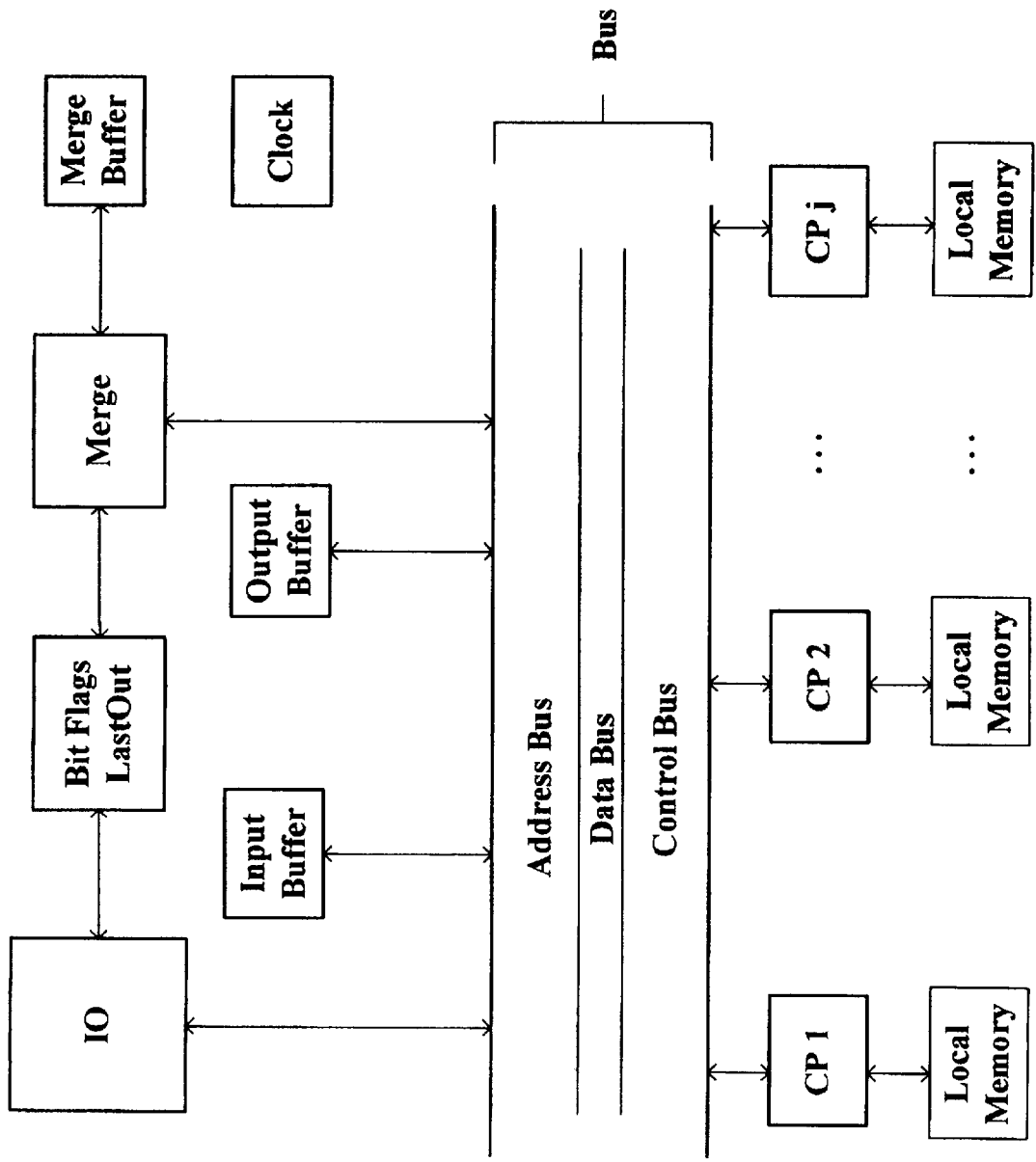
FIG. 14 is a diagram of a node of a hardware implementation of a preferred embodiment.

Referring now to FIG. 14, an embodiment of special purpose hardware mentioned previously is intended to exploit the potential benefits of parallelizing the execution of the algorithm. A node (defined below) divides a given data set along M (the number of rows of data) and distributes these portions to its CPs (also defined below). The CPs may be either other nodes (in a recursive definition) or may be special purpose processors developed to perform step 8 in the method as described in high-level "pseudo-code" in the previous Program Method Description of a Preferred Embodiment Section. When the results have been computed by the node's CPs, the merging step (steps 9 through 14 in the above-noted "pseudo-code" description) is performed by the node. Once the merging has been done, the results are passed back to the node's parent. If the node is the root of the tree, the complete results set is sent back to the driver that controls this hardware. The system described below can be used "off-line" from a main computer's CPU; among other possibilities for commercial marketing and use of such a system is its implementation on a special "board" or "card" that a user can purchase and install on his or her personal computer or workstation. One can also envision the use of one or a number of such special subsystems on a local area network or a "supercomputer" installation. The described embodiment represents only one of many possible ways, as will be understood by those skilled in the art, to parallelize the methods described herein.

This implementation described below is assumed to act solely on character-valued data attributes. This is in no way a limitation of the basic methods described herein, rather it is a specific implementation of the basic methods. The implementation could easily follow a binary-attribute encoding as described elsewhere herein.

A diagram of a node is shown in FIG. 14 with compute processors (CPc). The node includes the following:

A bank of memory where input to be sent to the CPs is stored (the input buffer) and where results found by the CPs will be stored (the output buffer).

A memory bus divided into control, data and address buses used to arbitrate communication on the bus itself as well as being the vehicle for data transfer.

A set of bit flags and a small additional portion of memory (LastOut). LastOut is the address of the section in the output buffer that was last written to. The two bit flags are used by the merge and I/O processors to determine what state they each are in.

An array of size J of compute processors (CPs), each with their own local memory caches, which perform the discovery of coincidences.

A merge processor (MG) which has its own cache of memory in which it writes the merged results of the CPs.

An input/output processor (IO) whose main responsibility is to control use of the bus.

A clock which is used to ensure that each element in the system runs synchronously with respect to every other element. Execution of each of the parts in the system can be thought of as running in lock-step.

Computer processors are defined as being either special processors that perform the R-sampling step of the algorithm (step 8 in the pseudo-code description and graphically in FIG. 5a. This allows the possibility of a tree structure of such nodes rather than limiting embodiments solely to a vector arrangement. For any particular choice of hardware for the memory bus, it may be the case that there is a maximally useful limit on the number of CPs per node. A tree structure allows a way around this limit.

The implementation assumes that maximal values of method parameters R and N (Rmax and Nmax) are specified a priori. It is the responsibility of the software driver to detect when these limits have been violated are react accordingly.

2. Bank of Memory

For each node, memory of size 2*J*Amax*Rmax*Nmax, where Amax is the maximal total number of iterations that can be done in the node. This memory is divided equally into the input and output buffers. Note that the size of the input for a single iteration is no greater than J*Rmax*Nmax and neither the locally-produced results nor the final merged results (formed by combining the partial results from the J CPs) can exceed this limit, so there is no risk of exceeding available memory.

Access to this memory is as follows:

IO has write access to the input buffer and read access to the output buffer.

MG has no access to the input buffer and read access to the output buffer.

CP has read access to the input buffer and write access to the output buffer.

3. Memory Bus

Control of the memory bus is the responsibility of the IO processor. Each CP is assigned a numeric identifier (0 to J+1 as IO is implicitly assigned zero and MG is assigned 1). The memory bus is divided into three sections:

Control: Two wires for each CP, two for MG and two for IO comprise the control bus. The first of each pair is called the request wire while the second is known as the response wire.

Address: Each device in the system is assigned a unique memory address range. The address bus, used in combination with the data bus, determine what device the current value on the data bus will be written to and, if applicable, where within that device it will be stored. The width of the address bus (i.e. the number of wires in it) is determined for a choice of size for the memory storage of input and output and thus will not be specified here.

Data: Given the assumption that only character-valued data attributes will be handled by this system, the data bus is eight wires wide.

Bus arbitration is handled through the use of the control bus. When a device (here meaning MG, IO or one of the CPs) wishes to use the bus, it asserts a logical 1 on its request wire. On any given cycle, more than one device may have done so. IO, when it returns to its bus arbitration duties, simply sets the lowest numbered device's response wire to 1 and zeroes all the other response wires. This tells the lowest identified device that it has permission to use the bus (reads and writes are not indicated—IO is responsible for establishing the context) and all others that they must wait. All devices that wish to use the bus continue to assert 1 on their request wire until given permission. When the permitted device has finished with the bus, the device asserts 0 on its request wire, indicating to IO that it may reassign the bus to another device. "Handshake" and other types of protocols, such as described above, are well-known to and understood by those skilled in the art.

4. Bit Flags and Additional Memory

The additional memory is used by IO to store the last written output section. There is no need to store a list of such sections for MG because "write"s to the output buffer are done incrementally and MG can determine how many unused sections it has waiting by comparing its last read index with the last written index. Only IO can write to this memory and only MG may read from it.

Two bit flags are used to indicate "IO finished" (meaning IO has sent all data out and received all CP output) and "Merge finished".

5. An Array of J Compute Processors

As noted above, these are either nodes or are special purpose processors that compute one R-sampling step in the algorithmic description of the general method of the current invention. In the latter case, they may comprise:

a processor which performs the coincidence detection in addition to the functions listed below 2*Nmax*Rmax sized local memory The memory is split into two equal portions for input and output.

Initially, a CP asserts 1 on its request wire, indicating that it is ready for data. When it sees only its response wire set to one on the following cycle, it expects to be sent the current values for R and N and then the data itself (otherwise, it waits for this to be the case). Based on the first two values, it can determine when the current input is exhausted. It then asserts 0 on its request wire and performs the binning and coincidence detection steps of the method. When these steps have been completed the CP asserts logical 1 again on its request wire, this time indicating its desire to send its results. When given permission to use the bus, it sends its coincidence set to IO. IO is responsible for managing the location for storage of this data. The output stream of the CP comprises a tally of the coincidences found followed by the coincidences (csets) themselves. The coincidences are of the form:

- hit count (no higher than Rmax)
- size (that is, the width of the cset, i.e., the number of component attributes)
- a size-long list of the attributes of the coincidence in form (value, position)

When all data has been sent to IO, the CP asserts 1 on its wire to request more data.

6. Merge Processor MG

The merge processor may comprise:

- a processor that runs the merging step
- NmaxRmax local memory used to store the output from one CP
- counters C1 and C2 (the former tracks the last output section read by MG; the latter counts the number of coincidences currently stored in the merge buffer)
- memory used to store the current value of A
- memory of size JNmaxRmaxAmax used to store the merged results Initially, MG sets its counters to zero and its request wire to zero and waits for IO to signal it (by setting this wire to 1) that there is output data to be processed.

When MG sees that its request wire has been turned on, it knows to start receiving output data indexed by the counter into its local memory. Once this has been accomplished, MG can start the merging algorithm. The merge is done from the local memory directly into the merge buffer (C2 must have the current number of coincidences when this step is finished). When this step is completed, MG retrieves the current value of LastOut. If it is greater than C1, then Mg knows it can increment C1 and move directly on to the next output section. If C1 and LastOut are equal, then MG sets its request wire to zero. If C1 has reached A*J, then MG knows that all the results have been computed and merged (and thus, that all CPs and IO are idle) and that it should set its bit flag to one (indicating that it is finished) and start sending the contents of the merge buffer back to IO for transmission to this node's parent. The results are sent simply as the value of C2 followed by the list of coincidences stored in the merge buffer (the form of the coincidences is identical to that described in section 5 above).

7. Input/Output Processor IO

IO contains:

- a bit vector of size J
- a counter, C1, indicating the next available output bin
- a counter, C2, indicating the next unused R*N portion of input IO is intended to govern the execution of the algorithm as a whole as it is responsible for the bus arbitration scheme outlined earlier. Initially, IO sets C1 and C2 to zero and zeroes its bit vector (indicating that it has sent no data to any CP) and waits for the software driver to start sending it data. During this time, it knows that no work can be done, and thus zeroes all permissions for the bus. An interrupt signals the arrival of data from the driver and IO continues to zero all communication requests until all the data has been written to the input buffer. The incoming data is of form:

N

R

T, the total number of row sets of size R sent data stream of size TRN

IO can thus determine when no more data can be expected. Note that it is the responsibility of the driver to:

- divide data mining requests into sizes no greater than Amax
- ensure that the number of rows sent as input is evenly divisible by R
- ensure that Rmax and Nmax have not bee exceeded by the current data set merge all results sent back from the device Once all input has been stored, IO sends out data of size R*N to each $CP_i$ by first setting the ith bit in the vector to one (this indicates that IO should expect output from $CP_i$), signaling that CP by setting its response wire to 1 while zeroing all others, sending the data onto the bus and finally incrementing C2.

When all CPs are busy (or all available input has been exhausted), IO waits for a CP to assert 1 on its request wire which indicates that it is ready to send back results. Once this signal has been received from a CP, IO retrieves the results from the CP, stores them in the output section indexed by the counter, zeroes the bit associated with that CP, increments C1 and asserts 1 on the MG request wire. If there is unused data in the input buffer, IO sends the next available R*N set to the CP who just returned results (setting the bit for that CP to one). When C2 equals T and the bit vector contains no bits set to 1, then IO knows that it is finished and sets the IO bit flag to 1. At this point, IO goes back to the previously described wait state until it sees the MG bit flag also set to 1 (indicating that MG has finished its work). Once this occurs, IO calls an interrupt (if this node is the root of the tree) or just requests to send (if this node has another node for a parent), gives MG permission to write on the bus and then passes all data sent from MG to the parent.

Note that the proposed scheme allows for unequal execution time among the CPs—the next CP to get data is the one most recently finished with its last allowance of data. Thus, even though the overall operation of the system is clocked, there is a degree of asynchronous processing ability.

The choices for particular processors, buses and other components are open to the discretion of designers, fabircators, manufacturers, sellers, buyers and users, and the ranges of options are known to hose skilled in the art: In particular, all parts of the embodiment described above may be obtained from "off-the-shelf" sources, or may be specially designed at the VLSI level by persons skilled in the art.

Different Applications

General

Special-purpose embodiments are also possible. For example, in an application to marketing and analysis of sales/transactions data, the objects input to the methods of the present invention can correspond to transactions, and the attributes correspond to instances of sale of particular products or services.

In an application to the process management, industrial engineering or computer systems management, the objects can correspond to particular time slices or time periods, and the attributes correspond to the on/off or used/unused status of particular components, resources, or subsystems. The goal of the application could be to find k-ary conflicts or conflicting demands among interacting subsystems or users, in order to improve the efficiency or lower the costs of the operations.

Figure 8:
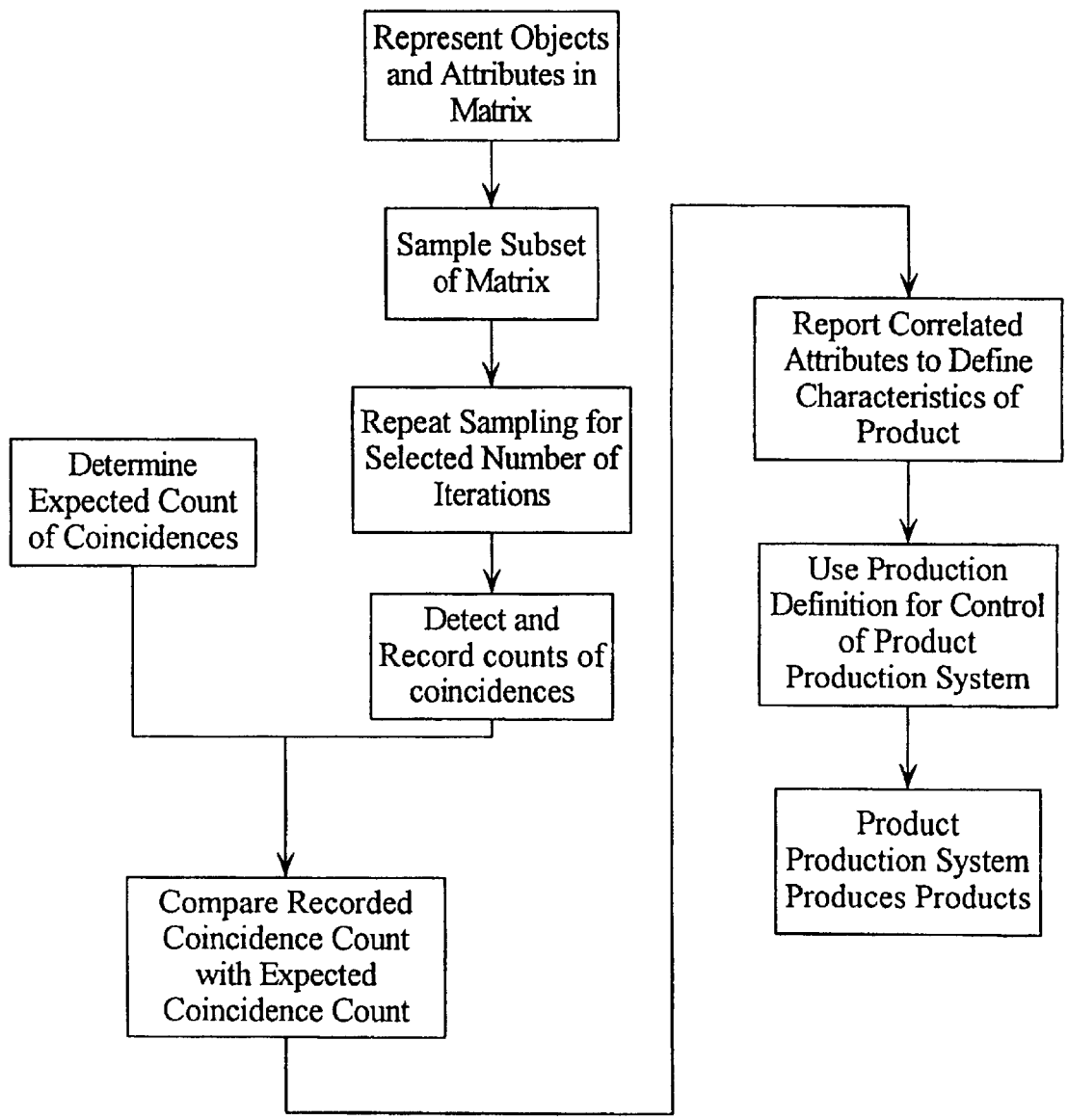
Figure 9:
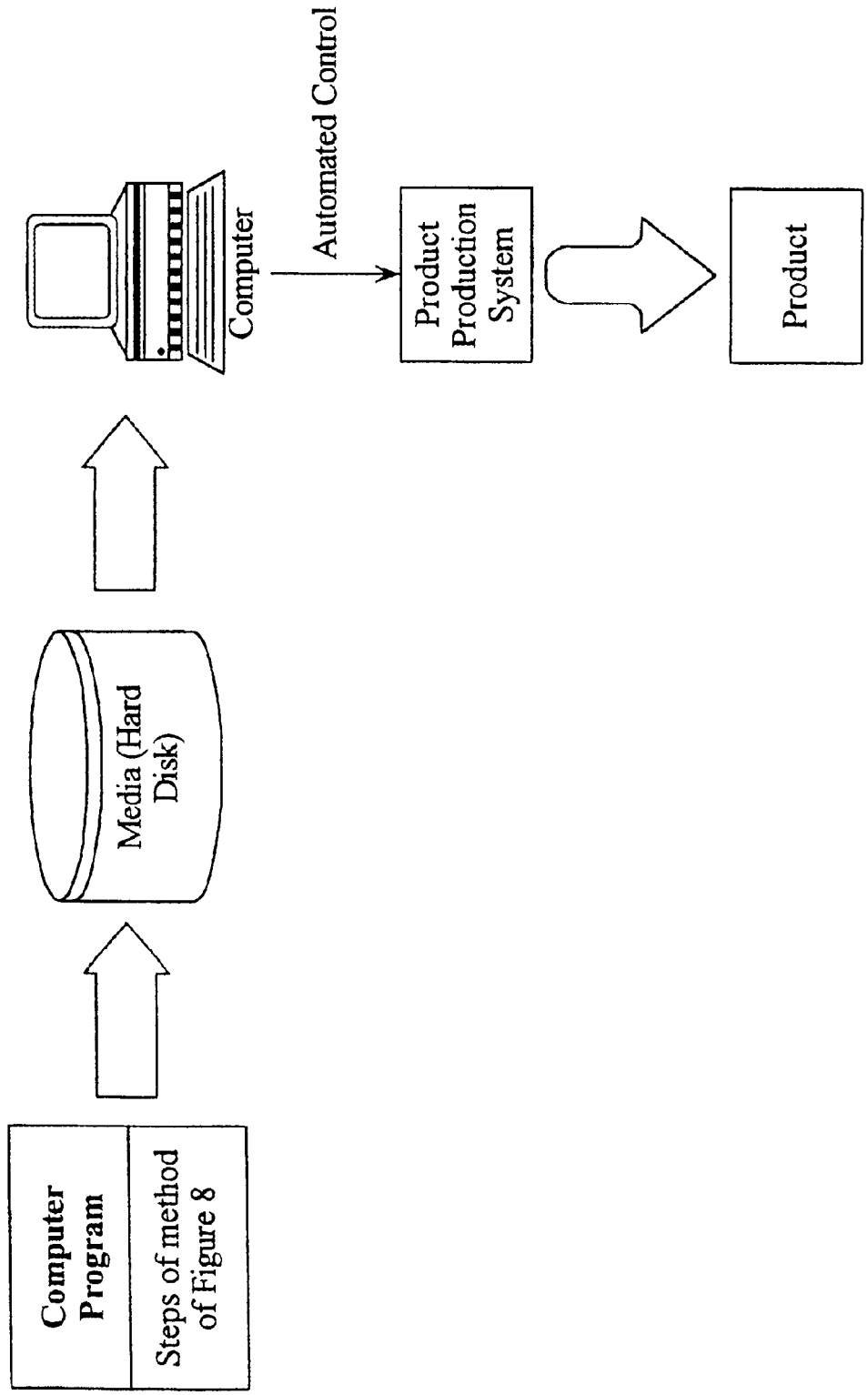
FIG. 9 is a schematic diagram of a system implementing the adapted program method of FIG. 8.

For example, the methods can be adapted to control a process for production of a product as shown in the general flow diagram of FIG. 8 and the schematic diagram of FIG. 9. This example can represent an automated sheet metal assembly plant. The methods could be applied to existing data set in order to discover correlation that indicate demand for one of the products from the plant will significantly decrease in the summer months due to cyclical variations, while demand for another product increases. A link to automated process control systems in the plant could reduce orders for the first product, while increasing orders for another. Many other examples will be evident to those skilled in the art, including variations to the actual structure of the products as a result of discovered correlations.

Figure 10:
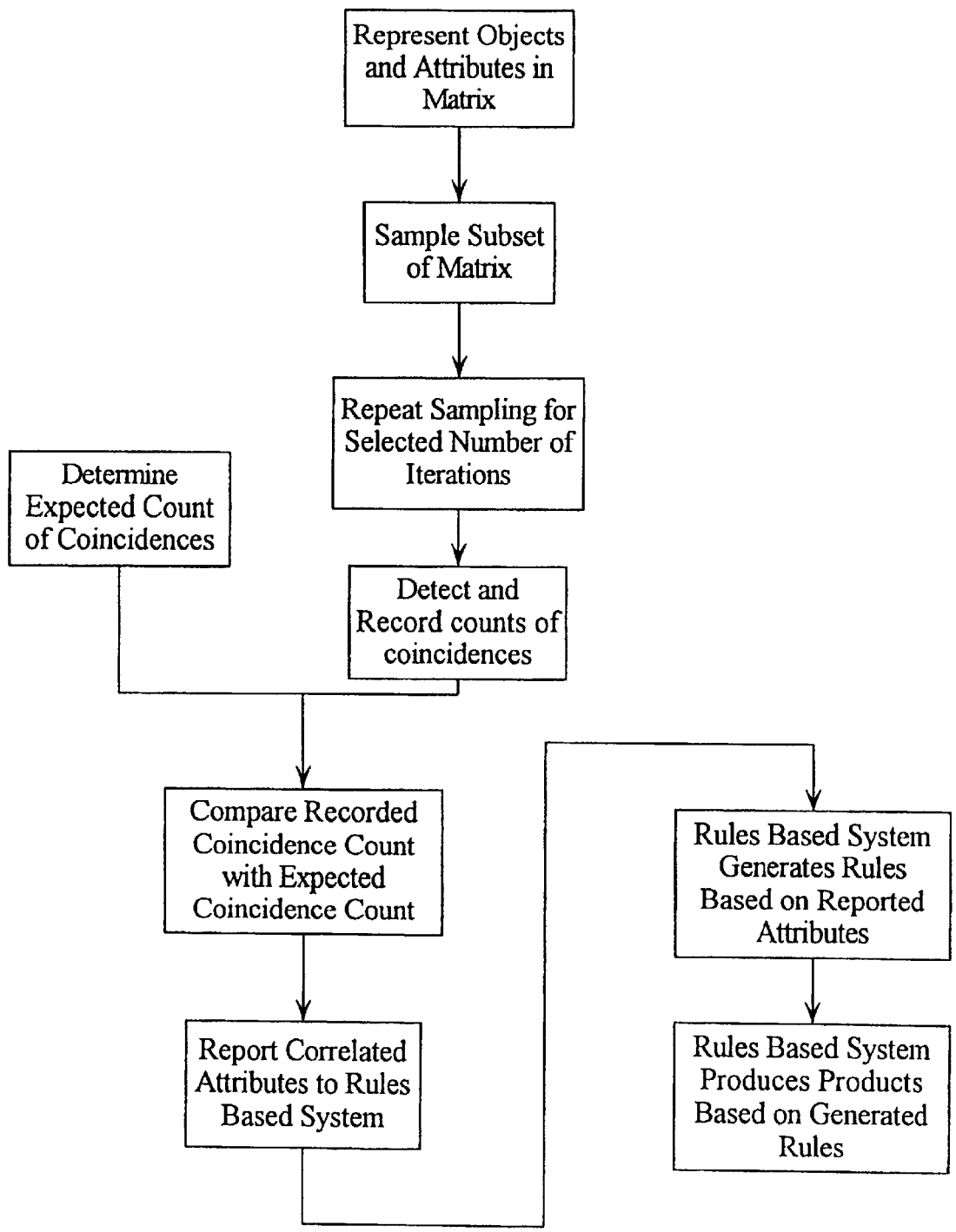
FIG. 10 is a general flow diagram of the program method of FIG. 6a adapted to generate rules for a rules based system that in turn produces a product.
Figure 11:
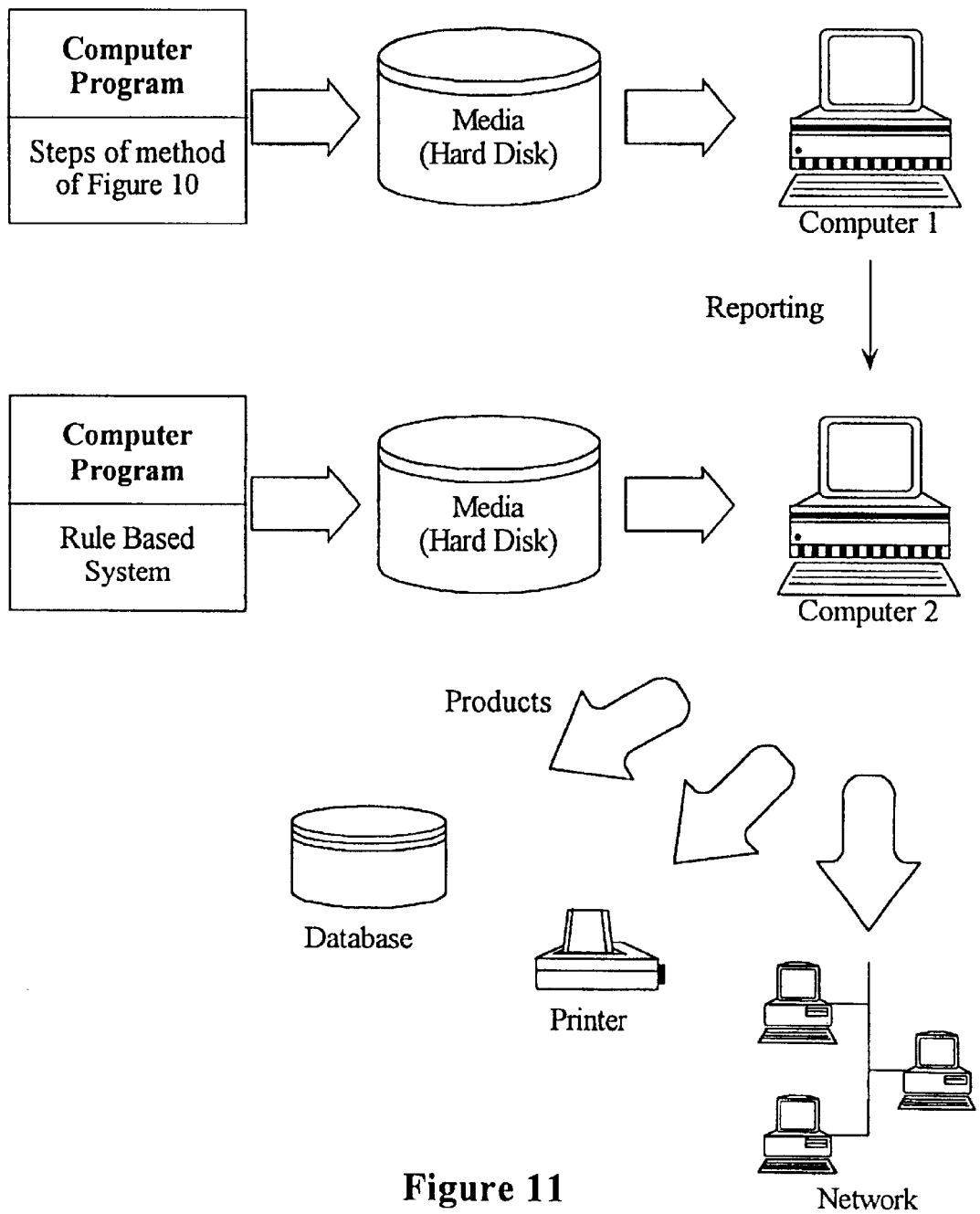
FIG. 11 is a schematic diagram of a system implementing the adapted program method of FIG. 10.

In an alternate embodiment, the discovered correlations may be used to generate rules for a rules based system that in turn produces products based upon those rules. A general flow diagram for such an embodiment is set out in FIG. 10. A corresponding schematic diagram is set out in FIG. 11.

Figure 12:
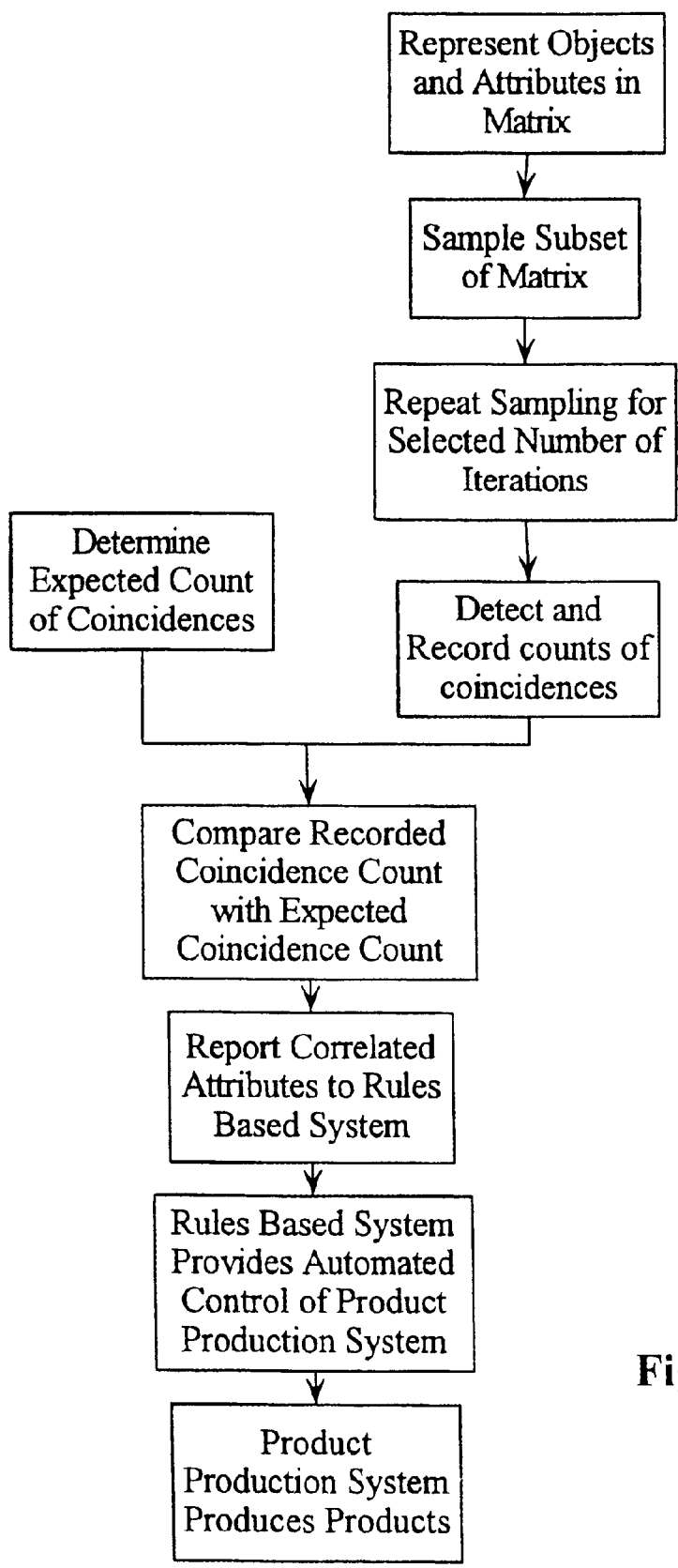
FIG. 12 is a general flow diagram of the program method of FIG. 6a adapted to generate rules used to control a process for production of a product.
Figure 13:
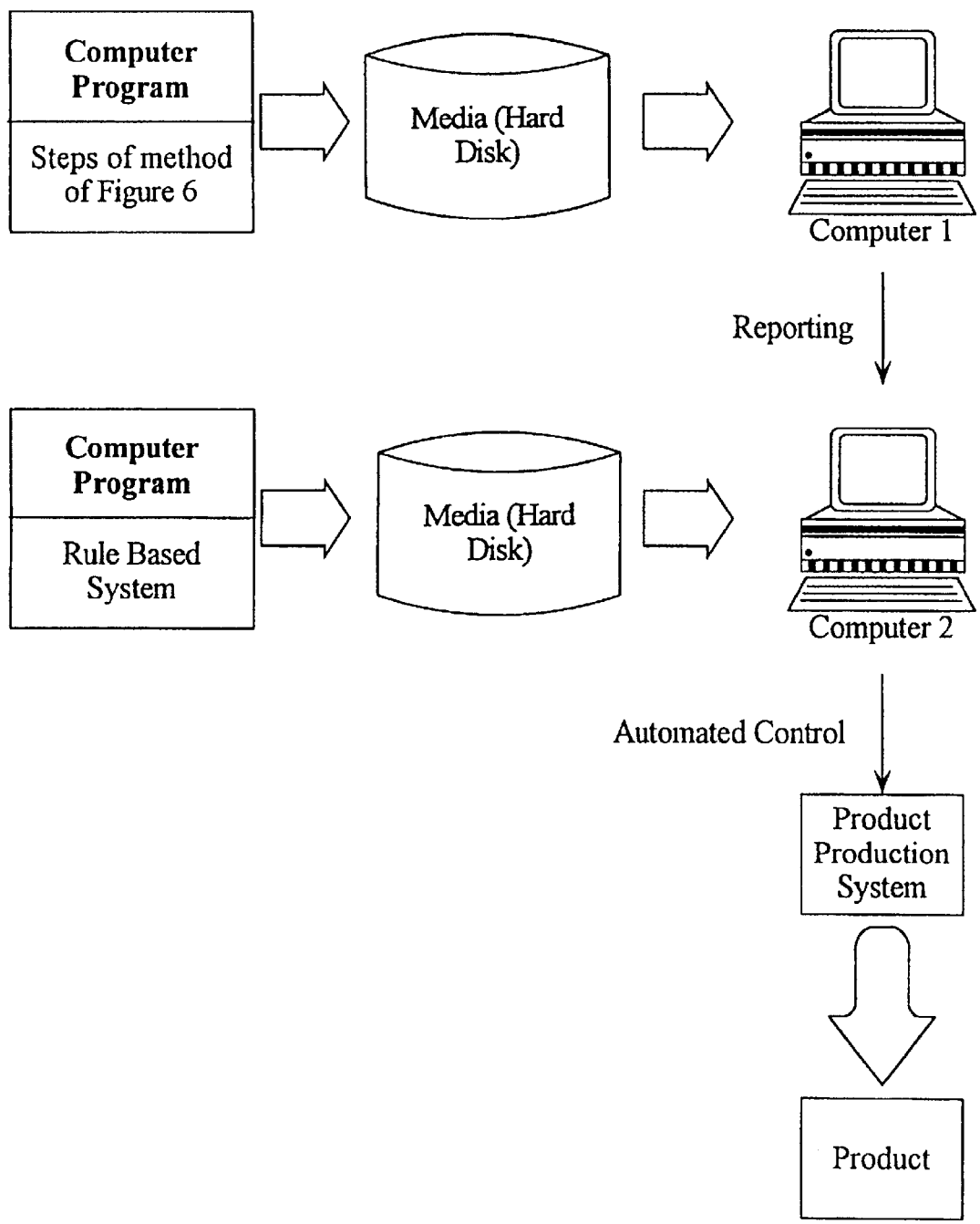
FIG. 13 is a schematic diagram of a system implementing the adapted program method of FIG. 12.

In a further alternate embodiment, the rules based system could be used to control a process that creates products. A general flow diagram for such an embodiment is set out in FIG. 12. A corresponding schematic diagram is set out in FIG. 13.

In application to financial analysis or trading, the objects can correspond to particular time slices or time periods, and the variables can relate to particular prices, or price changes, of particular financial instruments or commodities. By dividing the prices of each instrument or commodity into a set of discrete levels, or by using a simple binary code for "increase vs. decrease", one can represent each such instrument or commodity by a set of attributes, and the invention can be employed to discover k-tuples of instruments or commodities whose price movements are correlated. Those in the art know of many ways to gain value from such discovered information.

In applications to medicine, epidemiology, or environmental science, the objects can correspond to particular patients, or to different timed observations of a single patient, or samples from the same or different environmental resource (such as air, soil, or water); the variables and derived attributes would correspond to levels, or the presence/absence of particular symptoms, drugs, toxins or contaminants. In this way, one can use the present invention to discover interactions that may cause disease or environmental hazards.

In molecular and structural biological applications, the objects might correspond to DNA, RNA, or protein sequences and/or structures. The attributes might correspond to the presence of particular bases or amino acids at particular sequence positions, or to substructures with particular geometric, chemical, physical, or biological properties at particular sequence or structural positions, or to the presence or absence or levels of other global or local properties. For example, set out further below is a detailed application of the method to protein structure prediction, examples of which have previously been described..

In pharmacological applications, the object might correspond to molecular structures or other labels or representations of particular compounds or drugs, and the attributes might correspond to the presence, absence, or levels of particular geometric, chemical, physical, biological, toxicological, therapeutic and/or other properties and features, e.g., particular chemical moieties. The present method would be used to find correlations among k-tuples of such properties, and this information can be useful in the design and testing of compounds and drugs, and in the design of combinatorial libraries for screening and testing, or for other processes or steps in drug discovery and drug design. Alternatively, the above mapping can be transposed, so that the objects correspond to the properties and features, and the attributes correspond to the compounds and drugs. In this way, the present invention can be used to find sets of drugs with similar or complementary or synergistic or antagonistic activities. This, too, is extremely useful in drug discovery and drug design.

In applications to demographics, marketing, insurance and credit ratings, and/or fundraising, the objects can correspond to particular people, or companies, or organizations. The attributes could correspond to the presence or absence or levels of properties and features relating to employment, income, wealth, credit history, lifestyle, consumption patterns, or social/political opinions or affiliations. The present method could be used to discover associations between such factors, which can be useful in such tasks as predicting credit/insurance risks or detecting fraud; or in determining the best targets for allocating limited marketing or fundraising resources, for example.

The problem of finding all significant correlations among pairs or k-tuples of attributes in a database is ubiquitous in the computational sciences and in medical, industrial, and financial applications. The principles described herein include a probabilistic algorithm that has the interesting property of finding significant higher-order k-ary correlations, for all k such that $2 \leq k \leq N$ in an N-attribute database, for the same computational cost of finding just significant pairwise correlations. Moreover, k need not, be fixed in advance in our procedure, in contrast with other known procedures. The procedure was deigned for the task of finding conserved structural relationships in aligned protein sequences, but may have more useful application in other domains.

Application of the Principles Described Herein to Protein Sequence Analysis

There are interactions between sequence-distant amino acid residues in the protein chain, sometimes detectable as correlations between positions (columns) in a set of aligned sequences from a protein structural family, that play an important role in determining structure and function. Discovered correlations may represent an evolutionary history of compensatory mutations, and may provide useful features in models of protein structural/functional families, but are ignored or mishandled by most ML (machine learning) classification methods, in part because of the high computational complexity of searching for k-tuples of correlated positions.

In order to practice the invention on a matrix of biological sequences such as nucleotide or amino sequences, the different sequences are first optimally aligned for the purpose of comparison. A position in a first sequence is compared with a corresponding position in a second sequence. When the compared positions are occupied by the same nucleotide or amino acid, as the case may be, the two sequences are identical at that position. The degree of identity between two sequences is often expressed as a percentage representing the ratio of the number of matching (identical) positions in the two sequences to the total number of positions compared. Optimally aligning tow or more sequences generally involves maximizing the degree of sequence identity between them.

Several algorithms and computer programs are known to those of ordinary skill in the art for aligning sequences. These tools include the PILEUP program from the Genetics Computer Group (Madison, Wis.)package (version 8) using a modified version of the progressive alignment method of Feng and Doolittle [J. Mol. Evol. 25, 351 (1987)]; CLUSTAL X, freeware available from the European Molecular Biology Laboratory (EMBL), Heildelberg, Germany; and BLAST, freeware available from the National Institutes of Health (NIH), Bethesda, Md., BLAST-P is used for amino acid sequences; BLAST-N is used for nucleotide sequences and BLAST X is used for nucleic acid codon/amino acid translation.

Several kinds of useful information can be obtained from protein sequence family analysis.

First, there is information to be extracted at the level of individual sequences, in the form of joint symbol frequencies. It is well-known that an abnormally high observed frequency of a particular single-position pattern (e.g., "G occurs at residue number 3 in 98% of these sequences") can reveal an important physico-chemical constraint on secondary or tertiary structure. This is also true of surprisingly-frequent joint symbol occurrences (e.g., "G at position 3, L at position 5, and M at position 87 occurs much more often than would be predicted by the individual marginal frequencies"). Such long-distance co-occurrences might be especially indicative of tertiary constraints, because the designated positions may be nearby each other in the 3D structure to which all of the modelled sequences correspond. (This detection of "suspicious coincidences", as when $p(A, B) \gg p(A)p(B)$, is at the heart of pattern recognition and learning, as noted long ago by others).

Figure 15B:
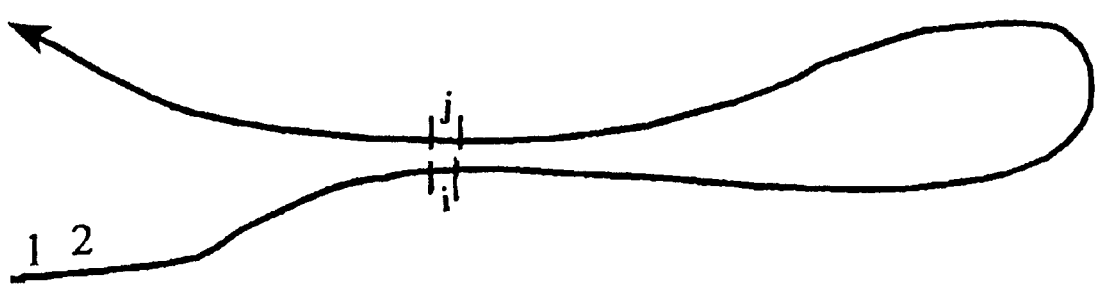
FIG. 15b is a diagram of a 3D structure for a sample protein.

Second, there is information to be extracted at the "next level up", of statistical relationships between the positions (columns in an alignment of homologous sequences). If the existence of frequently occurring joint symbol k-tuples can be used to infer 3D structural interactions, such an inference is even better supported by certain information-theoretic relationships between positions (columns) over a set of many different joint symbol occurrences. This is because such symbolic relationships can signify evolutionarily conserved physical or structural relationships between different parts of the protein chain. (See FIG. 15a). The observation of high values of mutual information and other correlation measures between columns has been used successfully to predict 3D structural interactions in RNA and in HIV proteins, for example, see C. E. Shannon and W. Weaver *The Mathematical Theory of Communication* The University of Illinois Press, 1964. While these previously reported efforts have focused on pairwise residue—residue interactions, the principles described herein, aim at the detection of k-ary interactions for $2 \leq k \leq N$.

Discovered k-tuples of correlated amino acid residues cane be used in protein structure prediction and structure determination.

Local predictions can help narrow the search for the best global structure predictions.

First, there are distance geometry constraints. Secondary structure prediction, and the discovery of k-ary long-distance interactions, give evidence for presumed contacts, of the form contact(i,j) for the ith and jth amino acid residues in a protein. Using the kind of distance geometry theory developed by others (see for example, T. F. Havel, L. D. Kuntz, G. M. Crippen *The Theory and Practice of Distance Geometry* Bull. of Mathematics Biology v. 45 1983 pp. 665–720. and K. A. Dill, K. M. Feibig, H. S. Chan *Cooperativity in Protein-Folding Kinetics* Proc. Natl. Acad. Sci. U.S.A. v. 90 March 1993 pp. 1942–1946), one can derive a set of inferred contacts. One can also derive sets of inferred blocks, contacts that are forbidden by a given set of presumed or inferred contacts. Essentially, given a model of a polymer chain constrained to exist within a fixed volume, the assumption that two particular pieces are brought into contact implies that some other pieces are also brought into proximity and that still other pieces are moved further apart. Indeed, others have concluded that "considerable amounts of internal architecture (helices and parallel and anti-parallel sheets) are predicted to arise in compact polymers due simply to steric restrictions. This appears to account for why there is so much internal organization in globular proteins."

Second, as discussed throughout the previous sections, one can infer and exploit empirical relationships between local and global configurations. Local stretches of sequence, or selected non-local pairs of residues, can be found to occur, with some high probability, in particular global configurations. Heuristic rules, in whatever form, can be used to avoid large parts of conformation space. This inference of particular models of cooperativity in folding is a special case: knowledge of "rules" such as $p(contact(i,j)|contact(i+1,j-1)) > p(contact(i,j))$ can help significantly.

Figure 16:
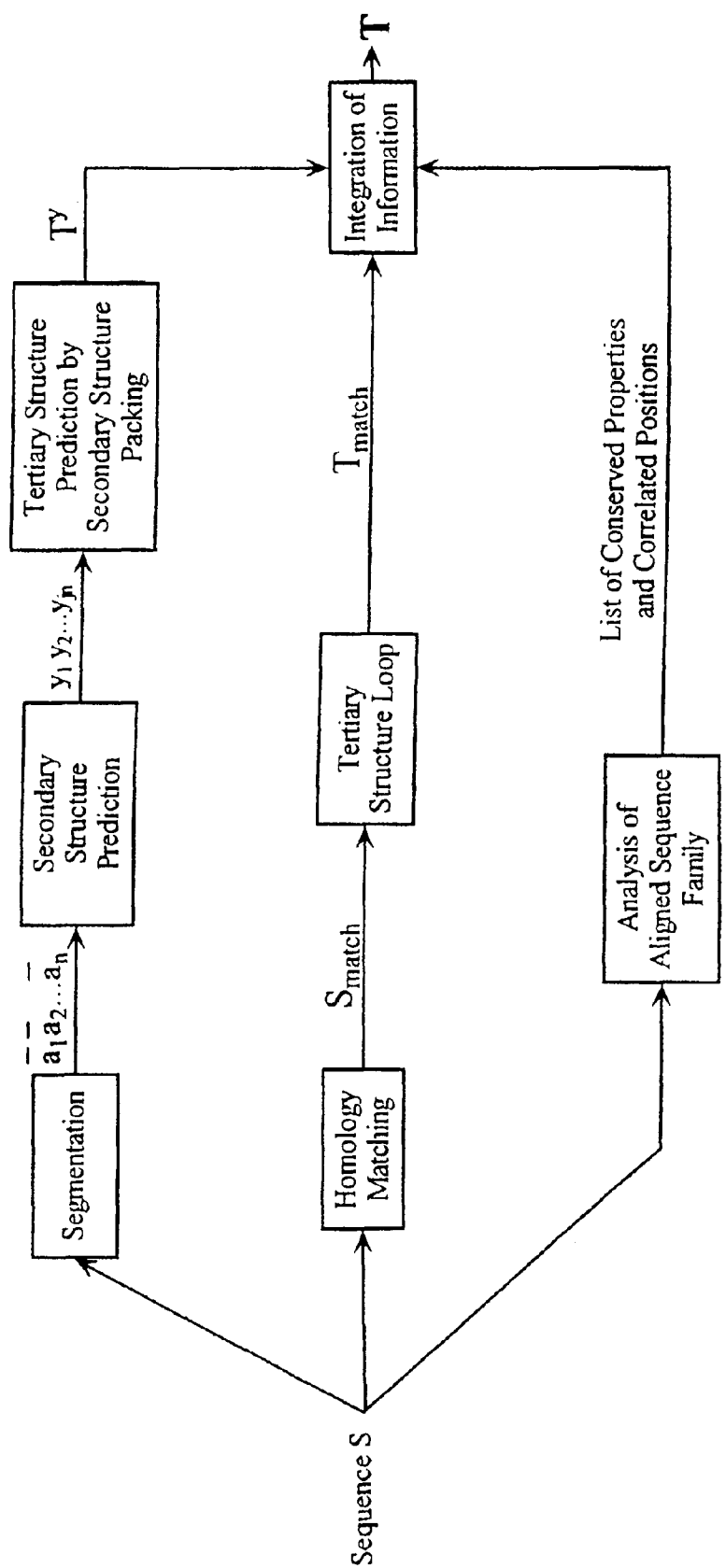
FIG. 16 is a diagram of steps in tertiary structure prediction which can employ the methods described herein.

For example, FIG. 16 illustrates steps in tertiary structure prediction. The methods described throughout this application can be applied as part of a larger tertiary structure prediction system, wherein the principles described above are employed in the block related to the analysis of aligned sequence families. The system predicts the structure of a protein.

Discovery of Evolutionarily-Conserved Structural Constraints

Three questions are addressed in this section:

1. What kinds of evolutionarily conserved multi-residue structural or functional constraints might one expect to find by detecting correlations between columns in a multiple sequence alignment?
2. Have correlation-detection efforts in face found important structural or functional constraints?
3. How much information do such discoveries provide towards predicting or determining a molecule's native tertiary structure?

What Do We Expect to Observe?

A protein family is the set of amino acid sequences that are believed to share a common global tertiary structure. The theory and observation of protein folding and evolution supports the general idea of evolution and conservation within a protein family:

Functional constraints are conserved in surface residues;
Structural constraints are conserved in core residues;
Mutational drift dominates in loop residues;
Functional constraints often involve other molecules—such as other proteins, nucleic acids, lipids, metals, $O_2$ or other small molecules.

The kind of structural constraints expected to be conserved throughout evolution of a protein family are mainly those involving a few key residues that stabilize a confirmation. Where electrostatic interactions are deemed important, one might expect to find a conservation of net charge across two or more sequence positions. When one of two electrostatically interacting residues carries a positive charge, its "partner" residue (presumably close in 3D structure even if distant in sequence) should be negatively charged, and vice versa. The situation is similar for packing constraints. One might reasonably expect sections of the protein core volume to vary only slightly across the many different proteins in the same structural family, while non-core regions might display large volume variability. Thus one might expect to find pairs or small k-tuples of residues that display mutually compensatory mutations with respect to side-chain volume—when a "Large" mutates to a "Small", another "Small" must mutate into a "Large", to put it simplistically.

What Has been Observed?

Neher et al. (How frequent are correlated changes in families of protein sequences PNAS, 91:98–102, 1994) attempted to quantify the frequency of compensatory changes within a single protein family by using physico-chemical property indices for amino acids and then estimating Pearsonian correlations between columns in an alignment. They attempted to get around the small-dataset problem with a bootstrap-inspired resampling scheme based on the examination of pairs of sequences from the family. Their study of the myoglobin family of protein sequences found the degree of compensatory mutation to be low for the property of side-chain volume but high for electrical charge—close to the correlation level expected for perfect conversation of local charge. The authors speculate that because their column-pair analyses focused only on contact-neighbour pairs of residues, they were able to detect a very locally-acting constraint like charge conservation but not a more distributed constraint like conservation of volume. (In other words, a single positively-charged residue must be in contact with its single negatively-charged structural partner, whereas a set of compatible-volume partners may comprise more than two residues and need not all be in contact). Others have also found some evidence of coordinated mutation in the evolution of protein structural families.

While most studies, to date, of compensatory mutation focus on highly-conserved "core"-type regions of protein structures, Korber et al. (Covariation of mutations in the V3 loop of HIV-1: An information-theoretic analysis. Proc. Nat. Acad. Sci, 90, 1993) analyzed the highly-variable V3 loop of the HIV-1 envelop protein. The researchers performed robust bootstrapped estimates of the pairwise mutual information for all column-pairs from a set of 31 columns, representing V3 residues. They found a set of about seven pais that showed considerable and statistically-significant mutual information, and their analysis of the particular attributes (amino acids) suggested a particular pattern of highly likely compensatory mutations. Although the authors did not argue or provide evidence for any particular properties or relationships being conserved, subsequent mutational analysis experiments in the laboratory indicated functional linkage between some of the pairs of sites with high mutual information. Because the V3 region is known to be both functionally and immunologically important, the inventor of the instant application suggested that such analyses might be important in the search for HIV/AIDS vaccine design.

What Kind of Method is Needed?

Clearly, several well-studies and effective methodologies exist for the comprehensive modelling of protein sequence families. In each case, the mathematical machinery is in place to handle and detect very local and low-order statistical structure in the data. In each case, the difficulties with computational complexity and statistical estimation arise in the attempt to account comprehensively for all possible non-local and higher-order interactions between residues, i.e., columns in the aligned sequence data.

Easier progress in modelling can be made if one is to use HMMs or density networks in conjunction with a fast, heuristic preprocessor that focuses explicitly on the detection of plausible non-local interactions while sacrificing a degree of precision in modelling these interactions. Such a procedure is provided by the principles described herein.

a) HIV PROTEIN SEQUENCE ANALYSIS

Tests on an HIV Protein Database

The Los Alamos HIV database contains, among other things, the amino acid sequences for the V3 loop region of the HIV envelope proteins. This region is known to have functional and immunological significance, and the discovery of sets of sites linked by evolutionary covariation might have important implications for understanding and preventing HIV infection and replication.

An earlier and smaller version of the same database was used by Los Alamos scientists in their analysis of pairwise mutual information between residues (columns).

Experiments were performed on an HIV dataset with the coincidence detection procedure, over a set of different values for r and T. Tables of results are shown and discussed below.

Results of Experiments on HIV Protein Database

The aforementioned version of the HIV-V3 dataset was edited in order to focus on the thirty-three residues considered most conserved and most structurally and functionally important by the Los Alamos researchers. The dataset therefore consisted of M=657 rows (sequences) of N=33 columns (residues). For the coincidence detection procedure, these 33 columns are transformed into $N_A N.\backslash A\backslash =33.21=693$ attributes. As with the artificial datasets, a set of experiments with different values of T and r were performed. Coincidence detection runs were done with T=10,000 and r=5, 6, 7, 10 respectively, and with T=100,000 and r=7, and finally with T=750,000 and r=7. The results are shown in tables C.1 through C.9 below.

Table C.1: The most likely correlated attributes, as estimated by the coincidence detection procedure, for the HIV dataset. These results were produced with parameter settings T=10,000 and r=5.

HIV Dataset.

T=10,000, r=5.

| Rank | CSET | Observed | Expected | Prob. |
|---|---|---|---|---|
| 1 | QI7\|D24 | 1012 | 632.553864 | 0.316056 |
| 2 | R17\|T21 | 901 | 610.770465 | 0.509734 |
| 3 | R12\|Q17 | 570 | 348.605833 | 0.675621 |
| 4 | L13\|W19\|Q24 | 195 | 5.535741 | 0.750381 |
| 5 | N4\|K9\|A21 | 226 | 74.167398 | 0.831582 |
| 6 | V11\|R12\|T18 | 159 | 20.764346 | 0.858239 |
| 7 | R12\|T18 | 454 | 318.517747 | 0.863429 |
| 8 | L13\|K31 | 419 | 300.333903 | 0.893461 |

Table C.2: The most likely correlated attributes, as estimated by the coincidence detection procedure, for the HIV dataset. These results were produced with parameter setting T=10,000 and r=6.

HIV Dataset.

T=10,000, r=6.

| Rank | CSET | Observed | Expected | Prob. |
|---|---|---|---|---|
| 1 | Q17\|D24 | 1177 | 385.853329 | 0.030891 |
| 2 | R17\|T21 | 957 | 368.736702 | 0.146238 |
| 3 | H12\|A18 | 1047 | 577.583832 | 0.294000 |
| 4 | S10\|D24 | 859 | 424.457490 | 0.350274 |
| 5 | R12\|Q17 | 656 | 224.743830 | 0.355855 |
| 6 | R12\|T18 | 628 | 283.191527 | 0.516585 |
| 7 | R17\|E24 | 563 | 234.477161 | 0.549033 |
| 8 | H12\|R17 | 760 | 434.274580 | 0.554644 |
| 9 | A18\|T21 | 560 | 315.973734 | 0.718330 |
| 10 | I11\|R17 | 861 | 627.014684 | 0.737741 |
| 11 | L13\|W19\|Q24 | 230 | 5.365202 | 0.755529 |
| 12 | A21\|D24 | 619 | 405.487239 | 0.776262 |
| 13 | N4\|K9\|A21 | 237 | 25.176801 | 0.779367 |
| 14 | V11\|R12\|T18 | 220 | 15.841474 | 0.793296 |
| 15 | L13\|K31 | 462 | 267.211446 | 0.809942 |
| 16 | G10\|H12 | 324 | 157.554658 | 0.857348 |
| 17 | M13\|W15 | 245 | 84.760597 | 0.867059 |
| 18 | Q17\|K31 | 384 | 231.749746 | 0.879169 |
| 19 | H12\|R17\|A18 | 147 | 8.219536 | 0.898526 |
| 20 | N4\|K9\|H33 | 309 | 170.353419 | 0.898711 |

Table C.3: The most likely correlated attributes, as estimated by the coincidence detection procedure, for the HIV dataset. These results were produced with parameter settings T=10,000 and r=7.

HIV Dataset.

T=10,000, r=7.

| Rank | CSET | Observed | Expected | Prob. |
|---|---|---|---|---|
| 1 | Q17\|D24 | 1312 | 228.829775 | 0.008322 |
| 2 | N4\|K9 | 2023 | 996.505631 | 0.013558 |
| 3 | H12\|A18 | 1175 | 328.263693 | 0.053591 |
| 4 | R17\|T21 | 940 | 216.431391 | 0.118015 |
| 5 | Q31\|H33 | 3198 | 2481.050915 | 0.122699 |
| 6 | R12\|T18 | 879 | 244.789294 | 0.193645 |
| 7 | S10\|D24 | 836 | 232.201517 | 0.225812 |
| 8 | R12\|Q17 | 720 | 140.866087 | 0.254370 |
| 9 | I11\|R17 | 808 | 360.719364 | 0.441944 |
| 10 | H12\|R17 | 659 | 253.717715 | 0.511691 |
| 11 | R17\|A118 | 720 | 361.819054 | 0.592356 |
| 12 | A21\|D24 | 554 | 236.085429 | 0.661974 |
| 13 | R17\|E24 | 452 | 138.843412 | 0.670137 |
| 14 | L13\|K31 | 537 | 231.137972 | 0.682602 |
| 15 | L13\|W19\|Q24 | 292 | 5.055474 | 0.714573 |
| 16 | A18\|T21 | 442 | 165.231990 | 0.731502 |
| 17 | A18\|Q31\|H33 | 480 | 209.122778 | 0.741198 |
| 18 | M13\|W15 | 355 | 88.975694 | 0.749122 |
| 19 | N4\|K9\|H33 | 340 | 75.556215 | 0.751690 |
| 20 | V11\|R12 | 513 | 253.001684 | 0.758878 |

Table C.4: The most likely correlated attributes, as estimated by the coincidence detection procedure, for the HIVE dataset. These results were produced with parameter settings T=10,000 and r=10.

HIV Dataset.

T=10,000, r=10.

| Rank | CSET | Observed | Expected | Prob. |
|---|---|---|---|---|
| 1 | Q31\|H33 | 3933 | 883.532458 | 0.000000 |
| 2 | N4\|K9 | 2898 | 251.248235 | 0.000001 |
| 3 | S10\|F19 | 2245 | 907.769718 | 0.027977 |
| 4 | F19\|G23 | 2660 | 1588.173503 | 0.100497 |
| 5 | R12\|T18 | 1155 | 142.229768 | 0.128554 |
| 6 | K9\|I11 | 1230 | 311.653160 | 0.185125 |
| 7 | A18\|H33 | 1720 | 990.576490 | 0.345032 |
| 8 | K9\|H33 | 1125 | 405.874883 | 0.355482 |
| 9 | H12\|A18 | 732 | 54.213558 | 0.399002 |
| 10 | S10\|G23 | 1492 | 856.152048 | 0.445479 |
| 11 | N4\|H33 | 1257 | 689.784961 | 0.525468 |
| 12 | A18\|Q31 | 1188 | 636.901303 | 0.544755 |
| 13 | Q17\|D24 | 571 | 42.938312 | 0.572525 |
| 14 | V11\|R12 | 670 | 143.659674 | 0.574607 |
| 15 | I11\|R17 | 562 | 61.788305 | 0.606274 |
| 16 | N4\|R17 | 992 | 498.586806 | 0.614520 |
| 17 | R12\|Q17 | 484 | 31.204991 | 0.663619 |
| 18 | K31\|Y33 | 578 | 130.131866 | 0.669535 |
| 19 | R17\|T21 | 479 | 39.372545 | 0.679400 |
| 20 | S10\|D24 | 451 | 34.199456 | 0.706491 |

Table C.5: The thirty most likely correlated attributes, as estimated by the coincidence detection procedure, for the HIV dataset. These results were produced with parameter settings T=100,000 and =7.

HIV Dataset.

T=100,000, r=7.

| Rank | CSET | Observed | Expected | Prob. |
|---|---|---|---|---|
| 1 | H12\|A18 | 11686 | 3282.636926 | 0.000000 |
| 2 | N4\|K9 | 21853 | 9965.056308 | 0.000000 |
| 3 | Q17\|D24 | 11585 | 2288.297747 | 0.000000 |
| 4 | Q31\|H33 | 31715 | 24810.509148 | 0.000000 |
| 5 | R17\|T21 | 9355 | 2164.313906 | 0.000000 |
| 6 | R12\|Q17 | 7259 | 1408.660868 | 0.000001 |
| 7 | R12\|T18 | 8380 | 2447.892936 | 0.000001 |
| 8 | S10\|D24 | 7666 | 2322.015166 | 0.000009 |
| 9 | I11\|R17 | 8336 | 3607.193645 | 0.000109 |
| 10 | A21\|D24 | 6342 | 2360.854285 | 0.001550 |
| 11 | H12\|R17 | 6363 | 2537.171146 | 0.002543 |
| 12 | R17\|A18 | 7162 | 3618.190543 | 0.005941 |
| 13 | R17\|E24 | 4451 | 1388.434119 | 0.021747 |
| 14 | A18\|T21 | 4673 | 1652.319901 | 0.024130 |
| 15 | V11\|R12 | 5486 | 2530.016841 | 0.028256 |
| 16 | L13\|K31 | 5224 | 2311.379719 | 0.031348 |
| 17 | N4\|K9\|H33 | 3519 | 755.562151 | 0.044291 |
| 18 | A18\|Q31\|H33 | 4665 | 2091.227775 | 0.066951 |
| 19 | L13\|W19\|Q24 | 2585 | 50.554739 | 0.072672 |
| 20 | R17\|Q31 | 5967 | 3574.032278 | 0.096592 |
| 21 | M13\|W15 | 3204 | 889.756945 | 0.112364 |
| 22 | V11\|R12\|T18 | 2424 | 117.500168 | 0.114017 |
| 23 | N4\|A21 | 6209 | 4030.321314 | 0.144077 |
| 24 | K31\|Y33 | 4878 | 2773.817984 | 0.164117 |
| 25 | Q17\|K31 | 3440 | 1450.098718 | 0.198651 |
| 26 | K9\|A21 | 5614 | 3692.671816 | 0.221632 |
| 27 | P19\|D24 | 3998 | 2250.071839 | 0.287354 |
| 28 | Q17\|A21 | 4151 | 2414.536189 | 0.292077 |
| 29 | G10\|H12 | 2661 | 953.572593 | 0.304245 |
| 30 | H12\|E24 | 3018 | 1458.576938 | 0.370622 |

Table C.6: The first twenty-five of the fifty most likely correlated attributes, as estimated by the coincidence detection procedure, for the HIV dataset. These results were produced with parameter settings T=750,000 and r=7. Note the appearance, at this degree of sampling, of several statistically significant higher-order features with $k \geq 3$.

HIV Dataset.

T=750,000, r=7.

| Rank | CSET | Observed | Expected | Prob. |
|---|---|---|---|---|
| 0 | A18\|Q31\|H33 | 36019 | 15684.208314 | 0.000000 |
| 1 | A18\|T21 | 33816 | 12392.399254 | 0.000000 |
| 2 | A21\|D24 | 45549 | 17706.407140 | 0.000000 |
| 3 | H12\|A18 | 86025 | 24619.776947 | 0.000000 |
| 4 | H12\|R17 | 48257 | 19028.783592 | 0.000000 |
| 5 | I11\|R17 | 64548 | 27053.952336 | 0.000000 |
| 6 | L13\|K31 | 39382 | 17335.347894 | 0.000000 |
| 7 | L13\|W19\|Q24 | 20184 | 379.160544 | 0.000000 |
| 8 | M13\|W15 | 23300 | 6673.177096 | 0.000000 |
| 9 | N4\|K9 | 162152 | 74737.922307 | 0.000000 |
| 10 | N4\|K9\|H33 | 26376 | 5666.716129 | 0.000000 |
| 11 | Q17\|D24 | 86891 | 17162.233105 | 0.000000 |
| 12 | Q31\|H33 | 2331901 | 86078.318611 | 0.000000 |
| 13 | R12\|Q17 | 53740 | 10564.956512 | 0.000000 |
| 14 | R12\|T18 | 62774 | 18359.197022 | 0.000000 |
| 15 | R17\|A18 | 54366 | 27136.429076 | 0.000000 |
| 16 | R17\|E24 | 33748 | 10413.255892 | 0.000000 |
| 17 | R17\|Q31 | 45065 | 26805.242087 | 0.000000 |
| 18 | R17\|T21 | 70301 | 16232.354294 | 0.000000 |
| 19 | S10\|D24 | 57772 | 17415.113746 | 0.000000 |
| 20 | V11\|R12 | 39546 | 18975.126308 | 0.000000 |
| 21 | V11\|R12\|T18 | 17628 | 881.251263 | 0.000000 |
| 22 | K31\|Y33 | 36346 | 20803.634880 | 0.000002 |
| 23 | N4\|A21 | 45441 | 30227.409858 | 0.000003 |
| 24 | Q17\|K31 | 25033 | 10875.740384 | 0.000018 |
| 25 | G10\|H12 | 20779 | 7151.794446 | 0.000041 |

Table C.7: Continuation of the fifty most likely correlated attributes, as estimated by the coincidence detection procedure, for the HIV dataset: csets ranked 26 through 50. These results were produced with parameter settings T=750,000 and r=7. Note the appearance, at this degree of sampling, of several statistically significant higher-order features with $k \geq 3$.

HIV Dataset.

T=750,000, r=7.

| Rank | CSET | Observed | Expected | Prob. |
|---|---|---|---|---|
| 26 | K9\|A21 | 40098 | 27695.038620 | 0.000231 |
| 27 | F19\|D24 | 29121 | 16875.538795 | 0.000286 |
| 28 | Q17\|A21 | 29621 | 18109.021417 | 0.000737 |
| 29 | H12\|E24 | 22348 | 10939.327036 | 0.000839 |
| 30 | N4\|K9\|I11 | 15175 | 4159.316971 | 0.001355 |
| 31 | S4\|T9\|T12\|V18\|R21 | 10919 | 1.718549 | 0.001524 |
| 32 | N4\|K9\|A21 | 11233 | 623.181959 | 0.002185 |
| 33 | N4\|Q31\|H33 | 21868 | 11328.342993 | 0.002369 |
| 34 | F19\|A21 | 44400 | 34516.144368 | 0.004910 |
| 35 | K9\|Q31\|H33 | 16593 | 6991.723718 | 0.006625 |
| 36 | W19\|Q24 | 16738 | 7234.038664 | 0.007331 |
| 37 | E1\|N12 | 10844 | 1492.835945 | 0.008575 |
| 38 | K9\|E24 | 13847 | 4587.312260 | 0.009408 |
| 39 | K9\|R17 | 33735 | 24568.179150 | 0.010326 |
| 40 | T12\|V18 | 23076 | 14893.617567 | 0.026158 |
| 41 | R12\|A21 | 15497 | 7516.155896 | 0.031231 |
| 42 | N4\|K9\|Q31\|H33 | 8280 | 493.681367 | 0.036905 |
| 43 | N4\|K9\|A18 | 11655 | 4250.900600 | 0.050618 |
| 44 | S4\|T9\|T12\|V18\|R21\|Y33 | 7370 | 0.093039 | 0.052029 |
| 45 | R12\|Q17\|T18 | 7452 | 240.364918 | 0.058992 |
| 46 | V11\|Q17 | 14350 | 7329.962834 | 0.068429 |
| 47 | H12\|T21 | 23263 | 16324.923094 | 0.072825 |
| 48 | Q17\|Y33 | 17288 | 10374.788061 | 0.074203 |
| 49 | L13\|W19 | 15536 | 8921.243955 | 0.092437 |
| 50 | S17\|H28 | 6529 | 138.997153 | 0.108375 |

Table C.8: The top thirty-five pairwise inter-column mutual information values for the HIV-V3 dataset, as estimated by our methodology as described in the main text.

| Rank | Pair i, j | MI ($c_i$, $c_j$) | Std. Error |
|---|---|---|---|
| 1 | 12\|18 | 0.340449 | 0.037792 |
| 2 | 4\|9 | 0.337943 | 0.0389162 |
| 3 | 9\|21 | 0.319481 | 0.0353829 |
| 4 | 23\|24 | 0.315202 | 0.0337213 |
| 5 | 12\|24 | 0.314393 | 0.0330382 |
| 6 | 9\|24 | 0.313992 | 0.0344732 |
| 7 | 19\|24 | 0.305609 | 0.0335857 |
| 8 | 11\|24 | 0.297498 | 0.0358645 |
| 9 | 24\|26 | 0.290044 | 0.0384839 |
| 10 | 9\|11 | 0.289911 | 0.0344244 |
| 11 | 9\|23 | 0.285019 | 0.0343224 |
| 12 | 4\|21 | 0.284936 | 0.0332236 |
| 13 | 18\|21 | 0.278151 | 0.0404634 |
| 14 | 4\|11 | 0.277189 | 0.0353993 |
| 15 | 12\|21 | 0.273137 | 0.033385 |
| 16 | 4\|24 | 0.262226 | 0.036189 |
| 17 | 21\|24 | 0.260366 | 0.0338395 |
| 18 | 11\|23 | 0.260337 | 0.0323302 |
| 19 | 11\|19 | 0.249877 | 0.0320634 |
| 20 | 10\|24 | 0.248938 | 0.0325318 |
| 21 | 19\|23 | 0.242185 | 0.032301 |
| 22 | 5\|26 | 0.239395 | 0.0386373 |
| 23 | 9\|19 | 0.238318 | 0.0331283 |
| 24 | 4\|23 | 0.23359 | 0.0302795 |
| 25 | 24\|25 | 0.222109 | 0.0358744 |
| 26 | 6\|26 | 0.220371 | 0.0397722 |
| 27 | 4\|26 | 0.220213 | 0.0333324 |
| 28 | 6\|24 | 0.218815 | 0.0335123 |
| 29 | 9\|12 | 0.214844 | 0.0280984 |
| 30 | 15\|24 | 0.213921 | 0.0301834 |
| 31 | 10\|12 | 0.2133 | 0.0306496 |
| 32 | 9\|18 | 0.21078 | 0.031734 |
| 33 | 11\|21 | 0.210155 | 0.0308121 |
| 34 | 11\|12 | 0.209421 | 0.0294066 |
| 35 | 4\|19 | 0.20911 | 0.0290533 |

Table C.9: The top seven pairwise inter-column mutual information values for the HIV-V3 dataset, as estimated by the Los Alamos group.

| Rank | Pair i, j |
|---|---|
| 1 | 23\|24 |
| 2 | 12\|24 |
| 3 | 12\|18 |
| 4 | 12\|23 |
| 5 | 19\|24 |
| 6 | 10\|24 |
| 7 | 10\|12 |

Tables C.1 through C.4 illustrate the most significant csets (again measured by our procedure's estimation of P(Observed\Independence) for the Observed number of coincidences for each detected coincidence of attributes. As one might expect, a clean separation between "probably correlated" and "probably uncorrelated" does not manifest itself at this comparatively low degree of sampling for this real-world dataset. Results for r=7 and r=10 indicate more significant discovered csets than those for r=5 and r=6. At these former, higher r values, one sees the emergence of a few csets with "Prob" values less than 0.1: (Q@17, D@24,), (N@4, K@9), (H@12, A@18), (Q@31, H@23) and (S@10, F@19). All of these csets appear among the most significant csets reported in the more intensive sampling runs (with T=100,000 and T=750,000), with the notable exception of (S@10, F@19). This latter cset is discovered at this low degree of sampling only in the r=10 run, and does not appear in the more intensive sampling runs shown, both of which used r=7.

Table C.5 displays the results for T=100,000 and r=7, and here it is clear that some separation of signal from noise is taking place amongst the set of HOFs, with seventeen pairwise and three 3-ary correlations appearing within our Prob≦0.1 significance level.

At T=750,000, we have more statistically significant detection of almost fifty 2-ary, 3-ary and up through 6-ary attribute correlations, as shown in Tables C.6 and C.7.

In order to get a better sense of the possible meanings of these results, let us consider these inter-attribute correlations along with some inter-column correlations in the form of pairwise mutual information estimates performed in our own analysis and also by the Los Alamos group. Table C.8 displays the highest estimated mutual information values amongst all N—N=528 pairs of columns from our 33-column dataset. The estimates were obtained using a Bootstrap-like procedure in which 1000 sample data subsets of m=300 out of M=657 were drawn and run though the standard mutual information calculation. Reported in the table are therefore the mean values over the resampling and the associated standard error values. There is significant intersection between the set of column-pairs indicated by the top cset values in Tables C.6 and C.7 and those indicated by the top mutual information values in Table C.8. The correspondence between the two rankings is not perfect, for a few reasons (besides noise and simple sampling error). First and foremost, while the "suspiciousness" of a single joint-attribute combination certainly contributes to the mutual information within the corresponding set of columns the behaviour of the other symbols appearing within the columns obviously also can have great effect. Second, we note again the observed sensitivity coincidence detection results to the choice of r.

Table C.9 lists the highest statistically significant mutual information values as estimated by the Los Alamos group. We note the overlap between their list and ours, but we emphasize again that group's use of an earlier, smaller, and perhaps otherwise different database to which we did not have access.

Application of the coincidence detection method of the invention to biological data such as these aligned HIV sequences thus leads to identification of covarying structural elements that were previously unrecognized. The statistically significant coincidence of particular structural elements, such as amino acid residues, likely indicates a biological role for a motif comprising the covarying elements, as structure and function are tightly linked in biochemical systems. One such example from the above application of the invention is the statistically significant coincidence of residues A18, Q31 and H33 in the V3 loop of HIV envelope protein. These residues are expected to contribute to a structural motif of the V3 loop that plays a biological role in the HIV life cycle. Such new information about A18/Q31/H33, which prior to the invention have never before been grouped together for a particular biological role, may be exploited in various ways, as follows.

A peptide or peptidomimetic mimicking the aforementioned structural motif of the V3 loop (or another protein motif identified by the coincidence detection method) is provided by the invention. For the chosen example, the peptide or peptidomimetic would include spatial coordinates of amino acid residues A18/A31/H33, though every atom of these amino acids would not necessarily be required. Rather, the peptide or peptidomimetic would have such spatial coordinates of A18/Q31/H33, as well as topological and electrostatic attributes, that would make it useful for a biological function, such as, for example competing with the actual V3 loop of HIV for binding to another biological molecule, where such binding of V3 would employ the structural motif that is mimicked by the peptide or peptidomimetic.

Alternatively, a peptide or peptidomimetic which is designed based on covarying k-tuples discovered by the coincidence detection method could be used as an antigen. That is, the biological function which the molecule mimics is eliciting an immune response in an animal. Similarly, vaccines embodying the covarying k-tuples described herein are also encompassed by the invention.

Morgan and co-workers (Morgan et al. 1989. In Annual Reports in Medicinal Chemistry. Ed.: Vinick, J. J. Academic Press, San Diego, Calif., pp. 243–252.) define peptide mimetics as "structures which serve as appropriate substitutes for peptides in interactions with receptors and enzymes. The mimetic must possess not only affinity but also efficacy and substrate function." For purposes of this disclosure, the terms "peptide mimetic" and "peptidomimetic" are used interchangeably according to the above excerpted definition. That is, a peptidomimetic exhibits function(s) of a particular peptide, without restriction of structure. Peptidomimetics of the invention, e.g., analogues of the structural motif of the V3 loop posited above, may include amino acid residues or other chemical moieties which provide the desired functional characteristics.

The invention further provides a ligand that interacts with a protein having a structural motif identified using the coincidence detection method of the invention, as well as a pharmaceutical composition including the ligand and a pharmaceutically acceptable carrier or exicipient therefor. The ligand would include chemical moieties of suitable identity and spatially located relative to each other so that the moieties interact with corresponding residues or portions of the motif. By interacting with the motif, the ligand could interfere with function of that region of the protein including the motif.

Thus, the invention provides a pharmaceutical composition for interacting with an envelope protein of human immunodeficiency virus (HIV), including a ligand having a functional group that interacts with the structural motif of the V3 loop which has spatial coordinates of residues A18/Q31/H33, and a pharmaceutically acceptable carrier or exicipient therefor. The ligand may have more than one functional group that interacts with the motif, such as, for example, a first functional group capable of binding to and being present in an effective position in the ligand to bind to residue 18, a second functional group capable of binding to and being present in an effective position in the ligand to bind to residue 31, and a third functional group capable of binding to and being present in an effective position in said ligand to bind to residue 33.

The invention further provides a method of designing a ligand to interact with a structural motif of an protein, such as, for example, envelope protein of human immunodeficiency virus (HIV). For example, in the case where the motif is the potentially interesting A18/Q31/H33 motif identified by the coincidence detection method discussed above, the method of designing includes the steps of providing a template having spatial coordinates of residues A18, Q31 and H33 in the V3 loop of HIV envelope protein, and computationally evolving a chemical ligand using an effective algorithm with spatial constraints, so that the evolved ligand includes at least one effective functional group that binds to the motif. The template provided may further include topological and/or electrostatic attributes, and the effective algorithm include topological and/or electrostatic constraints. Similar method steps would be employed for other proteins comprising a motif identified by the coincidence detection method.

The invention further provides a method of identifying a ligand to bind with a structural motif of a protein. The structural motif is preferably identified by the coincidence detection method. For example, in the case where the motif is that identified by the coincidence detection method comprising residues A18, Q31 and H33 of HIV envelope protein discussed above, the method includes the steps of: providing a template having spatial coordinates of A18, Q31 and H33 in the V3 loop HIV envelope protein, providing a data base containing structure and orientation of molecules, and screening the molecules in the data base to determine if they contain effective moieties spaced relative to each other so that the moieties interact with the motif. The data base may further contain topological and/or electrostatic attributes of the molecules, and the screening step further include determining if the moieties are effective in such regard for interacting with the motif. For example, a molecule described in the data base may have such physical/chemical attributes that it includes a first moiety that interacts with residue 18, a second moiety that interacts with residue 31 and a third moiety that interacts with residue 33. Similar method steps would be employed for other proteins comprising a structural motif of interest.

Where a ligand provided by the invention is included in a pharmaceutical composition, the pharmaceutical composition further includes a pharmaceutically acceptable carrier as in known to persons skilled in the art relating to pharmaceutical compositions. The term "pharmaceutically acceptable carrier" as used herein include diluents such as saline and aqueous buffer solutions and vehicles of solid, liquid or gas phase, as well as carriers such as liposomes (Strejan et al. 1984, *J. Neuroimmunol* 7:27), and dispersing agents such as glycerol, liquid polyethylene glycols, and the like. The pharmaceutical composition may include any of the solvents, dispersion media, coatings, stability enhancers, antibacterial and antifungal agents (for example, parabens, chlorobutanol, phenol, ascorbic acid, thimerosal), isotonic agents (for example, sodium chloride, sugars, polyalcohols such as mannitol) and absorption delaying agents (for example, aluminum monostearate and gelatin) which are known in the art.

Alternatively, a ligand provided by the invention, such as a ligand which binds to a biological target, may be employed for diagnostic purposes. A diagnostic agent according to the invention may include a ligand that interacts with a protein having a structural motif identified using the coincidence detection method, and a detectable label linked to the ligand. The detectable label may be any detectable substance known in the art, such as, for example, a fluorescent substance or a radioactive substance. Alternatively, the label may be an enzyme (such as, for example, horseradish peroxidase or alkaline phosphatase) which catalyzes a reaction having a detectable (e.g., colored) product, or the label may be the substrate for such an enzyme.

Application of the Principles Described to Drug Discovery Background

The multi-billion dollar pharmaceutical industry is based in large part on the design or discovery and refinement of small molecules ("ligands") that interact with larger molecules ("targets") and in some way repress, enhance, block, accelerate or otherwise modify the structure, function or activity of the target. It is the structure, function or activity of the target that is in some way implicated in some mechanism of disease. The target molecule is often an enzyme or protein receptor or nucleic acid or some combination thereof. There are a great number of possible ligands and only some relatively very few of them are developed and marketed as therapeutic compounds that work with or against some one or more targets and thus are effective against disease.

It is therefore of great interest to biotechnology and pharmaceutical researchers to be able to consider a huge number of potentially useful compounds, but to avoid spending too many resources developing therapies based on compounds that may turn out not to be useful, safe, effective, and economically viable. The methods described herein can be used to enhance and accelerate the process of discovering good, effective compounds and of distinguishing the promising compounds from the unpromising or less promising compounds in a public or private collection of molecules or their computer database representations. They can be used effectively and contribute value in this application in many ways, by helping to understand and infer target structures and by finding ligands whose geometric, topological, electrostatic or other features make them likely candidates for effective interaction with the targets.

Application of the Principles Described Herein to Databases of Molecules and their Features One way to represent a large number of molecular structures within a computer database (whether stored in main memory, on magnetic disk, tape, or other electronic or optical media) is in terms of "screens". Persons skilled in the art will recognize screens as binary attributes wherein a given screen, or attribute, represents the presence or absence of a particular substructure pattern, for example, sulfate group. If a set of compounds is represented with screens, then a particular compound, which we will denote by C, can be represented by a string of 1s and 0s wherein the 1s stand for those pre-defined substructure patterns that C contains and the 0s stand for those of the pre-defined substructure patterns that C does not contain.

This scheme can be extended to the representation of the primary structure of a nucleic acid or protein in terms of attributes, as discussed elsewhere herein. The primary structure is also known as the "sequence", that is, a sequence of bases, or nucleotides, in DNA or RNA, and a sequence of amino acids, also called amino acid residues, in a protein. It is simple to represent a protein sequence, for example, as a sequence of symbols, each symbol being a letter of the alphabet corresponding to one of the twenty standard naturally-occurring amino acids. It is also simple to transform this representation by representing each residue, or position, in the sequence by a set of twenty binary attributes, if such a representation is desired. The attributes act like the screens described above. For example, if the first amino acid in protein P is an alanine, represented by A, it can also be represented by a value of "1" in the attribute that stands for the question, "Is the amino acid in position 1 an alanine?", and by values of "0" for the attributes representing "Is the amino acid in position 1 a cysteine?", "Is it a phenylalanine?", and so on. FIG. 15*a* provides an illustration of amino acid and residues positions.

It is also easy and sensible to represent other aspects or features of the compounds in terms of attributes. For example, a given compound C may be known to be active against a particular target T, in which case an attribute corresponding to the question "Active against T?" would have value 1 for the object corresponding to compound C. For another example, a pharmaceutical company may have run a number of compounds through a set of "assays", or tests of biological or chemical activity. An assay might test for some aspect of effectiveness against a target, or for ability to cross the blood-brain barrier, or for toxicity, for example. Assay results can be represented in terms of discrete-valued, and even binary attributes as well, via preprocessing routines known to persons in the art. Other features of particular compounds can include literature citations (that is, references to papers or studies in which the compound was described, designed, discovered or analyzed), and ownership or patent status of the compound.

Not only can small therapeutic compounds be represented in terms of screens and other attributes, but so can larger potentially therapeutic molecules such as DNA, RNA, peptides, proteins, carbohydrates and lipids. Target molecules can also be represented in this way. All that is required is a predefined (though possibly updated, changing, shrinking or growing) list of substructural patterns or other features deemed important by the researchers or users. For target structures, one might want to represent substructural patterns as well as their 1-dimensional linear structures ("sequence"), genetic linkage information, interactions with other proteins in disease pathways, literature citations, and so on. Sometimes a particular molecule might be listed as more than one object in a database, the different objects representing different conformations that the molecule can take.

Clearly, this use of screens and other attributes in representing compound databases can also be represented in terms of the M by N data matrix we have used to describe the working of the invention. The M by N data matrix is illustrated below in Table 1.

The rows in Table 1 correspond to a set of molecules, compounds, molecular structures or sequences, while the columns correspond to features that may include substructural patterns, assay results or other aspects of the molecules. The value in table cell[i,j] is one (1) if molecule i has feature j and is zero (0) otherwise.

TABLE 1

|  | Feature 1 | Feature 2 | ... | Feature N |
|---|---|---|---|---|
| Molecule 1 | 1 | 0 | ... | 1 |
| Molecule 2 | 0 | 1 | ... | 0 |
| ... | ... | ... | ... | ... |
| Molecule M | 0 | 0 | ... | 1 |

Steps involved in applying the methods described herein to the analysis of a molecular database include:

1. Obtain molecular database that supports discrete attribute representation for the 1D, 2D and/or 3D molecular structures of interest (or, obtain molecular database and use standard methods to produce such a representation); also use standard methods to transform sequence and other information about molecules of interest into attribute representations.
2. Present this database, in whole or part, to an embodiment of the current invention such that each compound in the database corresponds to one or more of the M objects (rows) in the embodiment's data matrix and so that each screen-represented substructure pattern corresponds to an attribute (column) of the data matrix. The additional attributes representing activity, assay results, known targets against which the compound has been used, source or means of production or storage of the compound, ownership or patent status of the compound, and so on, plus the substructure pattern attributes together comprise the N attributes (columns) in the data matrix.
3. Employ the base method above or one of the other embodiments described herein on the data matrix.
4. Direct the discovered correlated k-tuples of attributes to:
   A graphical viewer, or
   A rule-generator preprocessor for rule-based system, or
   A report for users, researchers or managers, or a report-generation system, or
   Another computer program that performs some kind of further analysis of the compounds, sequences, or structures represented in the database, or
   Another computer program that performs some transformation or optimization on the database, or
   Another computer program that directs humans and/or robots in drug screening experiments or in design, refinement or production of therapeutic compounds.

The output of the current invention, in this drug discovery application, can be useful in many possible ways.

First, it can be used in setting up or optimizing a screen-based representation of molecules. For example, it is known in the art that a good screen-based representation should use a set of screens (attributes) that are mutually uncorrelated and roughly equiprobable. The method of the current invention would produce, when used as described above, sets of correlated screens; this information can be used to add, remove, or combine the features that the screens represent, in order to make the modified set of screens closer to the ideal of uncorrelated and equiprobable.

Other useful and valuable aspects of the information produced by the method include the following.

For example, it is not uncommon for a pharmaceutical company to have good "lead compounds" that work in in vivo or in vitro experiments even when the researchers do not know the target structure, the active site on the target structure, or even which of several proteins in the biological system is the target. If the methods described herein are used to discover correlations among substructural patterns and assay results, this information can aid in inferring a target structure and designing even more effective lead compounds, because it allows researchers to associate structure with desired activity.

Another example is that of finding correlated amino acid residues in that part of a drug discovery database corresponding to an aligned set of DNA, RNA or protein sequences, as discussed later herein. In this case, some of the correlated k-tuples of residues (positions) may correspond to evolutionarily conserved structural and functional relationships. Therefore the principles described herein can in this way be used to help predict or solve the structure and function of important biological macromolecules, including pharmaceutical targets such as receptors and enzymes.

Another example is to find correlations between structural, functional, disease pathway or other aspects of one target molecule, T1, and another target molecule, T2; or finding correlations between structural, functional or other aspects of a set of potential therapeutic compounds aimed at T1 and those of a set of potential therapeutic compounds aimed at T2. In either case, this correlation information is useful because it allows drug designers to apply knowledge, compounds and techniques effective against T1 to the effort against T2.

Another rather different application of the principles described herein to drug discovery and medical science is obtained by considering the transpose of data matrix described above. Instead of compounds as objects (rows) and features of the compounds as attributes (columns), consider what is possible when the compounds correspond to columns and their features correspond to rows. See Table 2 below. Use of the current invention in this scenario produces correlated k-tuples of compounds in feature-space. These produced k-tuples can embody several kinds of valuable information. For example, if the features in the rows represent mostly substructural patterns (screens), then the produced k-tuples correspond to clusters of compounds. Such clustering of compound databases is very useful in high-throughput screening (HTS), with both biological/chemical assays (in vitro or in vitro) and computational assays. In HTS, it is useful and economical to assay only one or a few members of each cluster of compounds initially; then, only in the cases where a "hit" occurs (that is, a compound "passes" the "test" in the assay of biological or chemical activity) do other members of the corresponding cluster get sent through the assay.

Use of the method on the "transpose" of the molecular database shown earlier, in order to cluster the compounds in feature-space is shown in Table 2. It is now the columns that correspond to a set of molecules, compounds, molecular structures or sequences, while the rows correspond to features that may include substructural patterns, assay results or other aspects of the molecules. There are M' rows and N' columns, where perhaps M'=N and N'=M, for the original M and N described above. The value in table cell[i,j] is one (1) if molecule i has feature j and is zero (0) otherwise.

TABLE 2

|            | Molecule 1 | Molecule 2 | ... | Molecule N' |
|------------|------------|------------|-----|-------------|
| Feature 1  | 1          | 0          | ... | 1           |
| Feature 2  | 0          | 1          | ... | 0           |
| ...        | ...        | ...        | ... | ...         |
| Feature M' | 0          | 0          | ... | 1           |

Application of the Principles Described Herein to Discover and Analyze Genetic Networks Advanced molecular biological and computational techniques applied in large-scale genome mapping and sequencing efforts are beginning to give us access to the sequences of complete genomes, the complete expression patterns of genes, and the ability to store and manipulate this information. Such information can be used to accelerate the discovery of new disease targets and successful therapeutic compounds. It is known that the genes that form the "blueprint" for particular physical traits and systems within an organism often act together in complex ways. Genes interact in mutually regulatory ways, promoting, repressing and otherwise modulating their own and each others' activation and expression.

Traditionally, molecular biology has focused on the study of individual genes in isolation. However, to understand complex biological phenomena like neural development or oncogenesis, for example, it is necessary to study the expression patterns of tens or hundreds of genes in parallel, taking into account temporal patterns as well as anatomical patterns. Such analysis requires novel computational and statistical capabilities, such as those provided by the principles described herein.

While many variations are possible and can be envisioned by those in the art, a basic scheme for employing the methods described herein in the analysis of genetic networks might include the following steps:

Step 1: Select the genes of interest.

Step 2: Select the biological parameters by which to represent the status of a gene at a particular time. Biological parameters can include: expression of a gene (concentration levels of the associated mRNA or protein product, a particular status of a protein such as a biologically relevant phosphorylation or any other post-translational modification, the location of a given protein, or the presence or absence of a cofactor. For example, one can use polymerase chain reaction (PCR) techniques to amplify, then use known methods to detect mRNA levels for each gene, then normalize these by dividing by maximum expression levels for each gene, and then quantize these continuously varying levels into a set of z discrete levels that can be represented in the data matrix format described throughout this document. It is also possible to use concentration levels of protein products as indicators of gene activity and interactivity. The change, over timed observations, of concentrations of proteins is governed mainly by three processes: direct regulation of protein synthesis from a given gene by the protein products of other genes (including auto-regulation as a special case); transport of molecules between cell nuclei; and decay of protein concentrations.

Step 3: Select a scheme for time-sampling the biological parameters of the genes in the genetic system under analysis. At each appropriate time, use methods known in the art to measure the selected biological parameters for the selected genes.

Step 4: Represent the selected genes in terms of the selected biological parameters, and represent the measured values of the biological parameters as attributes in the data matrix. Represent the time-samples (the instances of measurement of the biological parameters) as rows in the data matrix. That is, for a cell in the data matrix, in the ith row and jth column, enter the quantity or feature measured in the ith time-sample for the jth biological paramter (which may correspond to the jth gene, or it may not, depending upon whether one or more parameters are measured for each gene). The recorded quantity, level or feature may be binary (e.g., the gene is "on" or "off"), or may be one of z discrete values. As described elsewhere in this document, any discrete-valued attribute can be represented by a binary encoding of whether that value is absent or present in a given object, so that any of the preferred embodiments of the current invention can be applied to data of this type.

Step 5: Employ the base method described above or one of the other embodiments described herein on the data matrix.

The output of the above steps, that is, a set of k-tuples of correlated attributes, can be interpreted as a set of cliques of correlated genes. For example, one might discover that one gene is "on" whenever another gene is "on". Or one might discover that when one gene G1 is in "low expression", another gene G2 is "off"; when G1 is in "medium expression", G2 is in "low expression"; and when G1 is in "high expression", then G2 is in "medium expression". Such a result might lend support to the hypothesis that G1 promotes the expression of G2, or that "G1 turns G2 on". Similarly, correlated k-tuples of genes or biological parameters might provide evidence that one gene represses, or "turns off" another gene or set of genes, and so on. All such information can be useful in building a model, for example a "boolean network", of a set of interacting genes. Such models are known to those in the art as providing valuable assistance in diagnosing, preventing and curing disease and in designing effective and economically valuable therapeutics.

The rows in Table 3 correspond to a set of time-samples (a.k.a., time points, time-slices), that is, times or periods of observance of the activity of a particular gene or gene product. The columns correspond to particular genes or gene products. The value in table cell[i,j] is one (1) if gene i is considered "on", that is, e.g., "active" or "expressed", during time j and is zero (0) otherwise. This representation and application is easily extended to situations in which the simple on/off status of a gene is replaced by a set of z distinct levels of expression, for example, as measured by observed quantities of a gene's main protein product. It is also easily extended to situations in which more than one biological parameter is used to represent the status of a single gene.

TABLE 3

|  | Gene 1 | Gene 2 | . . . | Gene N |
|---|---|---|---|---|
| Time 1 | 1 | 0 | . . . | 1 |
| Time 2 | 0 | 1 | . . . | 0 |
| . . . | . . . | . . . | . . . | . . . |
| Time M | 0 | 0 | . . . | 1 |

The methods described herein have been applied to a set of gene expression data for genes involved in the development of spinal cord in rats, as described in (G. S. Michaels, D. B. Carr, M. Askenazi, S. Furhman, X. Wen, and R. Somogyi, Pacific Symposium on Biocomputing 3:42–53, 1988). The dataset is available from those authors and as of March, 1988 is also available over the world-wide web (WWW) at http://rsb.info.nih.gov/mol-physiol/PNAS/GEMtable.html.

Using a reverse-transcriptase polymerase chain reaction (RT-PCR) protocol, the expression of 112 genes (mRNA levels, normalized by maximal expression level) was assayed over nine developmental time points (E11, E13, E15, E18, E21, P0, P7, P14, and P90 or adult, wherein E=embryonic, and P=postnatal). Included in the list of genes used are genes considered important in CNS (Central Nervous System) development covering nine major gene families.

The dataset mentioned above was easily transformed into a data matrix of objects and attributes, convenient for analysis with the methods described herein, in a few steps:

1. The real-valued (that is, continuously-valued) gene expression levels were transformed into a set of discrete values by use of a Bayesian clustering method as embodied in the SNOB software, described in (C. S. Wallace and D. L. Dowe, "Intrinsic Classification by MML—the SNOB program", Proceedings of the Seventh Australian Joint Conference on Artificial Intelligence, pp. 37–44, 1994). Bayesian methods of quantizing or discretizing real numbers are well known to persons skilled in the art. For convenience of interpreting output, these six discrete numerical values were then further transformed into a small set of alphabetic symbols, A through F.
2. A data matrix was set up such that the columns of the matrix correspond to the 112 different genes and such that the rows of the matrix correspond to the nine different developmental time points.

The methods described herein were then run on the transformed gene dataset input, several times, each time using a different combination of values for the parameters r (sample size) and T (number of sampling iterations). The method can be applied to this dataset by use of a computer program very similar to the embodiment described in Appendices A and D; however, that particular embodiment was tailored for application to the protein sequence analysis domain, meaning that some of the parameter values were fixed to be appropriate for those particular trials on the HIV protein data. The program must be modified to allow for parameter values appropriate to the input data.

These runs on the gene expression data were performed on an IBM PC-compatible computer under the Windows '95 operating system. For each run, a table of results was printed out for viewing and analysis. The results of one run, for T=100,000 and r=5, is attached as Appendix E. A researcher may wish to only print out the top 10, or 50, or 1000 (or any other number) most highly correlated k-tuples of genes. In Appendix E, the top 25 are shown.

In the attached results printout, the following format convention was used:

Each group of one or more lines reports one correlated k-tuple of genes, that is, one cset (coincidence set) which displayed a low probability of its individual component attributes being statistically independent, as described elsewhere in this document. Low probability of independence is a form of high correlation, as known to persons skilled in the art and as explained earlier in this document. For each k-tuple, the k genes are shown, followed by a numerical value for their probability of independence. (This number often displays as zero, because the calculated value is so small, so close to zero, that the decimal expansion is truncated to zero). Again, low probability value means high degree of correlation. For each gene, the symbol in A. . . F is shown, representing the quantized level of expression, followed by the internal dataset name for the gene, followed by the more standard accepted name for the gene.

The correlated k-tuples produced can be compared to the results reported by the authors in the aforementioned scientific paper. Among the analysis methods employed by those authors on this gene expression dataset was a pairwise mutual information analysis. In such analysis, a particular correlation measure, known as mutual information, was measured for each pair of the 112 genes, and the results were displayed graphically so that groups of genes with mutually high mutual information tend to appear close to each other. The method described herein is able, as shown by the results in Appendix E, to discover not only highly-correlated pairs of genes, but also 3-tuples, 4-tuples, and so on. Examination of the results in Appendix E and the results of the authors of the previously cited scientific paper shows that the two different methods tend to corroborate each other but that the current method goes farther in finding correlations among large numbers of attributes. For example, an examination of any line of output of our results reveals a set of correlated genes such that the different pairs of genes in that set are usually also listed as having high pairwise mutual information by the other authors' method.

It is not always true that a correlated k-tuple of attributes implies that all possible pairs, from that k-tuple, are also mutually correlated, nor vice versa. Therefore, a method like those described herein, that can find pairwise and higher-order k-ary correlations, offers advantages over pairwise methods which can fail to detect important higher-order correlations among genes or among other attributes in other applications.

Application of the Principles Described Herein to the Discovery of Categories in Internet/Intranet Document Databases for Use in Document Search Engines Document search by topic or keyword implies the existence of an efficient search engine and, indeed, much effort has been applied to the development of effective search algorithms. This, however, only represents a part of the total solution—the problem also requires an effective document categorization strategy. Information theory dictates that an effective set of categories, or topics, used to organize documents should be uncorrelated and roughly equiprobable. When these topics occur with widely-varying probabilities, the search space of documents will be either too broadly or too narrowly divided by some topics. If correlations exist between the topics (that is, where knowledge of the existence of a topic within a given document implies a greater probability that other topics will be found within the document as well) then the topic set can be reduced in size (by removing some of the correlated topics from the categorization set). The "equiprobability" concern can be addressed by the application of the principles described herein. This problem yields readily to statistical techniques, but standard statistical techniques usually fail to capture higher-order joint probability terms. The "decorrelation" problem is much more subtle and intractable. A sub-optimal topic set forces the search engine to examine more such topics than necessary before the results can be returned to the users (and may confuse interpretation of the organization of the documents themselves). Given that every increment in search efficiency allows greater numbers of users to use the system, the developers of such systems can not afford a lack of effective categorization of documents.

Application of the method to optimal or near-optimal topic set reduction can also be represented in terms of the M by N data matrix we have used to describe the working of the invention in other sections of this document. In one application-specific embodiment, the rows of the data matrix correspond to particular documents in the database, and the columns correspond to a proposed topic set that is intended to categorize them. (See Table 6).

The rows in Table 6 correspond to documents in a database, while the columns correspond to proposed topics used to classify them. The value in table cell[i,j] is one (1) if document i mentions topic j and is zero (0) otherwise.

TABLE 6

|  | Topic 1 | Topic 2 | ... | Topic N |
|---|---|---|---|---|
| Document 1 | 1 | 0 | ... | 1 |
| Document 2 | 0 | 1 | ... | 0 |
| ... | ... | ... | ... | ... |
| Document M | 0 | 0 | ... | 1 |

Steps involved in applying current invention to a search for a near-optimal topic set with which to classify a set of documents include:

1. Obtain an initial topic set. The field of document search is well established and effective methodologies for the creation of such sets are known to those skilled in the art.
2. Create the database using this topic set and the set of documents that the topic set categorizes. Given the topic set, all one need do is examine each document to determine whether or not it mentions each topic.
3. Present this database, in whole or part, such that each document in the database corresponds to one or more of the M objects (rows) in the embodiment's data matrix and so that each proposed topic corresponds to an attribute (column) of the data matrix.
4. Employ the base method above or one of the other embodiments described herein on the data matrix.
5. Direct the discovered correlated k-tuples of attributes to:

A graphical viewer or printer, or

A rule-generator preprocessor for rule-based system, or

A report for administrators or other users of the computer database query system, or a report-generation system, or Another computer program that performs some kind of further analysis of the data, for example, performing more in-depth statistical analysis (e.g., multiple regression) on the correlated variables, or Another computer program that performs some transformation or optimization on the database.

Any statistically significant correlation between topics in the topic set may indicate an ineffective initial choice of topics. The correlated k-tuples discovered by the method of the current invention correspond both to "highly correlated topics" (with respect to the "decorrelated topics" goal) and to "highly probable joint topics" (with respect to the "roughly equiprobable topics" goal). A person skilled in the art can use the correlations output in this application, as a guide to determining which topic(s) found to co-occur should be removed or combined from the topic set. Using the output of the application in this way would allow the administrator of such a document search engine to increase the performance of the system by reducing the number of categories to be searched in response to a user's query. The enhanced performance of the system would benefit the provider of the service in two ways: the response time of the system to user's queries would decrease and the total number of users that can be served would increase.

Applications of the Principles Described Herein to Internet and Intranet Search and Storage Internet and intranet search engines can be ranked subjectively by examining the length of time needed for users to find sites or documents of relevance to their query. Any improvement to the underlying algorithms that drive the search engine's output that allows users to find what they're looking for sooner improves the usefulness of that engine, allows it to serve more users and makes it more attractive to both the communities of users and advertisers (in the case of internet search) and users and management (in the case of company intranet search). Presented below are two uses of the principles described herein that will provide ways to get relevant information to users sooner and to better manage the storage of documents on internet or intranet search systems. In the descriptions and examples below, the principles discussed apply equally whether one is considering the internet/web and hence individual web pages and websites, or intranets, maintained within the information systems of a single company or other institution, in which case the search is for documents rather than websites per se.

For the purposes of elucidating this description, assume that each page in the set of web pages, or internal intranet documents in the set of such documents, known to the search engine has already been classified by topic and that the set of topics is fixed a priori. The goal is to present the user with the normal output of the search engine but to supplement that list of links with an additional list of topics known to be related to the user's request.

The rows in Table 7 correspond to a set of web pages, or internal intranet documents, while the columns correspond to topics. The value in table cell[i,j] is one (1) if web page or document i mentions topic j and is zero (0) otherwise.

TABLE 7

|        | Topic 1 | Topic 2 | ... | Topic N |
|--------|---------|---------|-----|---------|
| Page 1 | 1       | 0       | ... | 1       |
| Page 2 | 0       | 1       | ... | 0       |
| ...    | ...     | ...     | ... | ...     |
| Page M | 0       | 0       | ... | 1       |

Table 7 illustrates the database upon which the base method or other embodiment described herein will be run, in the data matrix format for representing objects and attributes that have been defined and described elsewhere herein. Note that, because of the characteristics of the embodiment described herein, the number of pages used in the table need not be the entire set of all web pages. The embodiment, when run (or employed) on this table will find those topics that are frequently found in the same document together. This indicates that these topics are related in some fashion and, as the set of web pages supports their association, they may be of interest to the user as well.

The advantages are several. The computational expense of these embodiments scales linearly with respect to the number of columns in the database. In this application, the number of columns represents the number of topics associated with web pages. As this number is almost certainly very large, this characteristic of the method is a real benefit. In addition, if the web pages are kept in random order, the embodiments can be run on more manageable subsets of the entire set of web pages. This allows the job of finding these associations to be divided into much smaller jobs which can be run, serially or in parallel, during idle times on the server where the search engine resides. This method can produce novel associations of great width (k) at any point during its execution. Many other "association mining" methods only find longer k-tuples of associated attributes at later stages in their long execution times. Lastly, as the list of associated topics found by this algorithm grows, the pages that select the links for these new "joint topics" can be created and cached. This would reduce server loads (thus allowing more users to access the system). As this also puts bounds on the statistical relevance of the findings, this information could be used to select which new topic indices would be cached and which would be re-created as needed.

Alternative Application of the Principles Described Herein to Manage the Storage and Retrieval of Web Pages and Documents Internet and intranet search engines attempt to order the space of web pages or documents by topic. Generally, an initial (e.g. alphabetic) ordering is not at all likely to evenly divide that space. For example, the topic "California" will have a vastly greater set of pages associated with it than will "North Dakota". A simple tree-like storage of the pages by topic (with sub-topics at lower levels of the tree) will leave "California" with a very deep tree. What would be of use in this situation would be some better way to divide the search space of pages than by just single topics. In the noted example, it would be better to have the large set of California-related web pages divided into smaller sets closer to the size of the set for North Dakota. We can keep our ordering of the pages by topic if we choose to divide larger sets into smaller ones by replacing the single topic describing the set with a series of associated topic lists that encompasses the same space. Going back to our example, if "California" were only strongly associated with "Sunshine", "Wine" and "Cars" we would replace the tree node "California" with the set of nodes "California and Sunshine", "California and Wine", "California and Cars", "California and Other". This will allow faster lookup and storage of these pages because it reduces the height of this part of the tree (in this case) by one. Recursively applying the same technique at all nodes in the tree would provide a method for ensuring better balance than could have been had before. The only thing missing from this formulation of the new tree balancing function is the discovery of the associations themselves. An application of embodiments described herein to the same table discussed in the previous section extracts this information from the set of pages. The method tells us not only which topics are related but also gives an indication of the level of support for each association in the database. Once a problematically large topic has been identified, the list of associations found by the algorithm that includes this topic can be consulted to determine how to divide the topic.

The use of tree-based storage retrieval techniques is known to those in the art, and such methods include such variations as B-trees, k-D trees, tries, k-D tries, and gridfiles. Hashing schemes can also be used instead of, or in addition to, tree-based methods per se. With all such methods, there are efficiency gains to be made, in both storage (main memory and offline memory) and running time, by taking advantage of particular distributions of the data in the application domain. The embodiments described herein can, as shown above and in other ways, be used to obtain a better understanding of and exploitation of the distribution of the data.

The advantages include all those listed for the first alternative above with one significant addition—if one is already using the method to find lists of sites related to a given query, then one is already compiling the exact list of associations that is needed here to help balance the search tree.

Application of the Principles Described Herein to Sales Analysis, Direct Mail and Related Marketing Activities Marketing executives, within retail sales companies, advertising/marketing agencies, magazine, newspaper, radio, television, film and internet companies, and non-profit and charitable organizations, need to know which kinds of people are likely to buy or contribute. In all these and other marketing contexts, it is very useful and valuable to be able to analyze data both from previous marketing campaigns (we'll use the term "mailings", though other campaigns and promotions are also included) and from previous purchases of the relevant good and services, or previous contributions to charities (let us refer to all these as "products").

It is useful for marketing executives, salespeople and management to know such things as, for example:

Which products tend to be bought together (by same customer, perhaps within same transaction)?

Which of our previous advertising campaigns or mailings produced good response (high sales of a product) and which did not?

Which demographic factors correlated with large total spending on our companies products last year?Are 25–40 year old females in the Midwest region buying our products?

Such questions can be addressed by the analysis of databases organized in terms of customers, transactions, demographic factors, previous marketing campaigns, and sales of particular products. For charitable organizations, the basic idea is the same, though instead of "sales" and "customers" the application is to "contributions" and "donors", for example. The principles described herein can be applied successfully to these analysis tasks, wherein one of the main current computational challenges is the discovery of associations (correlations) amongst sets of variables or attributes in very large databases. Table 8 illustrates the application to the analysis of databases on customer purchases of products. Table 9 is similar except that it illustrates the case wherein not only purchases are recorded in the data, but also information on previous marketing campaigns. Either of these schemes may be augmented by the inclusion of additional columns corresponding to demographic attributes of the customers, for example region of residence, age group, income group, gender, occupational category, and participation in community- or leisure-related activities.

The rows in Table 8 correspond to customers (and/or potential customers), while the columns correspond to products (goods or services) that were either purchased (denoted by 1) or not purchased (denoted by 0) by particular customers. The value in table cell[i,j] is one (1) if customer i has purchased product j and is zero (0) otherwise.

TABLE 8

|  | Product 1 | Product 2 | ... | Product N |
|---|---|---|---|---|
| Customer 1 | 1 | 0 | ... | 1 |
| Customer 2 | 0 | 1 | ... | 0 |
| ... | ... | ... | ... | ... |
| Customer M | 0 | 0 | ... | 1 |

The rows in Table 9 correspond to customers (and/or potential customers), while the columns correspond to mailings (or other marketing campaigns) and products (goods or services) that were either purchased (denoted by 1) or not purchased (denoted by 0) by particular customers. For the Mailing columns, the value in table cell[i,j] is one (1) if customer i was sent mailing j and is zero (0) otherwise. For the product columns, the value in table cell[i,j] is one (1) if customer i has purchased product j and is zero (0) otherwise.

TABLE 9

|  | Mailing 1 | .... | Mailing n1 | Product 1 | .... | Product n2 |
|---|---|---|---|---|---|---|
| Customer 1 | 1 | .... | 0 | 0 | .... | 1 |
| Customer 2 | 1 | .... | 1 | 0 | .... | 0 |
| .... | .... | .... | .... | .... | .... | .... |
| Customer M | 0 | .... | 1 | 1 | .... | 0 |

Steps involved in applying the principles described herein to a sales/marketing database include:
1. Obtain sales/marketing database as described above. Where necessary, use methods known in the art to transform continuous-valued variables into discrete-state variables.
2. Present this database, in whole or part, such that each customer in the database corresponds to one or more of the M objects (rows) in the embodiment's data matrix and so that each product or mailing corresponds to an attribute (column) of the data matrix. Mailing attributes (if any) plus product attributes together comprise the N attributes (columns) in the data matrix.
3. Employ the base method above or one of the other embodiments herein on the data matrix.
4. Direct the discovered correlated k-tuples of attributes to:
A graphical viewer or printer, or
A rule-generator preprocessor for rule-based system, or
A report for marketing personnel, magazine/newspaper circulation directors, salespeople, managers or other users of the computer database query system, or a report-generation system, or Another computer program that performs some kind of further analysis of the data, for example, performing more in-depth statistical analysis (e.g., multiple regression) on the correlated variables, or Another computer program that performs some transformation or optimization on the database.

The output in this application, can be useful in several possible ways.

For example, the output may include correlated k-tuples which comprise sets of products that tend to be bought together, either within the same transaction or by the same customer across different transactions. Such information can be used to develop "tie-in" and co-marketing campaigns, such as, for example, when buyers of NBA basketball tickets are given coupons for discounts on NBA team shirts, basketball shoes, and other basketball-related merchandise. While it is perhaps not surprising that basketball fans like to wear NBA team shirts, the steps described above are capable of discovering other associations between products that are not so obvious.

For another example, the output may include correlated k-tuples which represent particular advertising campaigns correlated with particular product purchases. Such information can help marketing executives focus their recourses on new marketing campaigns of the type most likely to increase sales.

Use of the Principles Described Herein in Clustering Customer Data

Another rather different application of the principles described herein to marketing practice is obtained by considering the transpose of the data matrix described above. Instead of customers as objects (rows) and products and demographic factors as attributes (columns), consider what is possible when the customers correspond to columns and the product and demographic variables correspond to rows (See Table 10). Use of the principles described herein to this scenario produces correlated k-tuples of customers, or customer profiles, in the space of demographic and purchasing pattern features. This is seen to be a form of clustering of the customer data, into groups of customers or customer profiles that are roughly similar in terms of their buying habits and lifestyles. Such clustering can be useful in designating special "target groups", to enable more optimal allocation of marketing resources. Once this transposition of the data is envisioned, the other steps apply entirely analogously to the descriptions given above for marketing activities.

Use of the method on the "transpose" of the marketing database shown earlier, in order to cluster the customers is shown in Table 10. It is now the columns that correspond to a set of customers, while the rows now correspond to products purchased and demographic features. There are M' rows and N' columns, where perhaps M'=N and N'=M, for the original M and N described above. The value in table cell[j,i] is one (1) if customer i purchased product j or possesses demographic feature j and is zero (0) otherwise.

TABLE 10

|  | Customer 1 | Customer 2 | ... | Customer N' |
|---|---|---|---|---|
| Prod/Demo 1 | 1 | 0 | ... | 1 |
| Prod/Demo 2 | 0 | 1 | ... | 0 |
| ... | ... | ... | ... | ... |
| Prod/Demo M' | 0 | 0 | ... | 1 |

Application of the Principles Described Herein to the Analysis of Medical, Epidemiological and/or Public Health Databases Medical scientists and practitioners have long known that many human diseases and disorders, physical and mental, are caused by complex interactions among many potential contributing factors. Such factors can include particular genetic conditions or abnormalities, exposure to biological pathogens, aspects of diet, environment (air, water, noise pollution), exposure to hazards in the home or workplace, emotional stress, substance abuse and poverty, among others. The true "causes" of a given condition often remains impossible to ascertain, though there is much folklore and anecdotal evidence offered in attempts to explain some instances. The problem of discovery and prevention of health threats is helped in recent times by the ability of researchers, insurance company representatives, epidemiologists and public health officials to compile and analyze large amounts of data on real people, healthy and sick, living and deceased. As in other applications of computers and statistical analysis to databases, one must contend in this field with a huge number of variables and the exponential complexity of their potential interactions. This kind of analysis can be improved greatly by methods that efficiently find correlations and associations amongst ten, hundreds, or thousands of variables. The principles described herein are applicable to such a situation.

Application to medical databases can also be represented in terms of the M by N data matrix we have used in other sections of this document. In one application-specific embodiment, the rows of the data matrix correspond to particular patients or subjects in a health study; and the columns correspond to factors thought to contribute to a given disease or set of diseases. Again, these factors can include socioeconomic factors, lifestyle (exercise, diet), aspects of the patient's home or workplace environment (e.g., exposure to carcinogenic chemicals), past medical treatments, and so on (See Table 11).

The rows in Table 11 correspond to patients or to human subjects in a study, while the columns correspond to potential disease factors. The value in table cell[i,j] is one (1) if patient i has experienced or been exposed to factor j and is zero (0) otherwise.

TABLE 11

|  | Factor 1 | Factor 2 | ... | Factor N |
|---|---|---|---|---|
| Patient 1 | 1 | 0 | ... | 1 |
| Patient 2 | 0 | 1 | ... | 0 |
| ... | ... | ... | ... | ... |
| Patient M | 0 | 0 | ... | 1 |

In some application-specific embodiments, there may be not just one disease represented implicitly, but, instead, a number of different diseases, represented as attributes along with the factors shown in Table 11 and described above. For example, a particular patient p may have lung cancer but not diabetes or heart disease, and so row p would have a 1 in the column corresponding to lung cancer and have values of 0 for the columns corresponding to diabetes and heart disease.

Steps involved in applying current invention to a medical/epidemiological/lifestyle factors database include:

1. Obtain database of medical/epidemiological/lifestyle factors as described above. Where necessary, use methods known in the art to transform continuous-valued variables into discrete-state variables.
2. Present this database, in whole or part, such that each patient/subject in the database corresponds to one or more of the M objects (rows) in the embodiment's data matrix and so that each potential disease factor corresponds to an attribute (column) of the data matrix. Additional attributes representing different diseases plus the disease factors together comprise the N attributes (columns) in the data matrix.
3. Employ the base method or other embodiments described herein on the data matrix.
4. Direct the discovered correlated k-tuples of attributes to:
   A graphical viewer or printer, or
   A rule-generator preprocessor for rule-based system, or
   A report for doctors, researchers, public health officials, managers or other users of the computer database query system, or a report-generation system, or
   Another computer program that performs some kind of further analysis of the data, for example, performing more in-depth statistical analysis (e.g., multiple regression) on the correlated variables, or
   Another computer program that performs some transformation or optimization on the database.

The output of this application, can be useful in several possible ways.

For example, the output may include correlated k-tuples which comprise sets of factors associated with one or more disease conditions. Such information, perhaps refined through further statistical analysis, can provide breakthroughs in understand, treating, and preventing those particular diseases.

For another example, the output may include correlated k-tuples which comprise sets of factors associated with each other, such associations being previously unknown. The discovery of associated lifestyle factors, such as particular diets and obesity or particular professions and high levels of alcohol consumption, can itself be useful in improving public health policy and medical practice.

All such discovered correlations can potentially be of great benefit to insurance providers, public or private, as they must make their actuarial tables and insurance policies reflect accurate predictions of health and life expectancy, for example, based on lifestyle, socioeconomic and other factors.

Use of the Principles Described Herein in Clustering Patient Data

Another rather different application of the principles described herein to public health and insurance policy and practice is obtained by considering the transpose of the data matrix described above. Instead of patients as objects (rows) and potential disease factors as attributes (columns), consider what is possible when the patients correspond to columns and the factors correspond to rows. (See Table 12). Use of the current invention in this scenario produces correlated k-tuples of patients, or patient-profiles, in feature-space. This is seen to be a form of clustering of the patient data, into groups of patients or patient profiles that are roughly similar in terms of their lifestyle factors. Such clustering can be useful in designating special "low-risk" of "high-risk" types of patients or insurance applicants, to enable more optimal allocation of health services, outreach programs, insurance protection, or other resources. Once this transposition of the data is envisioned, the other steps of the preceding application to analysis of medical and other databases apply entirely analogously to the descriptions given above. (See Table 12).

Use of the principles on the "transpose" of the disease factors databases shown earlier, in order to cluster the patients or policy-holders in factor-space is shown in Table 12. It is now the columns that correspond to a set of patients, medical study subjects, or potential insurance policyholders, while the rows now correspond to potential disease factors that may include lifestyle factors, socioeconomic factors, workplace factors, and so on. There are M' rows and N' columns, where perhaps M'=N and N'=M, for the original M and N described above. The value in table cell[j,i] is one (1) if patient i possesses or has been exposed to factor j and is zero (0) otherwise.

TABLE 12

|  | Patient 1 | Patient 2 | ... | Patient N' |
|---|---|---|---|---|
| Factor 1 | 1 | 0 | ... | 1 |
| Factor 2 | 0 | 1 | ... | 0 |
| ... | ... | ... | ... | ... |
| Factor M' | 0 | 0 | ... | 1 |

Application of the Principles Described Herein to the Discovery of the Causes of Failures in Complex Systems Administrators of complex integrated systems such as computer networks and factory automation systems have been faced with the difficult diagnosis problems these system pose since their inception. Where a series of events in the system (perhaps over a protracted period of time) leads to a failure of the system as a whole, the diagnosis of the true cause of the failure can be an almost insurmountable task. For example, a network interface card on a gateway computer that fails intermittently when under high load conditions may not cause the host computer to crash but may lead to errors on other computers that use the card (by proxy) to service their network requests. Such a problem would be difficult in the extreme to track down using conventional diagnosis techniques. Tools that can present administrators with a better analysis of the conditions on the system as a whole that lead to the failure would speed the diagnosis and correction of the underlying problem.

We need to define the database upon which the principles described herein will be applied.

The database as a whole can be thought of as a state record of a series of components over time. The columns of this database, when viewed in the data matrix format used throughout this document, represent the series of components; the rows represent discrete points in time. The values in the table are intended to be an encoding of each component's state (on, off, idle, error, and so on) at the time in question. Such logging procedures are well known to those skilled in the art.

The rows in Table 13 correspond to points in time, while the columns correspond to individual components in the system. The value in table cell[i,j] is the encoded state of component j at time i.

TABLE 13

|  | Component 1 | Component 2 | ... | Component N |
|---|---|---|---|---|
| Time 1 | 1 | 0 | ... | 1 |
| Time 2 | 0 | 1 | ... | 0 |
| ... | ... | ... | ... | ... |
| Time M | 0 | 0 | ... | 1 |

Steps involved in applying the method of the current invention to analysis of a system operations database include:

1. Create a database of system components and their states as described above. The choice of state sets for the components in the system will be driven by behaviors of interest to the administrators of the system as well as by the components themselves.
2. Present this database, in whole or part, as a data matrix such that each column in the data matrix corresponds to a component in the system and each row in the data matrix corresponds to a point in time in the series.
3. Employ the base method above or one of the other embodiments described herein on the data matrix.
4. Direct the discovered correlated k-tuples of attributes to:
   A graphical viewer or printer, or
   A rule-generator preprocessor for rule-based system, or
   A report for the administrators of the system, or a report-generation system, or
   Another computer program that performs some kind of further analysis of the data, for example, performing more in-depth analysis on the correlated variables, or The output in this application, can be used to indicate the events in the system that are typically seen to co-occur with a given failure. Given the formulation of the database, we need not restrict ourselves to the states of the components in the system at the time of the failure—we can expand our examination of the failure conditions to any range of points in time for which the database has records. This allows the method to help illuminate subtle causal relationships between components that ultimately lead to failure. In the simplest case, the output can be used to eliminate some components in the system from scrutiny if it is seen that they are not correlated with the failure.

Application of the Principles Described Herein to the Analysis of Complex Systems Complex systems define a large family of somewhat similar applications. For the purpose of this discussion, complex systems are defined as systems for which three are no direct detailed modeling approaches because these systems comprise a huge number of interacting individual components or parts. Examples would include (but would not be limited to) economics, individual human behavior, productivity in groups of employees, weather patterns, crime in a nation, etc. In each of these cases, there are no known methods to model the system exactly so variables or sets of variables are used to measure the state of these systems (examples in the case of economics would be the interest rate, stock market values and inflation rates). For the purposes of this description, the events in these complex systems take the form: pre-condition, action and post-condition. These interactions represent the state of the system before the actions were taken, the actions themselves and the resulting state of the system at some point after the implementation of the actions. Put another way, the set of previous perturbations of the system and their outcomes are used as a history of the system from which to derive information about the system's characteristics.

The kinds of databases of complex systems that can effectively utilize the principles described herein must meet certain restrictions. There must be some set of variables (either in common usage or derivable from knowledge in the domain) used to measure the state of the given system. These variables are used in the pre and post condition parts of each database entry. Additionally, there must be some general set of actions that may be applied to the system that encompass methods by which it is known the system may be perturbed. Returning to the economics example, the action set would include all things under the heading of "fiscal policy".

Formally, the database must include attributes representing zero or more pre-condition variables zero or more action variables, and zero or more post-conditions variables. Leaving aside the trivial case wherein the database contains zero pre and post condition variables and zero action variables, there are eight cases to consider. They will be presented exhaustively below with examples where appropriate. Note that in each case, there are two interpretations of relevance. For example, consider the case where we have pre-condition variables and action variables but no post-conditions. The correlations can be derived in two ways: the database itself could have had no post-condition variables in it (and the returned set of correlations is culled to remove any correlations that involved only variables of one type) or it can be that just the set of correlations themselves contain no post-condition variables even though the database does in fact contain them. For the purposes of the discussion, we assume the former is the case—we can always cull the results of the method on a database that has more types of variables to leave a set of correlations which do not have some types of variables.

If the database contains only variables of one type (i.e. only action variables or pre or post condition variables) then the correlations derived from it can be interpreted in one of two ways. If the variables are pre or post condition variables, then the results indicate situational archetypes—that is, sets of attribute values (or, equivalently, states of variables) that tend to be seen together. An example from the domain of weather patterns would be rain and low barometric pressure. If only action variables are present in the database then correlations found between them indicate sets of decisions that tend to be made together. In a military domain, we might discover that flanking maneuvers and offensives tended to be seen co-occurring. As these types of databases are very similar to others described elsewhere in this document (as would be the applications of the method in these cases), this section will not explicitly address them.

The cases where the database contains variables of only two of the three types are three in number.

Correlations found in a database that contains only pre-condition and action variables describe the relationship between situations in the domain and the selection of actions. An example is football play-calling (note that this also involves a complex system that can not be modeled in any direct detailed way—the play-caller). Here the correlations indicate the tendencies of the action-taking entity, e.g., a coach or quarterback.

If the database contains only action and post-condition variables, then the correlations found elucidate the effectiveness of sets of actions regardless of pre-conditions. Going back again to the football example, correlations of this type would illuminate the ability of the team in question to perform certain actions (e.g., if "third and long yardage to first down" tended to result in a poor post-condition set, like fourth down, then we would know that the team tended to be ineffective in this situation). Another important example is drug interaction. In this case, the actions are the drugs given and the post-conditions are the side-effects reported for some patient.

While the utility of the case where the database contains only pre and post condition variables may be unclear on first examination, it may well be that this is one of the most useful cases. Here we are either interested in things that tend to happen after a situation in the given domain regardless of actions taken by the decision-maker or we are in a domain where there are no actions that can be taken (or none that effect the system itself). An example of the former would be the fact that the pre-condition "third and long" in football tends to be followed by the post-condition "fourth and long". In fact, it may be the latter case that is the most interesting. Consider that case of weather patterns. If we focus on the post-condition "tornadoes" (that is, we cull the resulting correlation set so that it includes only those correlations that involve the appearance of "tornadoes" in the post-condition), then what these correlations tell us are precursor signs that tornadoes are immanent.

The last case is the most general: the database contains all three types of variables. Note that a database of this form is capable of having correlations of attributes of all the preceding types. Example domains have already been given (economies, crime in a population, etc.) Here the correlations can be thought of as rating actions sets (given some set of pre-conditions) based on the quality of the post-conditions.

The last consideration is the types of data that the database entries contain. Binary valued attributes, as noted throughout this document, can readily be accepted by this method. Other value types must be of limited range of discrete values. Where this is not the case (i.e. real-valued or integer-valued attributes), some transformation must be performed on the values in question to reduce their range of values to a more manageable number. Various clustering methods are among the preferred methods for this, and are well-known to those skilled in the art.

In all cases, the correlations returned by the method are ideal inputs to a case-based reasoning package. Given a condition of the system (i.e. the current condition), a cased-based reasoning tool could use the associations found by the principles described herein as a basis for analysis of possible outcomes of selections from the set of actions that can be applied to the system.

Generally, the principles described herein can be used as a tool to aid decision-makers. Decision-makers can be "real" or artificial (that is, the method can be used as part of an artificial intelligence engine whose purpose is to make decisions in the domain of interest).

Description of the Application of the Principles Described Herein to Databases with Pre-condition Variables and Action Variables:

Given the above-noted restrictions on the form of the database, it is clear that the input requirements for the application of the embodiments described elsewhere herein are met. In the convenient data matrix representation cited elsewhere in this document, the M rows in this context are the total selected set of pre-conditions and actions taken. If the entity that applies the actions can sensibly be personified then these rows can represent a history of the decisions made by the entity and the states of the system at the time they were made. The N columns comprise the set of state variables that define the state of the system and the set of all applicable action variables that describe the ways in which the system can be perturbed (see Table 14).

The rows of Table 14 correspond to instances of or combinations of system states (the pre-condition of the system) followed by actions taken in response to that state, while the columns correspond to variables thought to describe the state of the system and possible actions that can be applied to the system. The value in table cell[i,p] is an encoding of the measure of state variable p in event i if column p is a pre-condition column and is an encoding of the action taken in event i if column p is an action column.

TABLE 14

|  | Pre 1 | ... | Pre j | Act 1 | ... | Act k |
|---|---|---|---|---|---|---|
| Row 1 | C(1,1) | ... | C(1,j) | A(1,j+1) | ... | A(1,j+k) |
| Row 2 | C(2,1) | ... | C(2,j) | A(2,j+2) | ... | A(2,j+k) |
| ... | ... | ... | ... | ... | ... | ... |
| Row M | C(m,1) | ... | C(m,j) | A(m,j+2) | ... | A(m,j+k) |

There are some other considerations that must be addressed prior to the application of the Principles described elsewhere herein to any given domain. The set of state variables must be defined. This is left to those skilled in the domain itself (e.g., football coaches, military analysts, etc.)

Previously noted examples are the case of football play-calling by coaches and military decision made by generals. In general, preferred implementations of this invention will use the method of the current invention on databases of this form in order to extract information about the action-taking entity. The correlated state variables and actions describe the tendencies of this entity. As noted above, these may be further analyzed using case-based reasoning tools to give a better picture of the entity's likely decisions given a state of the system.

Another use of the invention on databases of this type is in discovering fraud indicators in tax collection. Here we let the pre-conditions be a set of attributes intended to capture the salient details of a tax return (such things as total income, total tax owing as reported by the individual or business, tax exemptions claimed, etc.) and choose the action variables to define a set of possible tax evasion methods. The correlations found by the invention then indicate associations between types of tax returns and types of tax evasion. As coincidence detection bounds the returned correlations statistically, we not only find indicators of evasion but also the reliability of these findings. Given that tax collection agencies can not afford to investigate all tax returns sent to them, this method allows them to find a well-chosen subset of these returns that is most likely to result in findings of fraud (and greater monetary returns for the government).

The last such use that will be presented as in the domain of insurance fraud and is very similar to the application of the principles described herein to tax collection. The pre-condition variables are intended to capture a set of details in an insurance claim that are thought to be possible indicators of fraud (amount claimed, specifics concerning the insured entity, etc.) and the action variables represent types of fraud. The results found when the principles described herein are applied show correlations between the details of insurance claims and types of fraud. Insurance companies can not investigate all claims sent to them; so, the applications of the principles described herein will narrow the total list of such claims to a set more likely to be the subject of fruitful investigations.

Steps involved in applying thprinciples described herein to a database containing pre-condition and action variables include:
1. Create the database of system states and actions taken by the action taking entity as described above. Where necessary, use methods known in the art to transform continuous-valued attributes into discrete-state attributes.
2. Present this database, in whole or part, such that each states/action set corresponds to one of the M objects (rows) in a data matrix and so that each state type aspect and action type corresponds to an attribute (column) of the data matrix.
3. Employ the base method or other embodiment described herein on the data matrix.
4. Direct the discovered correlated k-tuples of attributes to:
    A graphical viewer or printer, or
    A report for decision-makers, or a report-generation system, or
    Another computer program that will use the correlations found as a basis for making decisions (for example, a case-based reasoning package), or
    Another computer program that performs some transformation or optimization on the database.

This application of the principles described herein provides and utilizes a list of correlated state/action sets that give insight to the inclinations of the action-taking entity. Were one to be interested solely in one system state (or in only a few aspects of a given state), for example the current state, one could cull the results of any correlations that do not share a given set of aspects with that state. The resultant set would represent correlations between the aspects of interest and the actions taken in response. The resulting insight into the action-taking entity's methodology can be used in further decision-making.

Description of the Principles Described Herein as Applied to Databases with Pre-condition Variables and Post-condition Variables:

Here, too, the above-noted restrictions on the form of the database force compliance with the input requirements of the embodiments described elsewhere herein. The M rows in this context are the instances or combinations of pre-conditions and post-conditions (viewed together, one can think of these rows as being the system's transitions between states). The N columns are comprised of the set of state variables that define the state of the system before and after the transition (see Table 15).

The value in cell[i,j] of Table 15 is an encoding of the measure of state variable j either before or after the transition.

TABLE 15

|  | Pre 1 | ... | Pre j | Post 1 | ... | Post k |
|---|---|---|---|---|---|---|
| Row 1 | C(1,1) | ... | C(1,j) | A(1,j+1) | ... | C(1,j+k) |
| Row 2 | C(2,1) | ... | C(2,j) | C(2,j+1) | ... | C(2,j+k) |
| ... | ... | ... | ... | ... | ... | ... |
| Row M | C(m,1) | ... | C(m,j) | C(m,j+1) | ... | C(m,j+k) |

There are some other considerations that must be addressed prior to the application of this invention in any given domain. The set of state variables must be defined. This is left to those skilled in the domain itself.

Equally important is the selection of time quanta that define the granularity of the transitions. This too is left to those skilled in the art to decide based on their own expertise and the kinds of information they wish to extract. It is assumed that some minimum granularity is imposed by either the complexity of gathering such data or by the limits of the usefulness of such data. Given this, one can then pick any multiple of this minimum granularity to be the time between pre and post conditions. At the very least, this distance in time should be long enough for the system to have changed its state.

Possible domains of application for this invention include economics and fiscal policy, stock market prediction, athletic talent scouting and weather prediction. Presented below are brief descriptions of each in turn to show how these problems may be organized to fit the specifications of the method of the current invention.

In the domain of economics and fiscal policy, we propose a database of sets of states where the states are a set of economic indicators (inflation and interest rates, housing starts, GDP and so on). Each row in the database should contain two such states (the pre and post condition of the system) separates by a fixed amount of time. The correlations found in by the method of the current invention then give insight into cycles in the economy.

For stock market prediction, we propose a set of stocks (presumably large) which are thought to have influence over one another. Again, a fixed period of time is selected for transitions. The rows of this database then tell the transition of these stocks over the chosen period of time. The output of the invention then indicates which sets of stocks "move" in a correlated manner over that period of time.

Athletic talent scouting (e.g., by professional teams prior to a draft of young players) would involve an examination of the history of such selections. Each row of the data matrix would then pertain to an individual player. The pre-condition state is a selection of statistics (and any other information available about the player) thought to be indicative of future performance at the professional level. The post-condition state would then be some set of variables intended to measure that player's success at the professional level. The correlations discovered by the invention would help teams find the best set of indicators of future success with which to make their selections. Note that in this case, the pre and post conditions need not be of exactly the same form. There is no intended restriction on state representations to force them to be equivalent.

Weather predication is a very straightforward application of this invention. Here the granularity of the selected time quantum is based solely on the kind of information the user wishes to discover. Put another way, the time quantum determines the degree of prediction desired. If we choose a single day, then the correlations found by the method will help us predict the weather (given a set of values for each of the pre-condition variables that describes the current weather) a day in advance. If a week (or a month etc.) is the chosen quantum, then this is how far into the future the predictions will extend.

In general, preferred embodiments of this invention will use the method of the current invention on databases of this form in order to extract information about how the current state of the system acts as a predictor for a future state. Given probabilistically bounded data correlations between states of the system, effective predictions can be made about the system's behavior.

Steps involved in applying current invention to a database containing pre-condition and action variables include:

1. Create the database of transitions between system states, wherein a system state is represented by a value of a state variable, over the chosen time quantum as described above. Where necessary, use methods known in the art to transform any continuous-valued state variables into discrete-state variables.
2. Present this database, in whole or part, such that each state to state transition set corresponds to one of the M objects (rows) in the embodiment's data matrix and so that each state variable corresponds to an attribute (column) of the data matrix.
3. Employ the base method or other embodiment described herein on the data matrix.
4. Direct the discovered correlated k-tuples of attributes to:
    A graphical viewer or printer, or
    A report for decision-makers, or a report-generation system, or
    Another computer program that will use the correlations found as a basis for making decisions (for example, a case-based reasoning package), or
    Another computer program that performs some transformation or optimization on the database.

Description of the Application of the Principles Described Herein to Databases with Action Variables and Post-condition Variables:

Here, too, the above-noted restrictions on the form of the database force compliance with the input requirements of the embodiments described elsewhere herein. The M rows in this context are the total selected set of actions and post-conditions. The N columns are comprised of the set of state variables that define the state of the system before and after the transition (See Table 16).

The rows of Table 16 correspond to observed instances of, or hypothetical combinations of, actions applied to the system and their resulting system states. The columns correspond to either possible actions that can be applied to the system or are individual state representation variables. If column p corresponds to one of the action types in the database, the value in table cell[i,p] of Table 16 is an encoding of the action taken. If column j is a column used to indicate some aspect of a state of the system, then the value in the table cell[i,j] is an encoding of the measure of that aspect.

TABLE 16

|       | Act 1  | ... | Act j  | Post 1   | ... | Post k   |
|-------|--------|-----|--------|----------|-----|----------|
| Row 1 | A(1,1) | ... | A(1,j) | C(1,j+1) | ... | C(1,j+k) |
| Row 2 | A(2,1) | ... | A(2,j) | C(2,j+1) | ... | C(2,j+k) |
| ...   | ...    | ... | ...    | ...      | ... | ...      |
| Row M | A(m,1) | ... | A(m,j) | C(m,j+1) | ... | C(m,j+k) |

As noted in previous examples, decisions that must be made prior to the application of the method of the current invention to databases of this type include the choice of state variables used to store the state of the system at a given point in time and the choice of time quantum used to temporally separate the actions from the post-conditions. These choices are left to those skilled in the domain of application. The time quantum chosen must, in the most trivial case, be long enough for the actions to have had some effect on the state of the system.

Possible uses of this invention include such widely varying fields as player management in hockey and the study of drug interaction.

For the purposes of this document, player management in hockey concerns only the selection of players for the next shift on the ice given knowledge of the history of these players. The action variables in this case are binary values indicating whether or not a player is selected for the shift while the post-condition variables comprise a set of outcomes within the domain of hockey (such things as the relative score in that shift, penalties called, the length of any penalties, relative number of shots taken, etc.). By the formulation of the problem, it is clear that the discoveries produced by the invention indicate correlations between sets of players chosen and outcomes on the next shift. In situations where the opposing players are known a prior, these players can be added to the action variables. In this case, we will find correlations between sets of players, both for our team and against it, and outcomes. Given this knowledge the invention is useful as an aid to coaches in selecting players most likely to produce beneficial results.

The study of drug interaction is a natural fit for this invention. Here we let the action variables be binary values indicating whether or not a given patient has been administered some drugs or combination of drugs. The post-condition variables indicate the list of side effects reported by the patient. The results found by the invention then indicate statistically bounded correlations between sets of drugs given to patients and side effects. In this fashion, the method of the current invention can be used to determine contra-indications in the use of drugs but is perhaps best suited as a way to select sets of interactions upon which to focus further study.

Steps involved in applying current invention to a database containing action and post-condition variables include:

1. Create the database of transitions between system states and actions over the chosen time quantum as described above, wherein a system state is represented by a value of a state variable and an action is represented by a value of an action type. Where necessary, use methods known in the art to transform continuous-valued state variables and action types into discrete state variables and action types.
2. Present this database, in whole or part, to an embodiment of the current invention such that each action set/state set pair corresponds to one of the M objects (rows) in the embodiment's data matrix and so that each state variable or action type corresponds to an attribute (column) of the data matrix.
3. Employ the base method or other embodiment described herein on the data matrix.
4. Direct the discovered correlated k-tuples of attributes to:
   A graphical viewer or printer, or
   A report for decision-makers, or a report-generation system, or
   Another computer program that will use the correlations found as a basis for making decisions (for example, a case-based reasoning package), or
   Another computer program that performs some transformation or optimization on the database.

Description of the Application of the Principles Described Herein to Databases with Pre-condition Variables, Action Variables and Post-condition Variables:

Here, too, the above-noted restrictions on the form of the database force compliance with the input requirements of the embodiments described elsewhere herein. The M rows in this application are the total selected set of pre-conditions, actions and post-conditions. The N columns are comprised of the set of state variables that define the state of the system before and after the transition as well as the encoded actions types (see Table 17).

The rows of Table 17 correspond to instances or combinations of pre-condition, actions taken and the resulting post-conditions. The columns correspond to types of actions possible in the domain as well as aspects of interest to any given situation in the domain (for both pre and post condition columns). If column p corresponds to one of the action types in the database, the value in cell[i,p] of Table 17 is an encoding of the action taken. If column p is a column used to specify some aspect of either the pre-condition or the post-condition, then the value in table cell[i,j] is an encoding of the measure of that aspect.

TABLE 17

|       | Pre 1  | ... | Pre i  | Act 1    | ... | Act j    | Post 1     | ... | Post n     |
|-------|--------|-----|--------|----------|-----|----------|------------|-----|------------|
| Row 1 | C(1,1) | ... | C(1,i) | A(1,i+1) | ... | A(1,i+j) | C(1,i+j+1) | ... | C(1,i+j+n) |
| Row 2 | C(2,1) | ... | C(2,i) | A(2,i+1) | ... | A(2,i+j) | C(2,i+j+1) | ... | C(2,I+j+n) |
| ...   | ...    | ... | ...    | ...      | ... | ...      | ...        | ... | ...        |
| Row M | C(m,1) | ... | C(m,i) | A(m,i+1) | ... | A(m,i+j) | C(m,i+j+1) | ... | C(m,i+j+n) |

As noted in previous examples, decisions that must be made prior to the application of the method of the current invention to databases of this type include the choice of state variables used to store the state of the system at a given point in time and the choice of time quantum used to temporally separate the actions from the post-conditions. In this case, it should be noted that it is not necessary for the pre and post-conditions to be equivalent (with respect to the choices of variables). These choices are left to those skilled in the domain of application. The time quantum chosen must, for example, be long enough for the actions to have had some effect on the state of the system.

Possible used of this invention include economic policy, crime-fighting and military strategizing.

Given some set of variables to define the state of an economy (interest rates, inflation, GNP and so on) and a set of actions taken as part of the governing body's economic policy (issuing and buying back government bonds, etc.), we create a database of economic events of the form: existing economic state, fiscal policy measures taken and economic state following the policy decisions. The correlations found by the method of the current invention give a measure to the effectiveness of economic policy decisions, given a state of the economy. Such knowledge would be beneficial in deciding economic policy as it would show historical support (or the lack thereof) for a given set of decisions.

In a similar vein, the use of the current invention to aid in setting anti-crime policy starts with the creation of a database of previous states of the community's crime, policy measures taken and the resulting state of crime in the community. The state variables could include things like the rates for differing types of crimes (breaking and entering, auto theft, etc.), differing characteristics of crimes (i.e. whether or not handguns were used etc.) and so on. The action variables in this case could include such things as minimum sentencing guidelines for various crimes, "three-strike" laws, the adoption of the death penalty, as well as education and mental health funding. On such a database, the invention would find correlations involving existing crime states, policy decisions and the outcomes of those decisions. It is proposed that these correlations could prove an invaluable aid to those charged with making such decisions.

The concept of the "decision-maker" needs careful consideration in the domain of military strategy. It may well be the case that there is not enough of a "track record" to fill a database with enough of a history of any one general's decision making. In such a case, preferred implementations can extend the concept of the decision-maker to include all similar decision-makers. As an example, consider a single general commanding a tank division. If the general were recently promoted, one would be wise to consider all the history of all such generals of the same allegiance. To increase further the granularity of the use of the method, the database could be filled with the decisions made by all infantry lieutenants rather than with those of any one lieutenant. Correlations found would be indicative of the tendencies of that class of generals given some measure of the battlefield conditions faced when they made their decisions. Equally, one would be in a position to determine which battlefield situations they handled poorly because one has access to the outcomes of the decision sets. Such knowledge could prove vital to selecting an opposing strategy.

Steps involved in an application of the principles described herein to a database containing pre-condition, action and post-condition variables include:

1. Create the database of states and actions covering the chosen time quantum as described above. Where necessary, use methods known in the art to transform continuous-valued state variables and action types into discrete state variable and action types.
2. Present this database, in whole or part, such that each state/action/state triple corresponds to one of M objects (rows) in a data matrix and so that each state variable or action type corresponds to an attribute (column) of the data matrix.
3. Employ the base method or other embodiment described herein on the data matrix.
4. Direct the discovered correlated k-tuples of attributes to:
   A graphical viewer or printer, or
   A report for decision-makers, or a report-generation system, or
   Another computer program that will use the correlations found as a basis for making decisions (for example, a case-based reasoning package), or
   Another computer program that performs some transformation or optimization on the database.

It will be understood by those skilled in the art that this description is made with reference to the preferred embodiment and that it is possible to make other embodiments employing the principles of the invention which fall within its spirit and scope as defined by the claims on the pages following Appendices A through E attached hereto, which Appendices form a part of this description.

What is claimed is:

1. A coincidence detection method for use with a data set of objects, said objects having a number of attributes, the method comprising the steps of:
   sampling various subsets of the data set for a plurality of iterations, each iteration the sampled subset of the data set having for each object the same subset of attributes;
   detecting, and recording counts of, coincidences in each sampled subset of the data set, a coincidence being the co-occurrence of a plurality of attribute values in one or more objects in a sampled subset of the data set, where the plurality of attribute values is the same for each occurrence, the detecting and recording counts of coincidences in each sampled subset of the data set being performed before, at the same time or after sampling, detecting and recording counts of coincidences in other subsets;
   determining an expected count for each coincidence of interest that has been detected in the previous step;
   comparing, for each coincidence of interest, the observed count of coincidences versus the expected count of coincidences, and from this comparison determining a measure of correlation for the plurality of attributes for the coincidence; and
   reporting a set of k-tuples of correlated attributes, where a k-tuple of correlated attributes is a plurality of attributes for which the measure of correlation is above a respective pre-determined threshold.

2. The coincidence detection method of claim 1, wherein the comparison of observed and expected counts is calculated using a Chernoff bound on tail probabilities.

3. The coincidence detection method of claim 1, wherein the counts are recorded by storing a running total of the count of each coincidence over all of the sampled subsets.

4. The method of claim 1, wherein the steps of the method are represented by the following pseudo-code:

```
0. begin
1. read (MATRIX);
2. read (R, T);
3. compute_first_order_marginals(MATRIX);
4. csets: ={};
5. for iter=1 to T do
6. sampled_rows:=rsample(R,MATRIX);
7. attributes: =get_attributes(sampled_rows);
8. all_coincidences: =find_all_coincidences (attributes);
9. for coincidence in all_coincidences do
10. if cset_already_exists(coincidence, csets);
11. then update_cset(coincidence, csets);
12. else add_new_cset(coincidence, csets);
13. endif
14. endfor
15. endfor
16. for cset in csets do
17. expected: =compute_expected_match_count(cset);
18. observed: =get_observed_match_count(cset);
19. stats: =update_stats(cset, hypoth_test(expected, observed));
20. endfor
21. print_final_stats(csets, stats);
22. end.
```

5. The coincidence method of claim 1, further comprising the step of representing the objects and attributes in a matrix of objects versus attributes prior to sampling the data set, the data set being sampled by sampling the matrix.

6. A method comprising:
   the method of claim 1, and
   the further step of:
   applying rules that are defined by the reported correlated attributes.

7. The method of claim 1, further comprising the steps of first creating a database of transitions between system states, wherein a system state is represented by a value of a state variable, over a chosen time quantum, and presenting the database, in whole or part, as a data set such that each state to state transition set corresponds to one of the objects and so that each state variable corresponds to an attribute.

8. The method of claim 1, further comprising the steps of first creating a database of states and actions covering a chosen time quantum and presenting the database in whole or part, as a data set such that each state/action/state triple corresponds to one of the objects and so that each state variable or action type corresponds to an attribute.

9. The method of claim 1, wherein at least one of the objects corresponds to a biological sample from a subject and at least one of the attributes corresponds to a biological parameter of genes or gene products.

10. The method of claim 9, wherein at least one of the attributes corresponds to a phenotypic aspect.

11. The method of claim 9, wherein at least one of the attributes corresponds to expression of a gene.

12. The method of claim 11, wherein the expression of at least one gene is measured by mRNA.

13. The method of claim 11, wherein the expression of at least one gene is measured by protein product.

14. The method of claim 9, wherein at least some of the objects correspond to biological samples from a single subject collected over time and at least one of the attributes corresponds to expression of a gene.

15. The method of claim 14, wherein the expression of at least one gene is measured by mRNA.

16. The method of claim 14, wherein the expression of at least one gene is measured by protein product.

17. The method of claim 1, wherein said plurality of iterations is a predetermined number of iterations.

18. A coincidence detection method for use with a data set of objects, each of the objects having at least one attribute, the method comprising the steps of:

(1) sampling various subsets of the data set for a plurality of iterations, each iteration the sampled subset of the data set having for each object the same subset of attributes;

(2) detecting attribute coincidences based on results of sampling of the data set;

(3) recording attribute coincidences; and (4) comparing at least one recorded attribute coincidence count to at least one expected attribute coincidence count, wherein the expected attribute coincidence count is determined for a coincidence that has been detected in the preceding steps.

19. The method of claim 18, the method further comprising the step of:

(5) reporting attribute coincidences based on result of said comparison.

20. The method of claim 19, the method further comprising the step of applying rules that are defined by the reported attribute coincidences.

21. The method of claim 19, wherein step (5) comprises the step of reporting at least one numerical correlation value and at least one k-tuple of correlated attributes.

22. The method of claim 18, wherein the objects and the attributes of the data set are represented in a matrix.

23. The method of claim 18, the method further comprising the step of separating the data set into subsets for sampling.

24. The method of claim 18, wherein more than one subset of objects is sampled and the size of the subsets of objects sampled is a constant.

25. The method of claim 18, wherein the comparison of the recorded attribute coincidences to said expected count is done using a Chernoff bound on tail probabilities.

26. The method of claim 18, wherein step (3) comprises the step of storing a running total of counts of each attribute coincidence detected over all the subsets sampled.

27. The method of claim 18, wherein at least one of the objects corresponds to a biological sample from a subject and at least one of the attributes corresponds to a biological parameter of a gene or gene product.

28. The method of claim 27, wherein at least one of the attributes corresponds to a phenotypic aspect.

29. The method of claim 27, wherein at least one of the attributes corresponds to expression of a gene.

30. The method of claim 29, wherein the expression of at least one gene is measured by mRNA.

31. The method of claim 29, wherein the expression of at least one gene is measured by protein product.

32. The method of claim 27, wherein at least some of the objects correspond to biological samples from a single subject collected over time and at least one of the attributes corresponds to expression of a gene.

33. The method of claim 32, wherein the expression of at least one gene is measured by mRNA.

34. The method of claim 32, wherein the expression of at least one gene is measured by protein product.

35. The method of claim 18, wherein at least one of the objects corresponds to a subject and at least some of the attributes correspond to the subjects' genes or gene expression patterns and the presence of a particular drug side-effect or side-effects after having been administered a particular drug.

36. The method of claim 18, wherein at least one of the objects corresponds to a subject and at least some of the attributes correspond to the subjects' genes or gene expression patterns and the presence of a particular drug side-effect or side-effects after having been administered a particular combination of drugs.

37. The method of claim 18, wherein at least one of the objects corresponds to a subject and at least some of the attributes correspond to the subjects' genes or gene expression patterns and the response of the subject to treatment using a particular drug.

38. The method of claim 18, wherein at least one of the objects corresponds to a subject and at least some of the attributes correspond to the subjects' genes or gene expression patterns and the response of the subject to treatment using a particular combination of drugs.

39. The method of claim 18, wherein said plurality of iterations is a predetermined number of iterations.

* * * * *

UNITED STATES PATENT AND TRADEMARK OFFICE
CERTIFICATE OF CORRECTION

PATENT NO.     : 6,493,637 B1
DATED          : December 10, 2002
INVENTOR(S)    : Evan W. Steeg It is certified that error appears in the above-identified patent and that said Letters Patent is hereby corrected as shown below:

<u>Title page,</u>
Item [57], ABSTRACT,
Line 3, replace "of the data set of sampled" with -- of the data set are sampled --.

<u>Column 4,</u>
Line 4, replace "(k-/th-order)" with -- (k-1th-order) --.

<u>Column 6,</u>
Line 2, replace "(k-/th-order)" with -- (k-1th-order) --.

<u>Column 19,</u>
Line 13, replace "feature" with -- features --.

<u>Column 23,</u>
Line 43, replace "attributed" with -- attributes --.

<u>Column 71,</u>
After line 52, before "What is claimed is:", insert the attached 34 pages of Appendices.

<u>Column 72,</u>
Line 28, replace "4. csets: ={};" with -- 4. csets :={}; --.
Line 30, replace "6. sampled_rows:=rsample(R,MATRIX):" with
-- 6. sampled_rows :=rsample(R,MATRIX); --.
Line 31, replace "7. attributes: =get" with -- 7. attributes :=get --.
Line 44, replace "17. expected: =compute" with -- 17. expected :=compute --.
Line 45, replace "18. observed: =get" with -- 18. observed :=get --.
Line 46, replace "19. stats: =update" with -- 19. stats :=update --.

UNITED STATES PATENT AND TRADEMARK OFFICE
CERTIFICATE OF CORRECTION

PATENT NO. : 6,493,637 B1
DATED : December 10, 2002
INVENTOR(S) : Evan W. Steeg

It is certified that error appears in the above-identified patent and that said Letters Patent is hereby corrected as shown below:

Column 73,
Line 44, replace "steps." with -- step (2). --.

Signed and Sealed this

First Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,493,637 B1
DATED : December 10, 2002
INVENTOR(S) : Evan W. Steeg

It is certified that error appears in the above-identified patent and that said Letters Patent is hereby corrected as shown below:

<u>Title page,</u>
Item [57], ABSTRACT,
Line 3, replace "of the data set of sampled" with -- of the data set are sampled --.

<u>Column 4,</u>
Line 4, replace "(k-/th-order)" with -- (k-1th-order) --.

<u>Column 6,</u>
Line 2, replace "(k-/th-order)" with -- (k-1th-order) --.

<u>Column 19,</u>
Line 13, replace "feature" with -- features --.

<u>Column 23,</u>
Line 43, replace "attributed" with -- attributes --.

<u>Column 71,</u>
After line 52, before "What is claimed is:", insert the attached 34 pages of Appendices.

<u>Column 72,</u>
Line 28, replace "4. csets: ={};" with -- 4. csets :={}; --.
Line 30, replace "6. sampled_rows:=rsample(R,MATRIX):" with
-- 6. sampled_rows :=rsample(R,MATRIX); --.
Line 31, replace "7. attributes: =get" with -- 7. attributes :=get --.
Line 44, replace "17. expected: =compute" with -- 17. expected :=compute --.
Line 45, replace "18. observed: =get" with -- 18. observed :=get --.
Line 46, replace "19. stats: =update" with -- 19. stats :=update --.

UNITED STATES PATENT AND TRADEMARK OFFICE
CERTIFICATE OF CORRECTION

PATENT NO. : 6,493,637 B1
DATED : December 10, 2002
INVENTOR(S) : Evan W. Steeg

It is certified that error appears in the above-identified patent and that said Letters Patent is hereby corrected as shown below:

Column 73,
Line 44, replace "steps." with -- step (2). --.

This certificate supersedes Certificate of Correction issued June 1, 2004.

Signed and Sealed this

Nineteenth Day of October, 2004

JON W. DUDAS
*Director of the United States Patent and Trademark Office*

APPENDIX A

```
# perl version of Evan Steeg's Coincidence Detection Algorithm.      File coinc.pl: 1/15
# here applied to data which comes in rows and columns of ascii
# symbols.  Used first for tests on artificial and real (HIV)
# protein sequence data.
# march 1996

################################################################

$tiny_num = 0.000001;

$fact[0]  = 1;
$fact[1]  = 1;
$fact[2]  = 2;
$fact[3]  = 6;
$fact[4]  = 24;
$fact[5]  = 120;
$fact[6]  = 720;
$fact[7]  = 5040;
$fact[8]  = 40320;
$fact[9]  = 362880;
$fact[10] = 3628800;
$fact[11] = 39916800;

sub compare
{
    if ($a < $b)
    {
        $r = -1;
    }
    elsif ($a == $b)
    {
        $r = 0;
    }
    else
    {
        $r = 1;
    } print "a: $a, b: $b, r: $r\n";

return $r;
} sub comp_aa
{
#   my ($a1, $c1, $a2, $c2, $r);
    my ($c1, $c2);

#   $a1 = substr $a, 0, 1;
    $c1 = substr $a, 1;

#   $a2 = substr $b, 0, 1;
    $c2 = substr $b, 1;

if ($c1 < $c2)
    {
        $r = -1;
    }
    elsif ($c1 == $c2)
    {
        $r = 0;
    }
    else
    {
        $r = 1;
```

```perl
    }
        return $r;
} calc the factorial of a number.  want (n)
for now, it's just easier and faster to hard code them into a table
sub factorial
{
    my ($n) = @_;

print "n: $n\n";

if ($n >= 0 && $n <= 11 )
    {
        return $fact[$n];
    }
    else
    {
        print "ERROR: n larger than max defined factorial requested. ($n)\n";
        exit (0);
    }
} calc the binomial coeff.  want r (number of iterations) and h (
observed number of hits)
sub binomial_coeff
{
    my ($r, $h) = @_;
# print "r: $r, h: $h\n";

$rf = &factorial($r);
    $hf = &factorial($h);
    $rhf = &factorial(($r - $h));

print "rf: $rf, hf: $hf, rhf: $rhf\n";

return ($rf / ($hf * $rhf));
} calc the chernoff.  want ($observed, $expected, $r1, $T1)
sub chernoff
{
    my ($observed, $expected, $r1, $T1) = @_;

$diff = $observed - $expected;
    $diff_sq = $diff * $diff;
    $numerator = 2.0 * (0.0 - $diff_sq);
    $denominator = $T1 * ($r1 * $r1);
    return (exp ($numerator / $denominator));
} calc the ith power of a number.  NOTE: this thing can only grok
positive integer exponents larger than 0!
sub pow
{
    my ($i, $p) = @_;

if ($p < 0 || $p != int ($p))
    {
        print "ERROR: I can only grok positive integer exponents larger than 0!\n";
        exit (0);
    }
```

File coinc.pl: 2/15

```perl
    $a = 1.0;
    for ($n = 0; $n < $p; $n++)
    {
        $a *= $i;
    } print "i: $i, p: $p, a: $a\n";
    return $a;
} want ($r, $h, $c_element), cset and aasites assumed as global
sub prob_coincidence
{
    my ($r, $h, $c_element) = @_;
    my @elements;

if ($r > 0)
    {
        $joint     = 1.0;
        $joint_neg = 1.0;

@aalist = split /\|/, $c_element;
#print "c_elelment: $c_element, aalist: @aalist\n";

foreach $aa (@aalist)
        {
            $joint     *= $aasites{$aa};
            $joint_neg *= (1.0 - $aasites{$aa});
#print "aa: $aa, joint: $joint, joint_neg: $joint_neg\n";

}
#       $ans = &binomial_coeff($r, $h) * &pow($joint, $h) *
#              &pow($joint_neg, ($r - $h));
        $ans = &binomial_coeff($r, $h) * ($joint ** $h) *
               ($joint_neg ** ($r - $h));
    }
    else
    {
        return (0.0);
    }
#q print "joint: $joint, joint_neg: $joint_neg, ans: $ans\n";

return $ans;
} sub expected_size
{
    my ($r, $c_element) = @_;

$sum = 0.0;

foreach $h (1..$r)
    {
        $sum += (&prob_coincidence($r, $h, $c_element) * $h);
#print "r: $r, h: $h, sum: $sum\n";
    } return $sum;
} sub prob_of_correlation
{
    my ($c_element, $h_total_obs, $h_expected_total, $r, $T) = @_;
```

File coinc.pl: 4/ 15

```perl
#    $h_expected_total = &expected_size($r, $c_element);
     $ch = &chernoff($h_total_obs, ($h_expected_total * $T), $r, $T);

return $ch;
} randomly select a list of 'sample_size' unique sequences
in the range from 0 to the number of rows in @family
# want sample_size, family.
sub rsample_family
{
    my $R = shift @_;
    my @family = @_;

my (%which_rows, @sampled_family, @sampled_rows);

print "whichrows: ", keys %which_rows, "\n";

# generate $R number of unique keys
    $f = scalar @family;
    while (scalar (keys %which_rows) < $R)
    {
        $n = int (rand $f);
#print "randnum: $n\n";
        $which_rows{$n} = 1;
    }
#    print "whichrows: ", keys %which_rows, "\n";

# pick out the corresponding sequence from the 'family list'
    @sampled_rows = keys %which_rows;
    foreach $line (@sampled_rows)
    {
        push @sampled_family, $family{$line};
    } print "RSAMPLE\n";
$i = 0;
#    foreach $line (@sampled_family)
#    {
#        print $line, " : ";
#        $n = $sampled_rows[$i];
#        print $n, ":",$family{$n}, "\n";
#        $i++;
#         print "$line\n";
#    }
#print "RSAMPLE END\n";
#exit(0);

return @sampled_family;
} return the n'th column of an array
want ($n, @array)
sub column
{
    my $n = shift @_;
    my @a = @_;
    my $col;

#print "COLUMN: $n\n";
#foreach (@a)
#{
print "$_\n";
}
```

```perl
    # go thru and append the n'th element of each row in @array to $col
    $col = "";
    foreach $line (@a)
    {
        $col = $col . substr $line, $n, 1;
    } print length $col, ":", $col, "\n";
print "COLUMN END\n";

return $col;
} find all occurences of a character 'aa' in the n'th column of the
array sampled_family
# want ($aa, $n, @sampled_family)
sub find_all
{
    my $aa = shift @_;
    my $n  = shift @_;
    my @sampled_family = @_;
    my ($bstring, $col);

#   print "FIND_ALL: $aa, $n\n";
#   print "012345678901234567890\n";
#   foreach (@sampled_family)
#   {
print "$_\n";
} print "JUMPING TO COL\n";
    $col = &column ($n, @sampled_family);
#   print "GOT: $col\n";

$bstring = "";
    if ( (index $col, $aa) != -1) # make sure $aa is found in $col
    {
        for ($i=0; $i < length $col; $i++)
        {
            $c = substr $col, $i, 1;
            if ($c eq $aa)
            {
                $bstring = $bstring . "1";
            }
            else
            {
                $bstring = $bstring . "0";
            }
        }
    }
    else
    {
        $bstring = "NOT_FOUND";
    } print "$bstring\n";
print "FIND_ALL END\n";
#   exit(0);

return $bstring;
} this subroutine isn't exactly the most optimal code, but....
sub mi
```

File coinc.pl: 6/15

```perl
{
    my ($col1, $col2, $m) = @_;
    my ($s1, $s2, $row, $p1, $p2, $pj, $a1, $a2, $s, %sj, $contrib, $total);

$s1 = column($col1, @family);
    $s2 = column($col2, @family);

#   print "col1: $col1, $s1\n";
#   print "col2: $col2, $s2\n";

print "keys1: ", keys %sj, "\n";

# calc the joint prob
    for $row (0..($m-1))
    {
        $a1 = substr $s1, $row, 1;
        $a2 = substr $s2, $row, 1;

$s = $a1 . $a2;

if (exists $sj{$s})
        {
            $sj{$s}++;
        }
        else
        {
            $sj{$s} = 1;
        }
#       print "a1: $a1, a2: $a2, s: $s\n";
    }
#       print "keys2: ", keys %sj, "\n";

foreach $s (keys %sj)
    {
        $sj{$s} = $sj{$s} / $m;

if ($sj{$s} < $tiny_num)
        {
            $sj{$s} = $tiny_num;
        }
#        print "$s: $sj{$s}\n";
    }

$total = 0;
    foreach $s (keys %sj)
    {
        $a1 = substr $s, 0, 1;
        $a2 = substr $s, 1, 1;

# find partial probs
        $a1 = $a1 . $col1;
        $a2 = $a2 . $col2;

$pj = $sj{$s};
        $p1 =    asites($a1);
        $p2 = $aasites($a2);

if ($p1 < $tiny_num)
        {
            $p1 = $tiny_num;
        }
        if ($p2 < $tiny_num)
        {
            $p2 = $tiny_num;
```

File coinc.pl: 7/15

```perl
        }
        if ($pj < $tiny_num)
        {
            $pj = $tiny_num;
        }

$contrib = ($pj * log ($pj / ($p1 * $p2)));
        $total += $contrib;
#       print "a1: $a1, a2: $a2, s: $s, pj: $pj, p1: $p1, p2: $p2, contrib: $contrib, total: $total

} return $total;
} sub incidence_vec
{
    my ($col, $key) = @_;

my ($vec);

$vec = "";
    if ( (index $col, $key) != -1)
    {
        for $i (0..((length $col) - 1))
        {
            $c = substr $col, $i, 1;
            if ($c eq $key)
            {
                $vec = $vec . "1";
            }
            else
            {
                $vec = $vec . "0";
            }
        }
    }
    else
    {
        $vec = "NOT_FOUND";
    } return $vec;
} given two columns, go through each letter in the alphabet and
generate the incidence vector for them.  then if the results are
# non-zero, send them to mi2_real for the real computations
sub mi2
{
    my ($col1, $col2, $m) = @_;
    my ($s1, $s2, $key1, $key2, $total, $sum);

$s1 = column($col1, @family);
    $s2 = column($col2, @family);

$sum = 0.0;
    foreach $key1 (keys %alphabet)
    {
        $vec1 = incidence_vec ($s1, $key1);

if ($vec1 ne "NOT_FOUND")
        {
            foreach $key2 (keys %alphabet)
```

```perl
            {
                $vec2 = incidence_vec($s2, $key2);

if ($vec2 ne "NOT_FOUND")
                {
                    $total = mi2_real($vec1, $vec2, $m);

#               print "s1  : $s1\n";
#               print "vec1: $vec1\n";
#               print "s2  : $s2\n";
#               print "vec2: $vec2 \n";

#                   if ($total > 1.0)
                    {
                        printf "mi2, cols: %d, %d | key1: $key1 | key2: $key2 | total: %.9f\n", ($c
                        $sum += $total;
                    }
                }
            }
        }
    }
    print "total sum: $sum\n";
}

# Given two columns (the actual string of amino acid symbols),
#  produce all combinations (pairs) of attr1, attr2, where attr1 is
#  an incidence vector for a symbol occurring in col1 and
#  likewise for attr2 from col2.  Then call mi2 on the pair
#  of incidence vectors.
# Compute mutual_info(attr1,attr2) where attri are binary incidence
#  vectors for two a1@col1, a2@col2.

sub mi2_real {
 my ($attr1, $attr2, $m) = @_;
 my ($a,$a1,$a2,$s,$p0,$p1,$pj,%hash_single1, %hash_single2,
    $total,%hash_joint);

for $row (0..($m-1))
 {
    $a1 = substr $attr1, $row, 1;
    $a2 = substr $attr2, $row, 1;

$s = $a1 . $a2;

#print "row: $row, a1: $a1, a2: $a2, s: $s\n";

if (exists $hash_single1{$a1})
    {
     $hash_single1{$a1}++;
    }
    else
    {
     $hash_single1{$a1} = 1;
    } if (exists $hash_single2{$a2})
    {
     $hash_single2{$a2}++;
    }
    else
    {
     $hash_single2{$a2} = 1;
    }
```

File coinc.pl: 8/15

File coinc.pl: 9/ 15

```perl
            if (exists $hash_joint($s))
            {
             $hash_joint($s)++;
            }
            else
            {
             $hash_joint($s) = 1;
            }
    } foreach $s (keys %hash_joint)
    {
        $hash_joint($s) = $hash_joint($s) / $m;

if ($hash_joint($s) < $tiny_num)
        {
            $hash_joint($s) = $tiny_num;
        }
#print "s: $s, hj: $hash_joint($s)\n";
    } foreach $a (keys %hash_single1)
    {
        $hash_single1($a) = $hash_single1($a) / $m;

if ($hash_single1($a) < $tiny_num)
        {
            $hash_single1($a) = $tiny_num;
        }
#print "a: $a, hs1: $hash_single1($a)\n";
    } foreach $a (keys %hash_single2)
    {
        $hash_single2($a) = $hash_single2($a) / $m;

if ($hash_single2($a) < $tiny_num)
        {
            $hash_single2($a) = $tiny_num;
        }
#print "a: $a, hs2: $hash_single2($a)\n";
    } foreach $s (keys %hash_joint)
    {
     $a1 = substr $s, 0, 1;
     $a2 = substr $s, 1, 1;
     $pj = $hash_joint($s);
     $p1 = $hash_single1($a1);
     $p2 = $hash_single2($a2);

if ($p1 < $tiny_num)
     {
       $p1 = $tiny_num;
     }
     if ($p2 < $tiny_num)
     {
       $p2 = $tiny_num;
     }
     if ($pj < $tiny_num)
     {
       $pj = $tiny_num;
     }
```

```perl
        $total += ($pj * log ($pj / ($p1 * $p2)));
    }
    return $total;

}

#############################################################
# check to make sure a file name was given
if (scalar @ARGV != 4)
{
    print "usage: $0 data_file sample_size iterations min_freq\n";
    exit;
}

$filename    = $ARGV[0];
$sample_size = $ARGV[1];
$iterations  = $ARGV[2];
$min_freq    = $ARGV[3];

# read contents of file into array family
open (DATAFILE, $filename);
@family = <DATAFILE>;

chop @family;

# remove nial's +, -, and | delimiters
#@family = grep (!/\+/, @family); # get rid of lines beginning with '+'
#foreach (@family)                # remove all '|'s
#{
#    tr/\|//d;
#}

#@family = grep (/^\w/, @family);

#foreach (@family)
#{
print "$_\n";
} while (length $family[(scalar @family) -1] < 1)
{
#    print "Empty line: ", scalar @family, " deleted.\n";
#    pop @family;
#}

#$i = 0;
#foreach (@family)
#{
#    print "$i: $_\n";
#    $i++;
}

#############################################################
# NOW for the real stuff!

print "Sample_size: $sample_size\n";
print "Iterations : $iterations\n";
print "Min_fre    : $min_freq\n";

# construct aasite list
```

File coinc.pl: 11/15

```perl
    $n = length $family[0];
    $m = scalar @family;
    foreach $row (@family)
    {
        for $j (0..($n - 1))
        {
            $c = substr $row, $j, 1;
if (length $c != 1)
{
    print "BUG!!! $row, $j\n";
    exit;
} print "$line:$j:$c\n";
            $i = $j;  # + 1;
            $s = $c . $i;           # create aasite name print "c: $c, j: $j, i: $i, s: $s\n";

if (exists $aasites{$s})
            {
                $aasites{$s}++;
            }
            else
            {
                $aasites{$s} = 1;
            }
        }
    } figure out the alphabet
@a = keys %aasites;
#print @a, "\n";
#foreach (@a)
#{
#       print "$_:$aasites{$_}\n";
} foreach $entry (keys %aasites)
{
    $c = substr $entry, 0, 1; # want the first character in each entry
#    print $c, "\n";
    $alphabet{$c} = 1;
} print keys %alphabet, "\n";

calc marginal probabilities for each column of aasites
foreach $key (keys %aasites)
{
    $p = $aasites{$key} / $m;
    $aasites{$key} = $p;
#    print "$key : $p\n";
} for $col1 (0..($n-2))
{
    for $col2 (($col1 + 1)..($n-1))
    {
        $mi = &mi($col1, $col2, $m);
        print "columns: ", ($col1 + 1), " ", ($col2 + 1), " mi = $mi\n";

$mi2 = mi2($col1, $col2, $m); # might as well do mi2 while we're here
    }
}
```

File coinc.pl: 12/15

```perl
#exit;

MAIN LOOP seed the random number generator
$seed = 111;
#srand ($seed);   # remove '($seed) to get seed from the system clock
srand();

print "START MAIN LOOP\n";

for ($iter=0; $iter < $iterations; $iter++)
{
   my %BINS;

#   print "\nITERATION: $iter\n";
   print STDERR "ITERATION: $iter\n";

#   print "JUMP TO rsample_family\n";
   @sampled_family = &rsample_family ($sample_size, @family);

#   print "sample size: $sample_size\n";
#   print "      01234567890123456789O\n";
#   $i = 0;
#   foreach (@sampled_family)
#   {
#      print "$i : $_\n";
#      $i++;
}
#   print "rsample printed\n";

foreach $aasite (keys %aasites)
   {
      $aa      = substr $aasite, 0, 1;
      $col_num = substr $aasite, 1;

print "aa: $aa, colnum: $col_num\n";

$occurence_string = &find_all ($aa, $col_num, @sampled_family);
#      print $occurence_string, "\n";
      if ($occurence_string ne "NOT_FOUND")
      {
#         print "FOUND occ_str: $occurence_string\n";
         if (exists $BINS{$occurence_string})
         {
            $BINS{$occurence_string} = $BINS{$occurence_string} .
                                      $aasite . "|";
         }
         else
         {
            $BINS{$occurence_string} = $aasite . "|";
         }
      }
   } foreach (keys %BINS)
{
#      print "$_:$BINS{$_}\n";
} sort the collision list associated with each BIN and throw away
   # entries with just one 'collision'
   foreach $bin (keys %BINS)
   {
```

File coinc.pl: 13/15

```perl
        my @aalist;
        $s = $BINS{$bin};
#        print $s, "\n";
        @aalist = split /\|/, $s;
#        $i = 0;
#        foreach (@aalist)
{
#           print"$i:$_\n";
#           $i++;
} if ( (scalar @aalist) > 1) # throw away single 'collisions'
        {
           # then sort the others
#           $sorted_aalist = join "|", sort comp_aa @aalist;
           $sorted_aalist = join "|", sort @aalist;
#           print "sorted aalist: $sorted_aalist\n";

$BINS{$bin} = $sorted_aalist;
        }
        else
        {
#           print "chucked\n";
           delete $BINS{$bin};
        }

} print "SORTED BINS\n";
$z = 0;
#   foreach (keys %BINS)
{
#      print "$z:$_:$BINS{$_}\n";
#      $z++;
} now we update the cset table
    foreach $bin (keys %BINS)
    {
       $count = 0;
       # sum up bin hits; sample_size should equal length of bins
       for ($i=0; $i < $sample_size; $i++)
       {
          $c = substr $bin, $i, 1;
          if ($c eq "1")
          {
             $count++;
          }
       }

$key = $BINS{$bin};
#      print "cset key: $key\n";
       if (exists $cset{$key})
       {
          $cset{$key} += $count;
       }
       else
       {
          $cset{$key} = $count;
       }
    } print "CSET\n";
$z = 0;
```

```perl
#     foreach (keys %cset)
#     {
#         print "$z:$_:$cset{$_}\n";
#         $z++;
} print "$iter, BINS : ", scalar keys %BINS, "  ";
print "CSETS: ", scalar keys %cset, "\n";
      print STDERR "BINS : ", scalar keys %BINS, "\n";
      print STDERR "CSETS: ", scalar keys %cset, "\n";

} print "CSETS: ", scalar keys %cset, "\n";

print "\n\nGathering stats.\n";

foreach $entry (keys %cset)
   {
      $h_total_obs = $cset{$entry};
      $h_expected_total = &expected_size($sample_size, $entry);
      $correlation = &prob_of_correlation($entry, $h_total_obs,
                                          $h_expected_total,
                                          $sample_size,
                                          $iterations);
      if ($correlation < 0.000000001)
      {
         $correlation = 0.0;
      } if ($h_total_obs >= $min_freq)
      {
         # this is a weelly ugly hack to prevent hash key collisions
         $h = $h_total_obs;
         while (exists $output{$h})
         {
            $h = $h . "*";
         }
#         print "\nEntry    : $entry\n";
#         print "Obsrv hits: $h_total_obs\n";
#         printf "Expct hits: %.9f\n", $h_expected_total * $iterations;
#         printf "Prob corrl: %.9f\n", $correlation;
         $output{$h}{0} = $entry;
         $output{$h}{1} = $h_total_obs;
         $output{$h}{2} = $h_expected_total * $iterations;
         $output{$h}{3} = $correlation;
      }
   }

@hits = keys %output;
@hits = sort compare @hits;
#@hits = sort @hits;

#foreach (@probs)
#{
print "$_\n";
} print "SORTED\n";
foreach $hit (@hits)
{
   my (@aalist);

#  $i = index $hit, "*";
#  if ($i != -1)
```

File colpc.pl: 15/15

```perl
{
#        $h = substr $hit, 0, (index $hit, '*');
#    }

$s = $output{$hit}[0];
    @aalist = split /\|/, $s;
    foreach (@aalist)
    {
      $aa = substr $_, 0, 1;
      $col_num = substr $_, 1;
      $_ = $aa . ($col_num + 1);
    }

$s = join '|', sort comp_aa @aalist;

print "\nEntry     : ", $output{$hit}[0], "\n";

$observed = $output{$hit}[1];
    $expected = $output{$hit}[2];
    $prob     = $output{$hit}[3];

if ($expected < $observed && $prob < 0.5)
    {
       print "\nEntry     : ", $s, "\n";
       print "Obsrv hits: ", $output{$hit}[1], "\n";
       printf "Expct hits: %.9f\n", $output{$hit}[2];
       printf "Prob corrl: %.9f\n", $output{$hit}[3];
    }
}
```

APPENDIX B

HIV input: 1/10

```
TRPNNNTRKSVRIGPGQAFYATGDIIGDIRQAH
TRPNNYTRKMIPTGPGQVIYATGKIIGDIRKAY
SRPNNNTRKSVHMGPGRAFYATGDIIGDIRQAY
IRPGNNTRKSMHIGPGRPFYARG-VIGDIRQAH
IRPNNNTRKSIHIGPGQAFYATGDIIGNIRQAH
IRPNNNTRTSVHMGPGKTFYATGDIIGDIRQAH
TRPNNNTRRSMRIGPGQTFYATGDIIGDIRQAY
TRPNNNTRKSIRIGPGQAFYATGDIIGDIRQAH
TRPSNNKRTSIHIAPGRAFYATGAIIGDIRQVH
IRPNNNTRRSVRIGPGQAFYATGDIIGDIRQAH
TRHNNNTRKSIRIGPGQAFYATGDIIGDIRQAH
TRPSNNTRKSIRIGPGQAFYATGDIIGDIRQAH
TRPNNNTRRSIHIGSGRAFY----IIGDIRQAH
IRPSRTTRKRWHIGSGQAFYAIDGITGDIRKAY
TRPNHNTRRRMHIGPGRAFIATDAIVGDIRQAY
TRPSNNTRKSVPIGPGQAFYATDDIIGDIRQAH
TRPSNNTSKSIRIGPGQTFYATGRIIGDIRQAH
IRPSNNTRKSVNIGPGQAFYATGDIIGDIRQAH
TRPGNNTRKSVRIGPGQAFYATGDIIGDIRQAH
TRPGNNTRKSWHIGPGRAFYTTDGIIGDIRKAY
IRPGNNTRKGVHIGPGQAFYARGDIIGDIRQAH
TRPGNNTRKSLRIGPGQTFYATGDIIGDIRQAH
TRPNNNTRKSVRIGPGQAFYATGDIIGDIRQAH
IRPNNNTRKSVHIGPGQAFYATGDIIGDIRQAY
TRPNNNTRKSVRIGPGQTFYATGDIIGDIRQAH
TRPGNYTRKSVRTGPGQTFYATGKIIGDIRQAH
TRPNNNTRKGIHIGPGSAIYATGDIIGDIRQAH
TRPNNNTRTGIHIGPGQTFYATGEIIGNIRQAH
TRPNNNTRRSVRIGPGQTFYATGAIIGDIRQAH
IRPNNNTRKSVRIGPGQTFYAAGDIIGDIRQAH
TRPGNNTRRSVRIGPGQAFYATGEIIGDIRKAH
TRLSNNTRKSVRIGPGQTFYATGEIIGDIRRAH
TRPNNNTRKSVRIGPGQTFYATGDIIGDIRQAH
TRPNNNTRTSVRIGPGQAFYATGDIIGDTRQAH
TRPGNNTRRSVRIGPGQAIYATGDIIGDIRKAH
SRPNNNTRRSIHPGPGQTLYATGNIIGDIRQAH
TRPNNNTRRSIRIGSGQTSYATGDIIGNIREAH
SRPGNNTRKSVRIGPGQTFYATGDIIGDIRQAH
TRPNHNTRKSVRIGPGQTFYATGDIIGDIRQAH
TRPNNNTRKSVRIGPGQTFYATGDIIGDIRKAH
TRPSNNTRKGIHIGPGRAFYATGQITGDIRQAH
TRPGNNTNKNVHIGPGQAFYARGRIIGDIRKAH
TRPNNNTRHSIRIGPGQAFYATGDIIGNIRQAH
TRPNNNTRKSIHIGPGQAFYATGDIIGNIRQAH
TRPNNNTRTGIHIGPGQAFYARGAITGDIRKAY
TRPXNNTRKSIHIGPGQAFYATGDIIGDIRKAH
TRPNNNTRTSIRIGPGQTFYATGDIIGNIRQAH
TRPGNNTRTSIRIGPGQAFYGRGNIIGDIRKAH
TRPNNNTRRSIRIGPGQAFYATGDITGDIRQAH
ARPNNNTRRSIHIGPGQAFYA-SDIIGDIRQAH
TRPNNNTRKSVHIGPGQAFYATGDIIGDIRQAH
TRPNNNTRKSIRIGPGQAFYTTGDIIGDIRQAH
IRPNNNTRTSIRIGPGQAFYATGDIIGDIRQAH
TRPNNNTRKSVPIGPGQAFYATDNIIGDIRQAH
TRPNNNTRTSICIGPGQTFYA-GGIIGDIRQAH
TRPNNNTRKSVHIGPGQAFYATGDIIGNIRQAH
TRPNNNTRKSIHIGPGQAFYATGDIIGDIRQAH
TRPSNNTRTSIRIGPGQAFYATGDIIGDIRQAH
TRPNNNTRKSANIGPGQAFYATGEIIGDIRQAH
IRPNNNTLKGIHIGPGQSFYATGSIVGNIRQAH
IRPYNNTRKSIHIGPGQAFYA-SRIIGNIRQAH
TRPNNNTRKSIRIGPGQTFYA-GEIIGNIRQAH
TRPNNNTRKGVHIGPGQAFYATGDIIGDIRQAH
TRPNNNTRKSVRIGPGQAFYATGDIIGDIRQAY
TRPNNNTRTSIRIGPGQSFHATGDIIGDIRQAH
SRPNNNTRKSVHIGPGQAFYATGDVIGDIRQAY

```
IRPNNNTRKSVPIGPGRAFYATGDIIGNIRQAH
TRPNNNTRKGVRIGPGQAFYATGGIIGDIRQAH
TRPNNNTRKSVRIGPGQAFYATGDIIGDIRQAH
TRPNNNTRTSVRIGPGQTFYATGDIIGDIRRAY
VRPNNNTRTSVRIGPGQTFYATGEIIGDIRRAF
TRPNNNTRRSIRIGPGQAFYATGDIIGDIRKAH
IRPNNNTRKSVHIGPGQAFYATGDIIGDIRQAH
IRPNNNTRKSVHIGPGQTSYATGDIIGDIRQAH
TRPNNNTRKSVHIGPGQAFYATGDIIGDIRQAH
TRPNNNTRRSVHIGPGQAFYATGDIIGDIRRAH
TRPNNNTRKSIHLGPGRAFYATGDIIGDIRQAH
SRPYN-TRKNYSIGSGQAFYVTGKIIGDIRQAH
TRPYKKVRRRIHIGPGRSFY-T-SNLGDIRQAY
TRPNNNISRRIHIGRGQAFYATGGMTGNIRQAY
IRPNNNTRKSVRIGPGQAFYATGDIIGNIRQAH
TRPNNNTRRSVRIGPGQTPYATGDIIGDIRQAH
TRPNNNTRTSVHIGPGQAFYARGDIIGDIRQAH
TRPNNNTRKSIHIGPGQAFYARGDIIGNIRQAH
TRPNNNTRKSVHIGPGQAFYATGEIIGDIRQAH
TRPNNNTRKSVRIGPGQTFYATGDIIGNIRQAH
TRPNNNTRKGVHIGPGQAFYATGDIIGNIRRAH
TRPNNNTRQSVHIGPGKAFYATGGIVGDIRQAY
TRPNNNTRKSVHIGPGQAFYATGAIIGSIRQAH
TRPNNNTRRSVHIGPGQAFYATGDIIGDIRQAH
TRPGNNTRRSVRIGPGQTFYATGDIIGDIRQAH
IRPNNNTRTSVRIGPGQAFYATGDIIGDIRKAY
TRPNNNTRKSIGIGPGQTFYAADNIIGDIRQAH
TRPGNNTRTSVRIGPGQAFYATGDIIGDIRQAH
TRPNNNTRTSVRIGPGQSFYATGDIIGDIKQAH
MRPNNNTRKSISIGPGRAFFATGDIIGDIRQAH
TRPSNNRRQSVRIGPGQAFYATGDIIGDIRRAH
TRPNNNTSQGVHIGPGQVFYARDRIIGDIRKAY
TRPNNNTRKSVRIGPGQTFYATGDIIGDIRQAY
IRPNNNTRRGIHMGPGQILYATGSIIGDIRQAH
TRPNNNTRKSIRIGPGQVFYTN-DIIGDIRQAH
TRPNNNTRKSVHIGPGQAFYATGDIIGNIRQAH
TRPNNNTRKSIRIGPGQAFYATGDIIGNIRQAH
TRPNNNTRKSIRIGPGQVFYATG*********
TRPNNNTRKSVRIGPGQTFYATGDIIGDIRQAH
TRPNNNTRTSVRIGPGQAFYATCDIIGDIRRAH
TRPNNNTRKSIHIGPGRAFYTTGEIIGDIRQAH
TRPNNSKRKTLHMGPKRAFYATGDIGGYIRQAH
TRPNNNTRKSIQIGPGRAFYTTGEIIGDIRQAH
TRPNNNTRKGIHMGPGSTFYATGEIIGDIRQAH
TRPSNNTRKGIHLGFGRALYATGEITGDIRQAH
TRPNNNTRKSLSLGPGRAFYTTGDIVGDIRQAH
TRPSNNTRKGIHIGPGRTFFATGEIIGDIRQAH
TRPSNNTSKGIHMGPGGAFYTTGRIIGDIRRAY
TRPNNNTRKSISIGPGRAFYATGDIIGDIRQAH
TRPNNNTRKGIHMGWGRTFYATGEIIGAIRQPH
TRPNNNTRKSIHMGWGRAFYATGDIIGDIRQAH
TRPNNNTRKSIHVGWGRSLSTTGEIIGNIRLAH
TRPNNNTRKSIHMGWGRAFYATGEIIGDIREAH
TRPNNNTRKRIYIGPGRAVYTTGQIIGDIRRAH
ERPNNNTRKSINIGPGRAFYTTGDIIGDIRQAH
TRPSNNTRKSIHLGLGRAFYTTGDIIGDIRQAH
TRPMNNTRRSITIGPGRAFYTTGDIIGDIRQAH
TRPSNNTRKSIHLGWGRAFYATGEIIGDIRQAH
TRLNNNTRTSIHIGPGQAFYATGDIIGDIRQAH
TRPNNNTRKSIHIGPGSAFYATGDIIGDIRQAH
TRPNNNTRKSIHMGWGRTFYATGEIIGDIRQAH
TRPNNNTRKGIHIGPGRAFYAT-EITGDIRQAH
LRPSNNTRKGIHMGWGRAFYATGEIIGDIRQAH
TRPNNNTRKSIHMGWGRAFYATGEIIGNIRQAH
TRPGNNTRKGIPIGPGGSFYATERIIGDIRQAH
IRPNNNTRRSIIIGPGRAFYATGDIIGDIRQAY
```

HIV input: 2/10

HIV input: 3/ 10

TRPNNNTRKSIHIGPGRAFYATGDIIGDIRQAH
TRPNNNTXKSIHIGPGSAFYATGDIIGDIRQAH
TRPGNNTRRSIHMGWGRAFYATGDIIGDIRQAH
TRPNNNTRKSIHIGPGRAFYATGDIIGDIRQAH
TRPNNNTRKSIHMGWGRAFYATGEIIGNIRQAH
TRPNNNTRKSIHIGPGKAFYATGEIIGNIRQAY
TRPNNNTRKSIHLGWGRAFYATGEIVGDIRQAH
TRPNNNTRKSITIGPGRAFYATGEIIGDIRQAH
TRPNNNTRKSIHMGWGRTFYATGEIIGDIRQAH
TRPSNNTRKGIHIGPGRAFYATGDIIGDIRQAH
TRPSNNTRKSIHIGWGRAIYATGAIIGDIRQAH
TRPNNNTRKSIHVGWGRALYTTGEIIGNIRQAH
TRPNNNTRKSIQYGTGGAFYATGEIVGDIRQAH
TRPGNNTRKSIHIGPGRAFYTTGDIIGDIRQAH
TRPNNQTRKSIHMGWGRAFHTNGEIIGNIRQAH
TRPNNNTRKGIHMGLGRAFYATGGIVGDIRQAH
TRPSNNTRKGIHIGWGRAFYATGEITGDIRKAY
SRPNNNTRKSIHMGWGRAFYTTGEIIGDIRQAH
TRPNNNTRKSIHIGPGRAFYTTGEIIGDIRQAH
TRPGNNTRKSIHLGWGRAFYATGAIIGDIRQAH
TRPSNNTRKSIHLGWGRAFYATGEIVGDIREAH
TRPSNNTRRSIHLGPGGAFYTTGEIIGNIRKAF
TRPNNNTRKSIRIGPGSAFYATGDIIGDIRQAH
TRPNNNTRKSIPIAPGSAWFATGEIIGDIRQAH
TRPNNNTRKSIHLGWGRAFYTTGQIIGEIRQAH
TRPNNNTRKSIHVGVGRAIYATGEIIGDIRQAH
TRPSNNTRKSIHMGWGRAFYATGEIIGDIRRAH
TRPNNNTRKSIHMGWGRAFYTTGDIIGDIRQAH
TRPNNNTRKRKSIGPGRAFYTTGEVIGDIRQAH
TRPNNNTRKSIHMGPGSAIYATGEIIGDIRKAY
TRPNNNTRKGIHIGPGRAFYTT-DIIGDIRQAH
TRPNNYTSKRIRIGARRAFYTKGKIIGDIRQAH
TRPNNNTRKGIHIGPGRAVYTTGRIVGDIRLAH
TRPNNNTRKSIQRGPGRAFVTIGKI-GNMRQAH
TRPNNNTRNRISIGPGRAFHTTKQIIGDIRQAH
TRPNNNTRKSITKGPGRVIYATGQIIGDIRKAH
TRPYNNVRRSLSIGPGRAF*RTREIIGIIRQAH
TRPNNNTRKSINIGPGRAWYAT-NIIGDIRQAH
IRPNNNTRKSIPIGPGRAFYATGDIIGDIRQAH
TRPNNNTRKSIHIGPGRAFYT-GEIIGDIRQAH
TRPNNNTSKRISIGPGRAFRAT-KIIGNIRQAH
TRPNNSTRKRISIGPGRVWYTTGQIIGDIRKAH
TRPNNNTRKRISIGPGRVWYTTGQIIGNIRKAH
TRPNNNTRRSGHIGGGRTLFTT-HIVGDIRKAH
TRPNNNTRKSIHIGPGRAFYT-GEIIGDIRQAH
TRPNNNTSKRISIGPGRAFRAT-KIIGNIRQAH
TRPNNNTRKRISIGPGRASYTTGQIIGDIRKAH
TRPNNNTRKRISIGPGRAWYTTGQIIGDIRKAH
TRPNNNTRRSGHIGGGRTLFTT-HIVGDIRKAH
TRPSNNTRKSIPMGPGKAFYTTGDIIGDIRQAY
TRPNNNTRKSIHIGPGRTFFTTGDIIGDIRQAH
TRPNNNTRKSINIGPGRAFYATGEIIGNIREAH
ERPNNNTKRSITIGPGRAFDAYGGIIGDIRQAH
TRPNNNTRKSIHMGPGKAFYTTGEIVGDIRQAH
TRPNNNTRKGIHIGPGGAFYATGGIIGDIRQAH
TRLNNNTRKSINIGPGRAFYATRDIIGDIRQAH
TRPNNNTRKSIHIGPGRSFYTTGDIIGDIRQAH
TRPNNNTRKSIHIGPGRAFYTTGDIIGDIRQAH
TRPNDNTRKSIPMGPGKAFYATGDIIGNIRQAH
TRPNNNTRKSIHIGPGRAFYTTGSIIGDIRQAH
TRPNNNTRKGITIGPGRAFYATEKIIGDIRRAY
IRPNNNTRKSIPIGPGRAFYATGDIIGDIRKAH
TRPNNNTRKSIPIGPGRAFYATGDIIGDIRQAY
TRPNDNTRKSIHIGPGRAFYTTGQIIGNIRQAH
TRPNNNTRKSIHMGPGSAFYATGDIIGNIRQAH
TRPNNNTRKSIPIGPGRAFFTTGDIIGDIRQAH

HIV input: 4/10

TRPNNNTRRSIHIGPGRAFYATGDIIGDIRQAH
TRPSNNTRKGIHIGPGGAFYTTGEIIGDIRQAH
TRPSNNTRKSIHIGPGRAFYAT-DIIGDIRQAH
TRPKNEIKRRIKIGPGRAFVATGT-VGDTRQAQ
TRPNNSIKRRIHIGPGRAFFATNT-VGDTRQAQ
TRPDNEIRRSLQVGPGRAFVAAGT-AGDTRQAQ
TRPGNNTRRSIHIGPGRAFFATGDITGDIRQAH
TRPNNNTRKSITIGSGRAFHAIEKIIGNIRQAH
TRPSKTTRRRIHIGPGRAFYTTKQIAGDLRQAH
TRPNNNTRKSIRIGPGRAFVTIG-KIGNMRQAH
TRPNNNTRKSIHIGPGKAFYATGEIIGDIRQAH
TRPNNNTRKSIHIGPGSAFYTTGDIIGDIRQAH
TRPNNNTRKRVTHGPGRVWYTTGEIIGNIKQAH
TRPNNNTRKGIHLGPGGTFYATGEIIGDIRQAH
IRPNNNTRKSINIGPGRAFYTTGEIIGDIRQAH
TRPNNNTRRGIHIGLGRRFYT-RKIIGDIRQAH
TRPHNNTRKSIHIGPGRAFYTTGEIIGDIRQAH
TRPGNNTRRSIPIGPGKAFFTT-EIIGDIRQAH
TRPNNNTRKSIHIGLGRAFYTTGDIIGDIRQAH
TRPNNNTRKSIPIGPGRAFYATGEIIGDIRQAH
TRPNNNTRKSIPIGPGRAFYTTGEIIGDIRQAH
TRPNNNTRKSIHIGPGRAFYTTGEIIGNIRQAH
TRPNNNTRRSIGIGPGRAIYATDRIVGNIRQAH
IRPNNNTRKSISIGPGRAFYATGEIIGNIRQAH
TRPNNNTRKGIHIGPGRAFYATERIIGNIRQAH
TRPNNNTRRGIHIGPGRAVYTTGKIIGDIRQAH
TRPSNNTRRSIHIGPGRAFYTTGQITGNIRQAH
TRPNNNTRKSIQIGPGRAFYTTGEIIGNIRQAH
TRPNNNTRKSIHIGPGRAFYTTGDIIGDIRQAH
TRPNNNTRKSIHIGPGRAFYTTGEIIGDIRQAH
TRPNNNTRKGIHIGPGRAFYTTGEIIGDIRQAH
TRPNNNTRKSIHIGPGRAFYATGEIIGDIRQAH
TRPNNNTRKRMTLGPGKVFYTTGEIIGDIRQAH
IRPNNNTRKSIHIGPGRAFYTTGEIIGDIRQAH
TRPNNNTRKSIHIGPGRAFYTTGEIIGDIRQAH
TRPNNNTRKSIHIGPGRAFYATGEVIGDIRQAH
TRPNNNTRKGIHIGPGRAFYTTGDIIGDIRQAH
TRPNNNTRKSIHIGPGRAFYTTGEIIGDIRQAH
IRPNNNTRKSIHIGPGRAFYTTGEIIGDIRQAH
TRPNNNTRKSIPIGPGRAFYTTGDIIGNIRQAH
IRPNNNTRRSIPIGLGSAFYTT-EIIGDIRQAH
TRPNNNTRKSIHMGPGKTFYTTGDIIGDIRQAH
TRPNNNTRKSIHIGPGRAFYTTGQIIGDIRQAY
TRPNNNTRKSIPIGPGRAFYTTGEIIGDISQAH
TRPNNNTRKSIHIGPGRAFYATGDIIGDIRQAH
TRPNNNTRKSIHIGPGRAFYATGEIIGDIRQAH
IRPGNNTRKSIPIGPGRAFYATGDIIGDIRQAH
TRPNNNTRKGIRIGPGRAFIAATKIIGDIRQAH
TRPNNNTRKSIPIGPGRAFYTTGDIIGDIRQAH
TRPNNNTRKSIHIGPGKAFYATGEIIGDIRQAH
TRPNNNTRKGIHIGPGRAFYATEAIIGDIRKAY
TRPNNNTRKGIHIGPGKAFYTTGEIIGDIRQAH
TRPNNNTRKSIHIGPGRAFYTTGEIIGDIRQAH
TRPNNNTRKSINIGPGRAFYTTGGLIGDIRQAH
TRPNNNTRKSIHIGPGRAFYTTGEIIGDIRQAH
TRPNNNTRKSIHIGPGRAFYTTGEIIGDIRQAH
TRPNNNTRKSIHIGPGRAFYTTGEIIGDIRQAH
TRPNNNTRKSIHIGPGGAFYATGEIIGDIRQAH
TRPNNNTRRGIHIGPGRAFYTTGQIIGNIRQAH
TRPNNNTRKGIHIGPGRAFYATGDIIGDIRQAH
ISPNNNTRKSIHIGPGRAFYTTGEIIGDIRQAH
TRPNNNTRKSIHIGPGRAFYTTGDIIGDIRQAH
TRPNNNTRKSIHLGPGKAVYTTGEIIGDIRQAH
TRPNNNTRKSIPIGPGRAFYTTGEIIGDIRQAH
TRPNNNTRKSIHIGPGRAFYATGEIIGDIRQAH
TRPNNNTRKSIHIGPGRAFYTTGEIIGNIRQAH

HIV Input: 5/ 10

TRPNNNTRKSIHIGPGRAFYATGDIIGDIRQAH
TRPNNNTRKSIHIGPGRAFYTTGDIIGDIRQAH
TRPNNNTRKSINIGPGRAFYATGEIIGDIRQAH
TRPNNNTRKSIHIGPGRAFYATGEIIGDIRQAH
TRPNNNTRRSIPIGPGRAFYATGNIIGDIRQAH
TRPNNNTRKSINIGPGRAFYTTGEIIGDISQAH
TRPFNNTRKSIPIGPGRAFYTTGDIIGDIRQAH
TRPNNNTRRSIHIGPGRAFYTTGGIIGDIRQAH
TRPNNNTRKSIHIGPGRAFYTTGDIIGDIRQAH
TRPNNNTRIGIHIGPGRAFYATGEIIGDIRQAH
TRPNNNTRKSINTGPGRAFYTTGDIIGDIRQAH
TRPSNNTRKGIQIGPGRAFYTTGQITGDIRQAH
TRPNNNTRKGIHIGPGRAFYATGEIIGNIRQAH
TRPNNNTRKSITIGPGRAFYTTGEIIGDIRQAH
TRPNNNTRKSIHIGPGRAFYTTGEIIGDIRQAH
TRPNNNTRKSIHIGPGRAFYTTGEIIGDIRQAH
TRPNNNTRKSIHIGPGRAFYATGEIIGDIRQAH
TRPNNNTRKSIHIGPGRAFYTTGEIIGNIRQAH
TRPNNNTRRGIHIGPGRAVYTTGEIIGNIRQAH
TRPNNNTRKSIHIGPGRAFYATGDIIGDIRQAH
TRPNNNTRKSINIGPGRAFFTTGKIIGDIRQAH
TRPSNNTRKXIHIGPGRAFYATGEIIGDIRQAH
TRPNNNTSKGIHIGPGRAFYTTGDIIGDIRQAH
TRPNNNTRKGIHIGPGRAFYATGEIIGDIRQAH
TRPGNNTSRGIHIGPGRAFYTTXKIIGDIRQAH
TRPNNNTRKSINIGPGRAFYTTGDIIGDIRQAH
TRPNNNTRKSIPMGPGRAFYTTGDIIGNIRQAH
TRPHNNTRKSIPIGPGRAFYTTGEIIGDIRQAH
TRPNNNTRKGIHIGPGRAFYTTGEIIGNIRQAH
TRPNNNTRKSIHIAPGRAFYATGEIIGDIRQAH
TRPNNNTRKSIXIGPGRAFYATGEIIGDIRQAH
TRPNNNTRKSINIGPGRAFYTTGEIIGDIRQAH
TRPNNNTRKSIPIGPGRAFYTTGQIIGDIRQAH
TRPNNNTRKGIHIGPGKAFYATGEIIGNIRQAY
TRPNNNTRKGIHIGPGSAFYATGEIIGDIRQAH
TRPNNNTRKSIHIGPGRAFYTTGEIIGDIRQAH
TRPNNNTRKSIHIGPGRAFYTTGDIVGDIRQAY
TRPNNNTRKSIHIGPGRAFYATGEIIGDIRQAH
TRPNNNTRKSIHIGPGRAFYTTGDIIGDIRQAH
TRPNNNTRKSIHIGPGRAFYATGQIIGDIRQAH
TRPNNNTRKGIHIGPGRAFYATGDIIGDIRQAH
TRPNNNTIKSIHIGPGRAFYTTGQIIGDIRQAH
TRPNNNTRKGIHIGPGRAFYTTG?IIGDIRQAH
TRPNNNTRKSITIGPGRAFYTTGDIIGDIRQAH
TRPNNNTRRSINIGPGRAFYATGEIIGDIRQAH
TRPNNNTRKSIHIAPGRAFYATGEIIGDIRQAY
TRPNNNTRKSIHIGPGRAFYATGAIIGNIRQAH
TRPNNNTRKSIHLGPGQAWYATGEIIGDIRQAH
TRPNNNTRKSIHLGQGQAWYATGEIIGDIRQAH
TRPNNNTRKSIHLGPGQAWYTTGQIIGDIRQAH
TRPNNNTRKSIPLGPGRAWYATGEIIGDIRQAH
TRPNHNTRKSIPLGPGQAWYTTGQIIGDIRQAH
TRPNNNTRKGIHLGPGQAWYTTGQIIGDIRQAH
TRPNNNTRKSIPLGPGQAWYTTGQIIGDIRQAH
TRPNNNTRKSIPLGPGQVWFTTGQIIGDIRQAH
TRPNNNTRKSIHLGPGQAWYTTGQIIGDIRQAH
TRPNNYTRKXIXMGPGRXXYTTGEIIGDIRRAH
TRPNNNTRKSIHLGPGRAWYTTGQIIGDIRQAH
TRPNNNTRKSIHLGPGRAWYTTGQIIGDIRQAH
TRPNNNTRKSIPLGPGQAWYTTGQIIGDIRQAH
TRPNNNTRKGIPIGPGRAFYTTGDIIGDIRQAH
TRPNNNTSKGIPIGPGRAFYATGXIIGDIRQAH
TRPNNNTRKGIHIGPGRAFYTTGEIIGDIRQAH
TRPNNNTRKGIHIGPGRAFYTTGEIIGDIRQAH
TRPNNNTRKGIHIGPGRAFYTTGEIIGDIRQAH
TRPNNNTRKGIHIGPGRAFYTTGEIIGDIRQAH

HIV input: 6/ 10

TRPNNNTRKSIPIGPGRAFYTTGQIIGDIRQAH
TRPNNNTRKGIHIGPGRAFYTTGEIVGDIRQAH
TRPNNNTRKGIHIGPGRAFYTTGGIIGDIRQAH
TRPNNNTRKSIHMGQGRAFYATGGIIGDIRQAY
TRPNNNTRKGIHLGPGQAWYTTGQIIGDIRQAH
TRPNNNTRKGIPLGPGQAWYTTGQIIGDIRQAQ
TRLNNNTRKSIAIGPGRTVYATDRIIGDIRQAH
TRPSKNIRRSIHIGSGRAFYTIEGVAGDVRKAY
TRPNNNTRRGIHIGPGRAFYATGNIIGDIRQAH
TRPSNNTRKSIHIGPGRVFHATGEIIGDIRQAH
TRPNNNTRKRIYIGPGRAVYTTEQIIGNIRQAH
TRPGNNTRERISIGPGRAFIARGQIIGDIRQAH
TRPGNNTRKSIPIGPGRAFIATSQIIGDIRKAH
IRPNNNTRKGIGIGPGRTVYTAEKIIGDIRQAH
TRPNNNTRKSIHIGPGRAFYTTGEIIGDIRQAH
TRPNIYRKGRIHIGPGRAFHTTRQIIENIRQAH
TRPNNNTRKSIHIGPGRAFYTTGEIIGDIRQAH
TRPNKKTRKRITTGPGRVYYTTGEIVGDIRQAH
TRPNNNTRKRITMGPGRVYYTTGQIIGDIRRAH
IRPNNNTRKGINVGPGRALYTTGDIIGDIRQAH
TRPNNHTRKRVTLGPGRVWYTTGEILGNIRQAH
TRPNNNTRKSITLGPGRAFYTTGDIIGDIRQAH
TRPNNNTRKSIHIAPGRAFYTTGDIIGDIRKAH
TRPSNNTRKSIHIGPGRAFYTTGEIIGDIRQAH
TRPGNNTRKSIPMGPGRAFYATGDIIGDIRKAH
TRPNYNKRKRIHIGPGRAFYTTKNIIGTIRQAH
TRPNNNTRKGIAIGPGRTLYAREKIIGDIRQAH
TRPNNNTRRRLSIGPGRAFYARRNIIGDIRQAH
TRPNTKKIRHIHIGPGRAFYATGGIMGDIRQAH
TRPNNNTRRSINIGPGRAFYTTGDIIGDIRQAH
TRPNNNTSKRISIGPGRAFVAAREIIGDIRKAH
IRPNNNTRKSISIGPGRAFYTTGEIIGDIRQAH
TRPNNNTTRSIHIGPGRAFYATGDIIGDIRQAH
TRPNNNTRKSITIGPGRAFYATGDIIGDIRQAH
TRPNNNTRKSIYIGPGRAFHTTGRIIGDIRKAH
TRPNNNRRRRITSGPGKVLYTTGEIIGDIRKAY
IRPNNNTRKGIHIGPGKAFYTTGEIIGNIRQAH
TRPNNNTRKSINIGPGRALYTTGEIIGDIRQAH
TRPNNNTRKGIHIGPGRAFYATGEIIGDIRQAH
TRPNNNTRRSIPMGPGKAFYTT-EIIGNIRQAH
TRPSNYTGKRLSIGPGRAFVATRKIIGDIRQAH
TRPGNNTRKSITMGPGKVFYA-GEIIGDIRQAH
TRPNNNTRKSIPMGPGRAFYTTGEIIGDIRKAY
VRPSNNTRQSIPIGPGKAFYATGEIIGDIRKAH
TRPNNNTRRSVHIGPGSALYTT-DIIGDIRQAH
IRPNNNTRRSINMGPGRAFYTTGDIIGDIRQAH
TRPNNNTRRSIHIGPGRAWYTTGKITGDIRQAH
TRPNNNTRKRITMGPGRVLYTTGQIIGDVRRAH
TRPNNNTRKSIHIAPGRAFYATGEIIGDIRQAH
TRPNNNTRKGIHIGPGRAFYATGDIIGDIRQAY
TRPSNNTRKGIPIGPGRAFYTTGGIIGDIRQAH
TRPNNNTRKSIHIAPGRAFYATGGIIGDIRQAH
TRPNNNTRRSINMGPGRAFYTTGDIIGDIRQAH
TRPSNNTRKSITIGPGRAFYTTGEVIGDIRQAH
TRPNNNTRRGIHIGPGRAFYTTGEIIGDIRQAH
TRPNNNTRKSIPIGPGRAFYATGDIIGDIRQAH
TRPNNNTRKSIHIGPGKAFDAT-DIIGDIRQAH
TRPNNNTRKSIHIGPGRAFYATGEIIGDIRKAH
TRPNNNTRKGIHMGPGRAFYTTGAIIGDIREAH
TRPNNNTRRSITIGPGRAFYAT-DIIGDIRQAH
TRLSNKTRRSIHIGPGRAFYAT-DIIGDIRQAH
TRPNNNTRRSIHIAPGRAFYATGDIIGDIRQAY
TRPNNNTSRRISIGPGRAFTAREGIIGDIRQAH
TRPNNNTRRSIHIGPGKAFYATGGIIGDIRQAH
TRPNNNTRKSIHIGPGRAFYTTGDIIGDIRQAH
TRPNNNTRKSIHIGPGRAFYATGDIIGDIRQAH

HIV input: 7/ 10

TRPNNNTRKSIHIGPGRAFYTTGDIIGDIRQAH
TRPNNNTRKSIHIGPGSAFYTTGDIIGHIRQAH
TRPNNNTGKSIHLAPGRGFHATGEIIGNIRQAH
TRPNNNTRKGIAIGPGRTVYATGRIIGDIRQAH
TRPNNNTRKSIHIGPGRAFYATGGIIGEIRQAH
TRPNNNTRKGIPIGPGRAFYTTGDIIGDIRQAH
TRPNNNTRKSIHIAPGRAFYATGEIIGDIRQAH
SRPNNNTRKGIHIGPGRAFYATGDIIGDIRQAH
TRPGNNTRRSIHIGPGRAFYTTGEIIGNIRLAH
TRPNNNTRKSIPIGPGRAFYATGDIIGDIRQAH
TRPNNNTRKSIHIGPGRAFYTTGDIIGDIRQAH
TRPNNNTRKGIHIGPGRAFYATGEIIGNIRQAH
TRPNNNTRKSIHIGPGRAFYATGDIIGDIRQAH
TRPNNNTRKGIHIGPGRAFYTTGEVIGNIRQAH
TRPNNNTRKSIPMGPGKAMYATGEIIGDIRKAY
TRPNNNTRKSIHIGPGRAFYTTGEIVGDIRQAH
TRPNNNTRKSIHIGPGRAFYAT-DIIGDIRQAH
TRPNNNTRKSIPMGPGRAFYTTGEVIGNIRQAY
TRPNNNTRKSIHIGPGRAFHTTGEVIGDIRQAH
TRPNNNTRKSINIGPGRAFYATGEIIGDIRQAH
TRPNNNTRKSINIGPGRAFYTTGEIIGDIRQAH
IRPNNNTRRSIHMGPGRAFYATGDIIGDIRQAH
IRPNNNTRRSINIGPGRAFYTTGDIIGNIRQAH
TRPGNKTIRSISMGPGRAF-RTGQIIGNIRQAN
TRPNNNTRKSIPIGPGRAFYATGDIIGDIRQAH
TRPNNNTRRSIHIAPGRAFHATGNIIGDIRQAH
TRPSNNTRKSVHIGPGRAFYTTGEIIGDIRQAH
TRPNNNTRKSIHLGPGRAFYATGEIIGDIRQAH
IRPNNNTRKSIHIGPGRAFYTTGDIIGDIRKAH
TRPNNNTRKSIHIGPGRAFYTTGEIIGDIRQAH
TRPNNNTRKSIHIGPGRAFYTTGQIIGDIRQAH
TRPNNNTRKSIPIGPGRAFYTTGDIIGDIRKAH
TRPSNNTRRSIHMGLGRAFYTTGDIIGDIRQAH
TRPNNNTRKGIHIGPGRAFYTTGQIIGDIRKAH
TRPNNNTRRSIPIGPGRAFYTTGQIIGDIRQAH
IRPNNNTRKSITMGPGKVFYVT-DIIGDIRQAQ
TRPSNNTRKRIAIGPGRAVYTTEQIIGDIRRAH
ERPNNNTRKSINIGPGRAFYATGDIIGDIRQAH
TRPNNNTRKSIRIGPGQTFYATGDIIGDIRQAH
TRPNNNTRKSIRIGPGQAFYATGEIIGDIRQAH
TRPNNNTRKSISLGPGQAFYATGDIIGNIRQAH
TRPNNNTRESIRIGPGQTFYATGDIIGDIRQAH
TRPNNNTRQSIRIGPGQTFYATGDIIGDIRQAH
TRPNNNTRKSIRIGPGQTFYATGDIIGDIRQAY
TRPNNNTRKGVRIGPGQTFYATGDIIGDIRQAH
TRPNNNTRKSIRIGPGQTFYATGDIIGDIRQAH
TRPNNNTRKSIRIGPGQTFYATGDIIGDIRQAH
TRPNNNTRKSIRIGPGQTFYATGDIIGDIRRAY
TRPSNNTRKSIRIGPGQTFYATGEIIGDIRQAH
TRPNNNTRKSLRIGPGQTFYATGDIIGDIRRAH
TRPNNNTRKSTRIGPGQTFYATGDIIGDIRQAH
TRPNNNTRKSIRIGPGQTFYATGDIIGDIRRAY
TRPNNNTRKSIRIGPGQAFYATGDIIGDIRQAY
TRPNNNTRKSIKIGPGQAFYATNDIIGNIRQAH
TRPNNNTRQSIRIGPGQVFYATKDIIGDIRQAH
TRPTNNTRQSIRIGPGQAFFATKGIIGDIRQAH
TRPNNNTRKSIRIGPGQTFYATGDIIGDIRQAH
TRPNNNTRKSIRIGPGQAFYATGGIIGDIRQAH
TRPNNNTRKSVRIGPGQTFYATGDIIGDIRQAY
TRPNNNTRKSVRIGPGQTFYATGDIIGNIRQAH
TRPGNNTRKSMRIGPGQPFYATGDIIGNIRQAH
TRPNNNTRKSIRIGPGQAFYATNDIIGDIRQAH
TRPNNNTRKSMRIGPGQTFYATGDIIGNIRQAH
TRPNNNTRKSVRIGPGQTFYATGDIIGDIRQAH
VRPNNNTRKSIRIGPGQTFYATN**********
TRPNNNTRQSVRIGPGQAFYATKDIIGDIRQAH

HIV input: 8/ 10

TRPGNNTRKSIRIGPGQTFYATGDIIGDIRQAH
TRPNNNTRRSIRIGPGQVFYANNDIIGDIRQAH
TRPNNNTRKSIRIGPGQTFYATNEIIGNIREAH
ARPNNNTRKSMRIGPGQTFYATGDIIGDIRQAH
TRPNNNTRKSVRIGPGQTFYATGDIIGDIRQAH
TRYANNTRKSVRIGPGQTFY-TNDIIGDIRQAH
ARPNNNTRESIRIGPGQTFYATGDIIGDIRQAY
TRPNNNTRKRIRVGPGQTVYATNAIIGDIRQAH
TRPSNNTRKSIRIGPGQAFYATGGIIGNIRQAH
ARPGNNTRKSIRIGPGQTFFATGAIIGDIRQAH
TRPNNNTRKSIRIGPGQTFYATGDIIGNIRQAH
TRPYNNTRQRTHIGPGQALYTT-RIIGDIRQAH
TRPNNYKRQGTPIGLGQALYTT-RVIGDIRKAH
TRPNNNTRQGTHIGPGQALYTT-GVIGDIRKAH
TRPYNNTRQSTRIGPGQTLFTT-KIIGDIRQAH
TRPYNNTRQGTHIGPGRAYYTT-NIIGDIRQAH
TRPYNNTRQGTHIGPGQTLFTT-KIIGDIRQAH
TRPYNNKRQRTPIGLGQVLHTT-RVKGDIRQAH
TRPYSRVRQGAHIGPGRAYYAT-NIFGDIRQAR
TRPSNNTRQSTRIGPGQALYTN-KIIGNIRQAH
ARPYNNTRQSTRIGPGQALFTS-KIIGNIRQAH
TRPYENMRQRTPIGLGQALVTS-RIKGRIRPAY
TRPYNNTRQGTHIGPGRAYYTT-RILGNIRQAH
TRPYNNTIQGTHIGPGRAYYTTISVIGDIRQAH
TRPYNNTIQKTSIGRGQALYTT-ETRGDIKQAF
TRPYNNIRQRTPIGSGQALYTT-RRIGDIRQAY
TRPYNNTRQGTHIGPGRAYYTT-RIVGNIRQAH
TRPYNNTRQSTHFGPGRAYYTT-DIIGDIRQAH
TRPNNNTRQSTQIGPGQALFTKTRIIGDIRQAH
TRPYENVRHRTPIGLGQALITN-RIKAKIGQAY
TRPYNQIRQRTSIGQGQALYTT-RVTGDIRKAY
TRPYNNTRKGIHIGPGRAYYTT-NIVGNIRQAH
TRPYDKVSYRTPIGVGRASYTT-RIKGDIRQAH
TRPYNNIRQRTPIGLGQALYTT-RRIEDIRRAH
IRPYNNTREGTHIGPGRALFTT-DIIGDIRQAH
ARPYAIERQRTPIGQGQVLYTT-KKIGRIGQAH
TRPNNNTRQSTHIGPGQAIYTLTKVVGDIRQAH
SRPYENKRRRTPIGLGQAYYTT-KLKGYIRPAH
TRPEKIKRRGTPIGLGQAYLTT-QITGYIRQAH
TRPYRNIRQRTHIGTGQAYYTK-GIKGVAGQPH
IKPNKTKIQRTSIGLGQALYTNDKIIGNIRQAY
ARPYIKIWRRTHIGSGQAYSTK-RIQNYTGPAH
TRPKNITIQRTPIGLGQALYTT-KRIGVIGQAS
SRPRNVTIQRTSIGSGQALYTT-KRIGYIKQAH
TRPYHNKIQRTHIGTGQALHTT-RITGYIGQAH
TRPYYNIRQRTPIGLGQALYTTRGTTKVIGQAH
TRPYNKTSQRTSIGQGRALYTT-KPTGYIRQAY
SRPYKSTRIRTHIGSGQAYYRT-NIQGDIRQAY
TRPYRAMRRRTSIGQGQAYYTTTGIGGNIRQAY
TRPYSNKRQSTPIGLGQALYTT-RGRGDIRKAH
ARPYEKKRRTTPIGLGQALITS-RNFEKIGQAH
TRPYKS---IRRIGPGRWQTYY--TTNITGRAH
IRPNKRTRQRTHIGSGQALYTT-KIVGDIRQAH
TRPDNIKRQRTPIGQGQALYTTRLTTRRIGQPH
MRPYNNKRQSVHIGPGRAFYTT-NIIGDIRQAH
TRPYNNTRQGTHIGPGRAYWTT-NIIGDIRQAH
TRPYNNTRQGIHIGPGRAYYTD-QITGDIRQAH
TRPSNNTRKSIHIGPGQALFTI-DIIGNIRQAH
TRPNNNTRQSTHIGPGQALYTT-KIIGDIRRAH
TRPANNTRQSVHLGPGQALYTT-RVIGDIRQAY
TRPYNNIKIQTPIGRQQALFTT-RIKGIKGQAH
TRPNNNTRQSIHIGPGQALYTT-NVIGDIRQAH
TRPYTNKRQGTHMGPGRALYTI-DITGDIRQAY
TRPYNNTRQSTHIGPGQALYTT-NIIGDIRQAH
VRPYSNQRRRTPIGLGQALYTTMDNMKNIKQAY
TRPYNNIKIQTPIGRGQALFTT-RRKGIKGQAH

```
TRPYTKTRH-----RAQGRAWWTTGITGDIRQAY
ARPYENIRQRTPIGTGQALYTTKK-IGKIGQAH
TRPYSKERLKTSIGQGQALYTTVKVTGDIRQAH
ARPYQNTRQRTPIGLGQSLYTT-RSRSIIGQAH
TRPNKITRQSTPIGLGQALYTT-RIKGDIRQAY
TRPGNNTRRGIHFGPGQALYTT-GIVGDIRRAY
TRPYKYTRQRTSIGLRQSLYTIKKKTGYIGQAH
TRPYRNIRQRTSIGLGQALYTT-KTRSIIGQAY
IRPNNNTRQSTHLGPGQALYTT-KVIGDIRQAY
TRPNNNTRKSIHIGPGQAIYTT-DVIGDIRQAY
TRPNNNTRKGIHIGPGQALYTSGDIVGDIRQAH
TRPNNNVRQRTPIGPGQAFYTTG**********
TRPSNNTRTSITIGPGQVFYRTGDIIGDIRKAY
TRPFKNMRTSARIGPGQVFYKTGSITGDIRKAY
TRPFKKVRISARIGPGRVFHTTGNINGDIRKAY
TRPFKRVRTSVRIGPGRVFHKTGAINGDIRKAY
TRPSNNTRTSVRIGPGQVFYKTGDIIGDIRRAY
TRPFKKTRISARIGPGRVFHKTGAILGDIRKAF
TRPSNNTRTSVRIGPGQVFYKTGEIIGDIRKAF
TRPSNKIRTSVRIGPGQVFYKTGAIMGDIRKAF
TRPSNNIRTSVRIGPGQVFYKTGSITGDIRKAF
TRPFKKHRTSVRIGPGRVFYKTGSITGDIRKAY
TRPYKNTRTSARIGPGQVFYKTGSITGDIRKAY
TRPSNNTRTSVRIGPGQVFYGTGEIIGDIRRAF
TRPSTTIRTSSRIGPGQAFYKIEGISGNIRAAY
TRPSNNTRTRITIGPGQVFYRTGDIIGDIRKAY
TRPSNNTRTSITIGPGQIFYRTGDIIGDIRKAY
TRPSNNTRTSITIGPGQVFYRTGDIIGDIRKAY
TRPSNNTRTSITIGPGQVFYRTGDIIGDIRKAY
TRPSNNTRTSITIGPGQVFYRTGDIIGNIRKAY
TRPSNNTRTSITIGPGQVFYRTGDITGNIRKAY
TRPSNNTRTSIPIGPGQVFYRTGDIIGNIRKAY
TRPSNNTRTSITMGPGQVFYRTGDIIGDIRRAY
TRPSNNTRPSITIGPGQVFYRTGDIIGDIRKAY
TRPSNNTRTSITIGPGQVFYKTGDIIGNIRKAY
TRPSNNTRTSIPIGPGQVFYRTGDIIGDIRKAY
TRPSNNTRTSITIGPGQVFYRTGDIIGDIRKAY
TRPSNNTRTSIPIGPGQAFYRTGDIIGDIRKAY
TRPSNNTRTSITIGPGQVFYRTGDIIGNIRKAY
TRPSNNTRTSITIGPGQVFYRTGDIIGDIRKAY
TRPSNNTRTSITIGPGQVFYRTGDIIGDIXKAY
TRPSNNTXPSITKGPGQVFYRTGDIIGDIRXAY
TRPSNNTRTSITIGPGQVFYRTGDIIGDIRKAY
TRPSNNTRTSINIGPGQVFYRTGDIIGDIRKAY
TRPSNNTRTSITVGPGQVFYRTGDITGDIRKAY
TRPSNNTRTSIPIGPGQVFYRTGDIIGDIRKAY
TRPSNNTRTSITIGPGQVFYRTGDIIGDIRQAY
TRPSNNTRTSINIGPGQVFYRTGDIIGDIRKAY
TRPSNNTRTSITIGPGQVFYRTGDIIGDIRKAY
TRPSNNTRTSITIGPGQVFYRTGDIIGNIRKAY
TRPSNNTRTGITIGPGQVFYRTGDIIGDIRKAY
TRPSNNTRTSITIGPGQIFYRTGDIIGDIRKAY
TRPSNNTRTSITIGPGQVFYRTGDIIGDIRKAH
TRPSNNTRTSLTIGPGQVFYRTGDIIGDIRKAY
TRPSNNTRTSITIGPGQVFYRTGDIIGDIRRAY
TRPSNNTRTSINIGPGQVFYRTGDIIGDIRKAY
TRPSNNTRTSITIGPGQVLYKTGDIIGDIRKAY
TRPSNNTRTSTTIGPGQVFYRTGDITGNIRKAY
TRPSNNTRTSVRIGPGQVFYRTGDIIGDIRKAY
TRPSNNTRTSITIGPGQVFYRTGDIIGNIRKAY
TRPNNNTRKSIHLGPGQAFYATGDIIGDIRKAH
TRPNNNTRKSIQLGPGRAFYTTGEIIGDIRKAH
TRPNNYTRKSIYFGPGRAFHTAGKIIGDIRKAH
TRPNNNTRKGIHIGPGRAFYATGDIIGDIRKAH
TRPNNNIRKSIPLGPGRAFYATGEIIGDIRKAH
```

HIV input: 9/10

```
TRPSKTIRRRIRIGLGRVFYAT-GVNGDIRKAY
TRPNNNTRKSIHIGPGRAFYATGDIIGDIRKAY
TRPNNNTRKSIRIGPGQVFYATGDIIGDIRKAY
TRPNNNTRKGIRIGPGRVIYATSAITGDIRQAH
TRPNNNTRKSIHLGPGQAFYATGDIIGDIRKAH
TRPNNNTRKSIHLGPGQAFYATDDIIGDIRKAH
TRPNNNTRKSIHLGPGQAFYATGDIIGDIRKAY
TRPNNNTRKSIHLGPGQAFYATGDIIGDIRKAH
TRPNNNTRKSIHLGPGQAFYATGDIIGDIRKAY
TRPNNNTRKSIHLGPGQAFYTTGDIIGDIRKAH
TRPNNNTRKSIHLGPGQAFYATGDIIGDIRKAH
TRPNNNTRKSIHLGPGQAFYATGDIIGDIRKAH
TRPNNNTRKSIHLGPGQAFYATGDIIGDIRKAH
TRPNNNTRKSIHLGPGQAFYATGDIIGDIRKAH
TRPNNNTRKSIHLGPGQAFYATGXIIGNIRKAY
TRPNNNTRKGIHIGVGRPFYRTVDIVGDIRKAH
TRPNNNTRKSIHLGPGQAFYATGDIIGDIRRAY
TRPNNNTRKSIXLGPGQAFYTTGNIIGDIRKAH
TRPNNNTRKSIHIGPGQAFYATGDIIGNIRKAH
TRPNNNTRKSIHLGPGQAFYATGNIIGDIRKAH
TRPNNNTRKSIHIGPGQAXYTTGDIIGDIRKAH
TRPNNNTRKSIHLGPGQAFYATGDIIGDIRKAH
TRPNNNTRKSIHLGPGQAFYTTGDIIGDIRKAH
TRPNNNTRKSIHLGPGQAFYTTGDIIGDIRKAH
TRPNNNTRKSIHLGPGQAFYATGDIIGDIRKAY
TRPNNNTRKSIHLGPGQAFYATGDIIGDIRKAH
TRPNNNTRKSIHLGPGQAFYATGDIIGDIRKAH
TRPNNNTRKSIHLGPGQAFYATGDIIGDIRKAH
TRPNNNTRKSIHLGPGQAFYATGGIIGNIRKAH
TRPNNNTRKSIHLGPGQAFYATGDIIGDIRKAY
TRPNNNTRKSIHLGPGQAFYATGDIIGDIRKAH
TRPNNNTRKSIHIGPGQAFYATGDIIGDIRKAH
TRPNNNTRKSIHIGPGQAFYATGDIIGDIRKAH
TRPNNNTRKSIHIGPGQAFYATGEVIGDIRKAH
TRPNNNTRKSIHLGPGQAFYATGDIIGDIRKAH
TRPNNNTRKSIHLGPGQAFYATGDIIGDIRKAH
TRPNNNTRKSIHLGPGQAFYTTGEIIGDIRKAH
TRPNNNTRKSITIGPGQAFYATGDIIGDIRQAH
TRPNNNTRKSISFGPGQAFYATGDIIGDIRQAH
TRPNNNTRKSIHIGPGQALYATGAIIGDIRQAH
TRPNNNTRKSIKFGTGRVLYATGAIIGNIRQAH
TRPNNNTRKSIRIGPGQAFYATGEIIGDIRQAH
TRPNNNTRKSITLGPGQAFYATGDIIGNIRQAH
TRPNNNTRKSITFAPGQAFYATGDIIGNIRQAH
IRPNNNTRKSIPIGPGQAFYATGDIIGDIRQAH
TRPNNNTRKSISIGPGQAFYATGDIIGDIRKAY
TRPNNNTRKSISIGPGQAFYATGDIIGDIRKAY
TRPNNNTRRSMRIGIGRGQTFHGAIIGDIRQAH
TRPNNNTRKSIRIGPGQAFYATGDIIGDIRQAH
TRPNNNTRKSINIGPGRAFYATGDIIGDIRQAY
TRPNNIRNIRTHIGSGQAIFTT-KVIGDIRKAY
TRPNNNTRTSIHLGPGRAFYATGDIIGDIRQAH
TRPGNTTRRSMRIGPGRTFYTI----GDIRKAH
TRPNNNTRKSVRIGPGQTFYATGDMKGDIRQAH
TRPNNNIRKSIRIGPGQAFFATGDIIGNIRQAQ
TRPNNNTRKSIRFGPGQAFYT-SDIIGDIRQAY
TRPNNNTRRSIHVGPGQAFYATGDIIGNIRKAH
TRPSNNTRRSIRFGPGQAFY-TNDIIGDIRQAY
TRPGSDKKIRIRIGPGKVFYAKGGITG---QAH
ERPGIDIQE-IRIGPMA-WYSMGLGGTSSRAAY
ERPQIDIQE-MRIGPMA-WYSMGIGGTSSRAAY
IREIAEVQD-IYTGPMR-WRSMLKRSNPRSRVA
ERPGNQTIQKIMAGPMA-WYSM--NTKRA--AY
```

HIV input: 10/10

APPENDIX C

HIV output: 1/6

```
 0 | 0.00 | & $ A18|Q31|H33 $ & 36019 & 15684.208314 & 0.000000 & \cr
 1 | 0.00 | & $ A18|T21 $ & 33816 & 12392.399254 & 0.000000 & \cr
 2 | 0.01 | & $ A21|D24 $ & 45549 & 17706.407140 & 0.000000 & \cr
 3 | 0.01 | & $ H12|A18 $ & 86025 & 24619.776947 & 0.000000 & \cr
 4 | 0.01 | & $ H12|R17 $ & 48257 & 19028.783592 & 0.000000 & \cr
 5 | 0.01 | & $ I11|R17 $ & 64548 & 27053.952336 & 0.000000 & \cr
 6 | 0.02 | & $ L13|K31 $ & 39382 & 17335.347894 & 0.000000 & \cr
 7 | 0.02 | & $ L13|W19|Q24 $ & 20184 & 379.160544 & 0.000000 & \cr
 8 | 0.02 | & $ M13|W15 $ & 23300 & 6673.177086 & 0.000000 & \cr
 9 | 0.02 | & $ N4|K9 $ & 162152 & 74737.922307 & 0.000000 & \cr
10 | 0.03 | & $ N4|K9|H33 $ & 26376 & 5666.716129 & 0.000000 & \cr
11 | 0.03 | & $ Q17|D24 $ & 86891 & 17162.233105 & 0.000000 & \cr
12 | 0.03 | & $ Q31|H33 $ & 233190 & 186078.818611 & 0.000000 & \cr
13 | 0.03 | & $ R12|Q17 $ & 53740 & 10564.956512 & 0.000000 & \cr
14 | 0.04 | & $ R12|T18 $ & 62774 & 18359.197022 & 0.000000 & \cr
15 | 0.04 | & $ R17|A18 $ & 54366 & 27136.429076 & 0.000000 & \cr
16 | 0.04 | & $ R17|E24 $ & 33748 & 10413.255892 & 0.000000 & \cr
17 | 0.04 | & $ R17|Q31 $ & 45065 & 26805.242087 & 0.000000 & \cr
18 | 0.05 | & $ R17|T21 $ & 70301 & 16232.354294 & 0.000000 & \cr
19 | 0.05 | & $ S10|D24 $ & 57772 & 17415.113746 & 0.000000 & \cr
20 | 0.05 | & $ V11|R12 $ & 39546 & 18975.126308 & 0.000000 & \cr
21 | 0.05 | & $ V11|R12|T18 $ & 17628 & 881.251263 & 0.000000 & \cr
22 | 0.06 | & $ K31|Y33 $ & 36346 & 20803.634880 & 0.000002 & \cr
23 | 0.06 | & $ N4|A21 $ & 45441 & 30227.409858 & 0.000003 & \cr
24 | 0.06 | & $ Q17|K31 $ & 25033 & 10875.740384 & 0.000018 & \cr
25 | 0.06 | & $ G10|H12 $ & 20779 & 7151.794446 & 0.000041 & \cr
26 | 0.07 | & $ K9|A21 $ & 40098 & 27695.038620 & 0.000231 & \cr
27 | 0.07 | & $ F19|D24 $ & 29121 & 16875.538795 & 0.000286 & \cr
28 | 0.07 | & $ Q17|A21 $ & 29621 & 18109.021417 & 0.000737 & \cr
29 | 0.07 | & $ H12|E24 $ & 22348 & 10939.327036 & 0.000839 & \cr
30 | 0.08 | & $ N4|K9|I11 $ & 15175 & 4159.316971 & 0.001355 & \cr
31 | 0.08 | & $ S4|T9|T12|V18|R21 $ & 10919 & 1.718549 & 0.001524 & \cr
32 | 0.08 | & $ N4|K9|A21 $ & 11233 & 623.181959 & 0.002185 & \cr
33 | 0.09 | & $ N4|Q31|H33 $ & 21868 & 11328.342993 & 0.002369 & \cr
34 | 0.09 | & $ F19|A21 $ & 44400 & 34516.144368 & 0.004910 & \cr
35 | 0.09 | & $ K9|Q31|H33 $ & 16593 & 6991.723718 & 0.006625 & \cr
36 | 0.09 | & $ W19|Q24 $ & 16738 & 7234.038664 & 0.007331 & \cr
37 | 0.10 | & $ E1|N12 $ & 10844 & 1492.935945 & 0.008575 & \cr
38 | 0.10 | & $ K9|E24 $ & 13847 & 4587.312260 & 0.009408 & \cr
39 | 0.10 | & $ K9|R17 $ & 33735 & 24568.179150 & 0.010326 & \cr
40 | 0.10 | & $ T12|V18 $ & 23076 & 14893.617567 & 0.026158 & \cr
41 | 0.11 | & $ R12|A21 $ & 15497 & 7516.155896 & 0.031231 & \cr
42 | 0.11 | & $ N4|K9|Q31|H33 $ & 8280 & 493.681367 & 0.036905 & \cr
43 | 0.11 | & $ N4|K9|A18 $ & 11655 & 4250.900600 & 0.050618 & \cr
44 | 0.11 | & $ S4|T9|T12|V18|R21|Y33 $ & 7370 & 0.093039 & 0.052029 & \cr
45 | 0.12 | & $ R12|Q17|T18 $ & 7452 & 240.364918 & 0.058992 & \cr
46 | 0.12 | & $ V11|Q17 $ & 14350 & 7329.962834 & 0.068429 & \cr
47 | 0.12 | & $ H12|T21 $ & 23263 & 16324.923094 & 0.072825 & \cr
48 | 0.12 | & $ Q17|Y33 $ & 17288 & 10374.788061 & 0.074203 & \cr
49 | 0.13 | & $ L13|W19 $ & 15536 & 8921.243955 & 0.092437 & \cr
50 | 0.13 | & $ S17|H28 $ & 6529 & 138.997153 & 0.108375 & \cr
51 | 0.13 | & $ N4|K9|Q31 $ & 10228 & 3894.612095 & 0.112708 & \cr
52 | 0.13 | & $ X8|S17 $ & 6573 & 275.512362 & 0.115524 & \cr
53 | 0.14 | & $ R17|Q31|H33 $ & 7265 & 1223.984346 & 0.137235 & \cr
54 | 0.14 | & $ T9|T12|V18|R21 $ & 6003 & 30.417827 & 0.143515 & \cr
55 | 0.14 | & $ N4|K9|A18|H33 $ & 6380 & 549.756091 & 0.157254 & \cr
56 | 0.14 | & $ S10|F19|D24 $ & 6150 & 620.344848 & 0.189437 & \cr
57 | 0.15 | & $ I11|R17|A18 $ & 6555 & 1027.737537 & 0.189642 & \cr
58 | 0.15 | & $ V11|R12|Q17 $ & 5751 & 247.598509 & 0.192378 & \cr
59 | 0.15 | & $ S4|T9|V18|R21 $ & 5514 & 35.313082 & 0.195240 & \cr
60 | 0.15 | & $ S4|T9|T12|V18|R21|K31 $ & 5462 & 0.090571 & 0.197200 & \cr
61 | 0.16 | & $ H12|R17|A18 $ & 5618 & 172.948903 & 0.199184 & \cr
62 | 0.16 | & $ Q9|T11|L19|-23 $ & 5464 & 38.188997 & 0.201464 & \cr
63 | 0.16 | & $ Y4|Q9|T11|-23 $ & 5364 & 35.276055 & 0.213243 & \cr
64 | 0.16 | & $ N4|A18|Q31|H33 $ & 6378 & 1180.344841 & 0.229871 & \cr
65 | 0.17 | & $ L3|N12|R23 $ & 5114 & 15.794611 & 0.243044 & \cr
```

HIV output: 2/6

```
 66 | 0.17 | & $ V13|V15|I19 $    & 5095  & 4.314940    & 0.244059 & \cr
 67 | 0.17 | & $ R12|Q17|D24 $    & 5088  & 122.811489  & 0.261410 & \cr
 68 | 0.18 | & $ S4|T9|V18 $      & 5671  & 868.949180  & 0.285090 & \cr
 69 | 0.18 | & $ G24|E28 $        & 5363  & 579.114112  & 0.297805 & \cr
 70 | 0.18 | & $ S4|T9|R21 $      & 5425  & 650.238601  & 0.289174 & \cr
 71 | 0.18 | & $ K9|I11|R17 $     & 5315  & 590.615207  & 0.296804 & \cr
 72 | 0.19 | & $ V18|K31|Y33 $    & 5524  & 852.751002  & 0.304979 & \cr
 73 | 0.19 | & $ T21|E24 $        & 19192 & 14557.811161 & 0.310756 & \cr
 74 | 0.19 | & $ S4|T9|T12|V18|R21|K31|Y33 $ & 4390 & 0.004904 & 0.150351 & \cr
 75 | 0.19 | & $ S4|T9|V18|R21|Y33 $ & 4341 & 1.910712 & 0.358927 & \cr
 76 | 0.20 | & $ I11|H12|A18 $    & 5225  & 890.707158  & 0.359740 & \cr
 77 | 0.20 | & $ H12|L13 $        & 9314  & 5009.363342 & 0.364791 & \cr
 78 | 0.20 | & $ N1|S12|F20 $     & 4243  & 17.800459   & 0.378494 & \cr
 79 | 0.20 | & $ Y4|T11|-23 $     & 4876  & 710.489341  & 0.388952 & \cr
 80 | 0.21 | & $ H12|A18|H33 $    & 5292  & 1141.301814 & 0.391569 & \cr
 81 | 0.21 | & $ N12|G24|L25 $    & 4169  & 18.987442   & 0.391690 & \cr
 82 | 0.21 | & $ N12|T13 $        & 5365  & 1255.021021 & 0.398803 & \cr
 83 | 0.21 | & $ N4|K9|G23 $      & 9804  & 5726.074196 & 0.404540 & \cr
 84 | 0.22 | & $ P12|L13|W19|Q24 $ & 4070 & 20.998880  & 0.409748 & \cr
 85 | 0.22 | & $ Q12|Y13|T15|G17|V26 $ & 4024 & 0.000255 & 0.414274 & \cr
 86 | 0.22 | & $ S10|F19|A21 $    & 5598  & 1607.067572 & 0.420292 & \cr
 87 | 0.22 | & $ K9|H12 $         & 26788 & 22912.753561 & 0.441631 & \cr
 88 | 0.23 | & $ S10|Q17|D24 $    & 3960  & 93.803024   & 0.443318 & \cr
 89 | 0.23 | & $ Q17|A21|D24 $    & 3949  & 133.098101  & 0.452738 & \cr
 90 | 0.23 | & $ N4|K9|H12 $      & 4239  & 450.472945  & 0.457896 & \cr
 91 | 0.23 | & $ T9|T12|V18|R21|Y33 $ & 3784 & 1.646276 & 0.459063 & \cr
 92 | 0.24 | & $ Y4|Q9|T11 $      & 4402  & 638.401728  & 0.462612 & \cr
 93 | 0.24 | & $ N4|K9|R17 $      & 4239  & 507.820002  & 0.468770 & \cr
 94 | 0.24 | & $ N4|H12|A18 $     & 4450  & 726.677198  & 0.470266 & \cr
 95 | 0.24 | & $ Q9|T11|L19 $     & 4413  & 691.708041  & 0.470653 & \cr
 96 | 0.25 | & $ S4|T9|T12|R21 $  & 3747  & 31.482325   & 0.471755 & \cr
 97 | 0.25 | & $ N12|S30 $        & 4440  & 766.347625  & 0.479764 & \cr
 98 | 0.25 | & $ I1|S2 $          & 3970  & 345.480880  & 0.489218 & \cr
 99 | 0.26 | & $ S4|T12|V18|R21 $ & 3643  & 32.472859   & 0.491921 & \cr
100 | 0.26 | & $ Q9|T11|-23 $     & 4299  & 742.828036  & 0.502461 & \cr
101 | 0.26 | & $ T21|Q31 $        & 16089 & 12621.469597 & 0.519777 & \cr
102 | 0.26 | & $ K9|A18|Q31|H33 $ & 4160  & 697.063962  & 0.520683 & \cr
103 | 0.27 | & $ S4|T9|R21|Y33 $  & 3460  & 35.030271   & 0.528142 & \cr
104 | 0.27 | & $ Y4|Q9|T11|L19|-23 $ & 3425 & 1.824291  & 0.528495 & \cr
105 | 0.27 | & $ S6|K7|T10|L11|M13|K16|G26|Y28 $ & 3409 & 0.000000 & 0.531288 & \cr
106 | 0.27 | & $ S4|T9|V18|R21|K31 $ & 3406 & 1.860057  & 0.532246 & \cr
107 | 0.28 | & $ S17|I19 $        & 4910  & 1510.151983 & 0.533093 & \cr
108 | 0.28 | & $ Y12|H20|R24 $    & 3401  & 29.556849   & 0.538702 & \cr
109 | 0.28 | & $ S4|T9|V18|R21|K31|Y33 $ & 3370 & 0.100690 & 0.539008 & \cr
110 | 0.28 | & $ S10|Q17 $        & 22065 & 18738.120311 & 0.547525 & \cr
111 | 0.29 | & $ A1|-22|S23 $     & 3303  & 7.355264    & 0.553724 & \cr
112 | 0.29 | & $ M13|W15|E31 $    & 3339  & 56.771417   & 0.556389 & \cr
113 | 0.29 | & $ *24|*25|*26|*27|*28|*29|*30|*31|*32|*33 $ & 3269 & 0.000000 & 0.559020 & \
114 | 0.29 | & $ R17|H33 $        & 11466 & 28229.156188 & 0.565421 & \cr
115 | 0.30 | & $ M13|W15|T18 $    & 3501  & 360.859791  & 0.584679 & \cr
116 | 0.30 | & $ F13|-22|S23 $    & 3323  & 6.681356    & 0.589480 & \cr
117 | 0.30 | & $ R17|A18|T21 $    & 3190  & 89.245042   & 0.592593 & \cr
118 | 0.30 | & $ N4|K9|A18|Q31|H33 $ & 3148 & 55.455693 & 0.594235 & \cr
119 | 0.31 | & $ R17|A18|Q31|H33 $ & 3144  & 101.027645  & 0.604153 & \cr
120 | 0.31 | & $ V1|N23|*24|*25|*26|*27|*28|*29|*30|*31|*32|*33 $ & 3030 & 0.000000 & 0.606
121 | 0.31 | & $ A11|N12 $        & 4517  & 1492.835945 & 0.607916 & \cr
122 | 0.31 | & $ R12|T18|A21 $    & 3150  & 134.485298  & 0.609647 & \cr
123 | 0.32 | & $ S10|G23|D24 $    & 3606  & 599.551395  & 0.611461 & \cr
124 | 0.32 | & $ S1|M13|W15 $     & 3087  & 91.193028   & 0.613590 & \cr
125 | 0.32 | & $ N12|F20|K24 $    & 3202  & 213.735139  & 0.615099 & \cr
126 | 0.32 | & $ M13|W15|E24 $    & 3282  & 306.430052  & 0.617639 & \cr
127 | 0.33 | & $ K9|I11|F19|G23 $ & 4153  & 1180.595212 & 0.618272 & \cr
128 | 0.33 | & $ R2|P3|N5|N6|T7|R8|G14|P15|G16|Y20|T22|Q23|I25|I26|G27|I29|R30|A32 $ & 3353
129 | 0.33 | & $ H12|A18|Q31 $    & 3759  & 845.163446  & 0.629981 & \cr
130 | 0.34 | & $ K17|D20|-23 $    & 2928  & 25.438797   & 0.632234 & \cr
131 | 0.34 | & $ Y5|K7|R10|K23|N24|T28 $ & 2897 & 0.000008 & 0.633345 & \cr
```

HIV output: 3/6

```
132 | 0.34 | & $ G10|R17 $    & 9506 & 6637.164691 & 0.638967 & \cr
133 | 0.34 | & $ Y4|Q9|-23 $    & 3539 & 699.676594 & 0.644852 & \cr
134 | 0.35 | & $ G12|A22|D23|N24 $    & 2838 & 0.092735 & 0.645134 & \cr
135 | 0.35 | & $ T1|R2|P3|N5|N6|T7|R8|G14|P15|G16|Y20|T22|I25|I26|G27|I29|R30|A32 S   & 3787 &
136 | 0.35 | & $ T1|R2|P3|N5|N6|T7|R8|G14|P15|G16|Y20|T22|G23|I25|I26|G27|I29|R30|A32 S   & 3(
137 | 0.35 | & $ N4|H12 $    & 26775 & 23945.157075 & 0.646741 & \cr
138 | 0.36 | & $ V18|*24|*25|*26|*27|*28|*29|*30|*31|*32|*33 $    & 2775 & 0.000000 & 0.657651
139 | 0.36 | & $ A1|R9|-22|S23 $    & 2763 & 0.413224 & 0.660115 & \cr
140 | 0.36 | & $ Y6|Y12|F13|H20|A22|K24 $    & 2761 & 0.000052 & 0.660430 & \cr
141 | 0.36 | & $ V11|A24|S28 $    & 2788 & 31.535138 & 0.661330 & \cr
142 | 0.37 | & $ V20|I22|-24|K25|H29 $    & 2748 & 0.000084 & 0.663009 & \cr
143 | 0.37 | & $ K9|H12|A18 $    & 3267 & 526.343072 & 0.664465 & \cr
144 | 0.37 | & $ T9|T12|V18|R21|K31 $    & 2742 & 1.602621 & 0.664517 & \cr
145 | 0.37 | & $ T8|R9 $    & 3185 & 445.441758 & 0.664683 & \cr
146 | 0.38 | & $ I11|H12|R17 $    & 2909 & 172.776969 & 0.665344 & \cr
147 | 0.38 | & $ Y6|X10|X12|H13|X18|X19|R31 $    & 2736 & 0.000000 & 0.665388 & \cr
148 | 0.38 | & $ A24|S28 $    & 3300 & 566.063943 & 0.665797 & \cr
149 | 0.38 | & $ G12|T18|A22|D23|N24 $    & 2692 & 0.005083 & 0.674094 & \cr
150 | 0.39 | & $ P12|W19|Q24 $    & 3054 & 395.340658 & 0.680669 & \cr
151 | 0.39 | & $ A14|H20|N24 $    & 2697 & 47.434702 & 0.682460 & \cr
152 | 0.39 | & $ T9|T12|V18|R21|K31|Y33 $    & 2632 & 0.086760 & 0.685931 & \cr
153 | 0.39 | & $ R12|Q17|A21 $    & 2701 & 79.045229 & 0.687887 & \cr
154 | 0.40 | & $ R17|A18|H33 $    & 3944 & 1325.820339 & 0.688628 & \cr
155 | 0.40 | & $ W15|I19|A24 $    & 2655 & 56.935384 & 0.692552 & \cr
156 | 0.40 | & $ Q12|R13|V20|I22|K24|-26|H29 $    & 2584 & 0.000000 & 0.695324 & \cr
157 | 0.40 | & $ S1|Y4|-6|N10|Y11|S12|S15|V21|K24 $    & 2554 & 0.000000 & 0.701181 & \cr
158 | 0.41 | & $ T18|A21 $    & 6883 & 4332.151205 & 0.701796 & \cr
159 | 0.41 | & $ K17|D20 $    & 2996 & 458.835571 & 0.704460 & \cr
160 | 0.41 | & $ Q17|D24|K31 $    & 2660 & 125.180912 & 0.704916 & \cr
161 | 0.41 | & $ L13|Q15|W19 $    & 2582 & 98.222466 & 0.714812 & \cr
162 | 0.42 | & $ S4|T9|R21|K31|Y33 $    & 2474 & 1.844223 & 0.717056 & \cr
163 | 0.42 | & $ I1|G4|M11|F18|R22|-24|V25 $    & 2445 & 0.000002 & 0.722286 & \cr
164 | 0.42 | & $ S12|F13 $    & 4939 & 2502.178252 & 0.723857 & \cr
165 | 0.43 | & $ L13|Q17|K31 $    & 2663 & 227.467572 & 0.724104 & \cr
166 | 0.43 | & $ K9|R17|H33 $    & 3142 & 710.504406 & 0.724879 & \cr
167 | 0.43 | & $ P12|L13|W19 $    & 2907 & 483.231131 & 0.726360 & \cr
168 | 0.43 | & $ K9|R17|A18 $    & 3012 & 598.308696 & 0.728290 & \cr
169 | 0.44 | & $ S4|T12|R21 $    & 3010 & 597.264141 & 0.728473 & \cr
170 | 0.44 | & $ N4|I11|R17 $    & 3233 & 820.559839 & 0.728529 & \cr
171 | 0.44 | & $ H13|A24|E31 $    & 2426 & 50.435156 & 0.735563 & \cr
172 | 0.44 | & $ L3|A12|T18|V19|D23|R24 $    & 2374 & 0.000104 & 0.735861 & \cr
173 | 0.45 | & $ K9|A21|H33 $    & 3269 & 897.012220 & 0.737068 & \cr
174 | 0.45 | & $ R2|P3|N5|N6|T7|R8|G14|P15|G16|F19|Y20|T22|G23|I25|I26|G27|I29|R30|A32 S   & 2
175 | 0.45 | & $ R10|K11|S12|V25 $    & 2345 & 0.448221 & 0.741446 & \cr
176 | 0.45 | & $ N4|K9|I11|G23 $    & 2883 & 541.944923 & 0.742108 & \cr
177 | 0.46 | & $ R17|A18|Q31 $    & 3304 & 973.769538 & 0.744153 & \cr
178 | 0.46 | & $ Y4|Q9|T11|F13|Y19|-23 $    & 2321 & 0.009829 & 0.745895 & \cr
179 | 0.46 | & $ I7|F20|Q33 $    & 2355 & 38.678004 & 0.746775 & \cr
180 | 0.46 | & $ T9|V18|K31|Y33 $    & 2352 & 43.522103 & 0.748251 & \cr
181 | 0.47 | & $ L3|A12|V19|D23|R24 $    & 2307 & 0.001890 & 0.748529 & \cr
182 | 0.47 | & $ G4|M11|P18 $    & 2306 & 12.419975 & 0.751048 & \cr
183 | 0.47 | & $ S4|T12|V18|R21|Y33 $    & 2292 & 1.757250 & 0.751673 & \cr
184 | 0.47 | & $ H12|R17|T21 $    & 2417 & 139.651999 & 0.752215 & \cr
185 | 0.48 | & $ R10|S12|W19|Q24 $    & 2299 & 14.238983 & 0.752700 & \cr
186 | 0.48 | & $ D4|E6|I7|L11|Q12|V13|V20|A22|T24|-25|A26|T29|Q33 $    & 2279 & 0.000000 & 0.75
187 | 0.48 | & $ G10|?24 $    & 2727 & 449.008967 & 0.753966 & \cr
188 | 0.48 | & $ V19|R24|V26|L31 $    & 2272 & 0.404088 & 0.755161 & \cr
189 | 0.49 | *  $ V11|R12|Q17|T18 $    & 2281 & 11.909386 & 0.755629 & \cr
190 | 0.49 | & $ L13|W15|Q24|E28 $    & 2270 & 0.994080 & 0.755644 & \cr
191 | 0.49 | & $ T1|R2|P3|N5|N6|T7|R8|G14|P15|G16|F19|Y20|T22|G23|I25|I26|G27|I29|R30|A32 S
192 | 0.49 | & $ R17|T21|E24 $    & 2366 & 123.762808 & 0.760627 & \cr
193 | 0.50 | & $ H13|W15|N28 $    & 2610 & 372.687253 & 0.761541 & \cr
194 | 0.50 | & $ M13|K17|V26 $    & 2455 & 218.504333 & 0.761692 & \cr
195 | 0.50 | & $ M13|Q15|G24 $    & 2335 & 100.386181 & 0.761856 & \cr
196 | 0.51 | & $ F19|G23|D24 $    & 3105 & 885.799386 & 0.764893 & \cr
197 | 0.51 | & $ M11|I15|G18|Q19|T20|F21|H22|A24 $    & 2218 & 0.000000 & 0.765115 & \cr
```

HIV output: 4/6

```
198 | 0.51 | & $ R9|A14|H20|N24 $  & 2214 & 2.664734 & 0.766345 & \cr
199 | 0.51 | & $ S4|T9|V18|K31 $  & 2253 & 45.367685 & 0.767028 & \cr
200 | 0.52 | & $ Y4|T11|L19|-23 $  & 2222 & 36.549243 & 0.771106 & \cr
201 | 0.52 | & $ K9|A18|H33 $  & 9877 & 7701.775158 & 0.772980 & \cr
202 | 0.52 | & $ T9|S18|H20 $  & 2246 & 73.652930 & 0.773506 & \cr
203 | 0.52 | & $ G10|S17|I19 $  & 2252 & 85.140274 & 0.774546 & \cr
204 | 0.53 | & $ T12|F13|A14 $  & 2217 & 52.732117 & 0.774983 & \cr
205 | 0.53 | & $ N4|A21|H33 $  & 1446 & 1316.842768 & 0.781367 & \cr
206 | 0.53 | & $ N9|R10|S12|H20|K23|Q24 $  & 2120 & 0.000164 & 0.783023 & \cr
207 | 0.53 | & $ R12|T18|D24 $  & 2373 & 258.082710 & 0.783941 & \cr
208 | 0.54 | & $ T21|H33 $  & 13722 & 11609.274530 & 0.784336 & \cr
209 | 0.54 | & $ T9|V18|R21 $  & 2733 & 627.501151 & 0.785638 & \cr
210 | 0.54 | & $ L13|K17|V19 $  & 2223 & 123.504647 & 0.786733 & \cr
211 | 0.54 | & $ T9|V18|Y33 $  & 2928 & 837.332414 & 0.788304 & \cr
212 | 0.55 | & $ E1|Q4|I5|D6|I7|Q8|E9|-10|M11|N16|A17|-18|W19|S21|M22|I24|G25|G26|T27|S28|S2
213 | 0.55 | & $ Y5|K7|K23|N24|T28 $  & 2075 & 0.000148 & 0.791109 & \cr
214 | 0.55 | & $ S4|W15|I19|A24 $  & 2071 & 3.211998 & 0.792396 & \cr
215 | 0.55 | & $ N4|K9|A18|Q31 $  & 2414 & 350.433693 & 0.793149 & \cr
216 | 0.56 | & $ X12|L13|N24 $  & 2091 & 32.654961 & 0.794078 & \cr
217 | 0.56 | & $ S8|R10|S12|R20|-23|K24 $  & 2056 & 0.001995 & 0.794496 & \cr
218 | 0.56 | & $ S10|A21|D24 $  & 2195 & 141.715389 & 0.794978 & \cr
219 | 0.56 | & $ T5|K6|K7|I8|H10|G24|M26 $  & 2049 & 0.000000 & 0.795739 & \cr
220 | 0.57 | & $ T9|V18|K31 $  & 2861 & 816.350692 & 0.796510 & \cr
221 | 0.57 | & $ I20|A22|T23|K24 $  & 2040 & 0.135518 & 0.797358 & \cr
222 | 0.57 | & $ Y3|A4|-21|N23 $  & 2039 & 0.001752 & 0.797511 & \cr
223 | 0.57 | & $ G4|W11|D23|G24 $  & 2039 & 0.335758 & 0.797570 & \cr
224 | 0.58 | & $ I11|E24 $  & 4634 & 2601.997572 & 0.798748 & \cr
225 | 0.58 | & $ G10|G17|G24 $  & 2157 & 138.303116 & 0.801095 & \cr
226 | 0.58 | & $ Y6|S8|R10|A15|R16|K22|K24 $  & 2011 & 0.000000 & 0.802448 & \cr
227 | 0.59 | & $ S4|T9|R21|K31 $  & 2043 & 34.105157 & 0.802818 & \cr
228 | 0.59 | & $ D4|E6|I7|R9|L11|Q12|V13|V20|A22|T24|-25|A26|T29|Q33 $  & 1999 & 0.000000 &
229 | 0.59 | & $ Q9|T11|L19|-23|K24 $  & 1990 & 1.569195 & 0.806400 & \cr
230 | 0.59 | & $ S8|P12|X24 $  & 2000 & 16.301963 & 0.807225 & \cr
231 | 0.60 | & $ S4|T9|T12|R21|Y33 $  & 1985 & 1.703737 & 0.807295 & \cr
232 | 0.60 | & $ R10|Y12|V19|Q24|R31 $  & 1982 & 0.043977 & 0.807529 & \cr
233 | 0.60 | & $ T4|Q9|F20|K23|G24 $  & 1979 & 0.004973 & 0.808044 & \cr
234 | 0.60 | & $ L11|S12|L13|V26 $  & 1972 & 4.533048 & 0.810047 & \cr
235 | 0.61 | & $ T5|K6|K7|I8|N9|H10|G24|H26 $  & 1967 & 0.000000 & 0.810128 & \cr
236 | 0.61 | & $ S6|K7|T10|L11|K16|G26|Y28 $  & 1956 & 0.000000 & 0.812033 & \cr
237 | 0.61 | & $ T9|V18|R21|Y33 $  & 1983 & 33.839576 & 0.813076 & \cr
238 | 0.61 | & $ R2|P3|N5|N6|T7|R8|G14|P15|G16|Y20|T22|G23|I25|I26|G27|D28|I29|R30|A32 $  &
239 | 0.62 | & $ F19|A21|D24 $  & 2084 & 139.045764 & 0.813940 & \cr
240 | 0.62 | & $ L1|M13|W15 $  & 1949 & 9.905173 & 0.814948 & \cr
241 | 0.62 | & $ Q9|T11|Q12|L19|F20|K22|T23|R24 $  & 1933 & 0.000000 & 0.815996 & \cr
242 | 0.62 | & $ F19|A21|G23 $  & 4336 & 2404.525279 & 0.816257 & \cr
243 | 0.63 | & $ M13|R17|E24 $  & 2006 & 91.386294 & 0.819143 & \cr
244 | 0.63 | & $ L13|W15|V26 $  & 2149 & 237.129335 & 0.819611 & \cr
245 | 0.63 | & $ N12|W19|-23|N24 $  & 1909 & 7.808759 & 0.821430 & \cr
246 | 0.63 | & $ T1|R2|P3|N5|N6|T7|R8|G14|P15|G16|Y20|T22|I25|G27|I29|R30|A32 $  & 4991 & 30
247 | 0.64 | & $ T21|Q24 $  & 7773 & 5082.829451 & 0.823300 & \cr
248 | 0.64 | & $ G4|V11|R12 $  & 2497 & 698.660368 & 0.823510 & \cr
249 | 0.64 | & $ Q17|K31|Y33 $  & 2149 & 263.756833 & 0.824134 & \cr
250 | 0.64 | & $ M25|K26 $  & 2096 & 217.906699 & 0.825341 & \cr
251 | 0.65 | & $ T21|Q31|H33 $  & 2236 & 361.582066 & 0.825961 & \cr
252 | 0.65 | & $ T12|V18|R21 $  & 2446 & 576.530816 & 0.826794 & \cr
253 | 0.65 | & $ Y4|Q9|T11|L19|-23|N24 $  & 1869 & 0.047981 & 0.826881 & \cr
254 | 0.65 | & $ H12|Q31|H33 $  & 2922 & 1055.147497 & 0.827268 & \cr
255 | 0.66 | & $ R9|M11|I15|G18|Q19|T20|F21|H22|A24 $  & 1865 & 0.000000 & 0.827546 & \cr
256 | 0.66 | & $ V1|T18|N23|*24|*25|*26|*27|*28|*29|*30|*31|*32|*33 $  & 1859 & 0.000000 &
257 | 0.66 | & $ G4|L13|W15|A24 $  & 1866 & 7.095250 & 0.828568 & \cr
258 | 0.66 | & $ P12|T21 $  & 11256 & 9405.119546 & 0.829912 & \cr
259 | 0.67 | & $ T9|K31|Y33 $  & 2669 & 823.122139 & 0.830747 & \cr
260 | 0.67 | & $ K7|A14|A24|V32 $  & 1846 & 0.130705 & 0.831083 & \cr
261 | 0.67 | & $ Q9|T11|I19|L22|T23|K24|V25|V26 $  & 1841 & 0.000000 & 0.931561 & \cr
262 | 0.68 | & $ R9|K17|G24 $  & 2157 & 318.307130 & 0.831945 & \cr
263 | 0.68 | & $ A14|G24 $  & 5018 & 3183.960671 & 0.832719 & \cr
```

HIV output: 5/6

```
264 | 0.68 | & $ S8|R10|S12|V20|A22|R23 $

HIV output: 6/6

```
330 | 0.85 | & $ G8|L13|A14|G18|H20 $ & 1575 & 0.000857 & 0.873716 & \cr
331 | 0.85 | & $ M11|R12|T18 $ & 1784 & 214.819937 & 0.874586 & \cr
332 | 0.86 | & $ Y4|I8|Q9|T11|Y19|I23|S24|V25 $ & 1569 & 0.000000 & 0.874613 & \cr
333 | 0.86 | & $ S4|K7|T9|A14|A24|V32 $ & 1568 & 0.000391 & 0.874763 & \cr
334 | 0.86 | & $ G10|V19|R24|V26|L31 $ & 1567 & 0.022878 & 0.874915 & \cr
335 | 0.86 | & $ A18|T21|H33 $ & 1950 & 386.091755 & 0.875373 & \cr
336 | 0.87 | & $ T9|V18|R21|K31 $ & 1595 & 32.945102 & 0.875649 & \cr
337 | 0.87 | & $ N12|N28|E31 $ & 1644 & 84.308230 & 0.876001 & \cr
338 | 0.87 | & $ N4|K9|F19|G23 $ & 2413 & 853.445657 & 0.876021 & \cr
339 | 0.87 | & $ S15|-21|-22|-23|-24 $ & 1550 & 0.003354 & 0.877439 & \cr
340 | 0.88 | & $ V15|P18|R21|V23|V26 $ & 1543 & 0.000396 & 0.878473 & \cr
341 | 0.88 | & $ V11|R12|A21 $ & 1677 & 139.056915 & 0.879218 & \cr
342 | 0.88 | & $ S4|K31|Y33 $ & 2429 & 891.874986 & 0.879339 & \cr
343 | 0.88 | & $ Y4|Q9|T11|L19 $ & 1566 & 32.897928 & 0.879930 & \cr
344 | 0.89 | & $ A14|S17|W19|F20 $ & 1534 & 1.410979 & 0.880005 & \cr
345 | 0.89 | & $ G4|R9|F20|T26 $ & 1540 & 12.834655 & 0.880800 & \cr
346 | 0.89 | & $ Y6|X10|X12|X18|X19|R31 $ & 1525 & 0.000000 & 0.881117 & \cr
347 | 0.89 | & $ L1|S4|K13|W15 $ & 1525 & 0.559824 & 0.881199 & \cr
348 | 0.90 | & $ N4|K9|A21|H33 $ & 1568 & 48.227041 & 0.881881 & \cr
349 | 0.90 | & $ T9|V11|R22 $ & 1769 & 253.858213 & 0.882556 & \cr
350 | 0.90 | & $ Y6|G8|R10|L11|S12|V20|R23|K24 $ & 1515 & 0.000000 & 0.882576 & \cr
351 | 0.90 | & $ X4|K31 $ & 1926 & 418.267274 & 0.883632 & \cr
352 | 0.91 | & $ P12|D23|N24 $ & 1623 & 115.955006 & 0.883732 & \cr
353 | 0.91 | & $ Q9|K23 $ & 4487 & 2986.952760 & 0.884744 & \cr
354 | 0.91 | & $ G4|R9|M13|W15 $ & 1511 & 14.154263 & 0.885206 & \cr
355 | 0.91 | & $ R2|P3|N5|N6|T7|R8|I13|G14|P15|G16|F19|Y20|T22|G23|I25|I26|G27|I29|R30|A32 $
356 | 0.92 | & $ V13|W15|L19 $ & 1573 & 83.913345 & 0.886323 & \cr
357 | 0.92 | & $ P12|S30 $ & 2786 & 1298.604637 & 0.886566 & \cr
358 | 0.92 | & $ V1|R12|T18|N23|*24|*25|*26|*27|*28|*29|*30|*31|*32|*33 $ & 1487 & 0.000000
359 | 0.93 | & $ Q17|D24|Y33 $ & 1608 & 121.315232 & 0.886698 & \cr
360 | 0.93 | & $ E9|R12|T18 $ & 1614 & 133.600703 & 0.887568 & \cr
361 | 0.93 | & $ G4|R12|T18 $ & 2078 & 597.832556 & 0.887601 & \cr
362 | 0.93 | & $ H4|P12 $ & 2777 & 1298.604637 & 0.887855 & \cr
363 | 0.94 | & $ T1|R2|P3|N5|N6|T7|R8|G14|G16|Y20|T22|G23|I25|I26|G27|I29|R30|A32 $ & 1925 &
364 | 0.94 | & $ S4|T9|N12|V18|R21 $ & 1474 & 1.158001 & 0.888647 & \cr
365 | 0.94 | & $ W19|K24|T26 $ & 1724 & 252.469231 & 0.888834 & \cr
366 | 0.94 | & $ A1|E9 $ & 2089 & 630.489943 & 0.890681 & \cr
367 | 0.95 | & $ A1|G4|F20|A24 $ & 1455 & 2.044033 & 0.891465 & \cr
368 | 0.95 | & $ T9|C12|-22|G24 $ & 1450 & 0.214607 & 0.891912 & \cr
369 | 0.95 | & $ Y4|Q9|T11|Y19|W20|-23|N24 $ & 1447 & 0.000061 & 0.892304 & \cr
370 | 0.95 | & $ G10|M13|A24|E31 $ & 1446 & 2.855158 & 0.892845 & \cr
371 | 0.96 | & $ S10|D24|I26 $ & 2229 & 789.361165 & 0.893336 & \cr
372 | 0.96 | & $ G4|M13|W15 $ & 1691 & 252.133281 & 0.893444 & \cr
373 | 0.96 | & $ N12|E31 $ & 2929 & 1492.835945 & 0.893822 & \cr
374 | 0.96 | & $ T12|F13|A14|N28 $ & 1436 & 2.983773 & 0.894262 & \cr
375 | 0.97 | & $ S4|T12|V18|R21|K31 $ & 1434 & 1.710658 & 0.894363 & \cr
376 | 0.97 | & $ S8|G10|X24 $ & 1444 & 16.637502 & 0.895042 & \cr
377 | 0.97 | & $ Q9|T11|L19|-23|K24|R31 $ & 1427 & 0.051495 & 0.895106 & \cr
378 | 0.97 | & $ M13|S17|N28 $ & 1661 & 239.347729 & 0.895842 & \cr
379 | 0.98 | & $ R10|Y12|V19|E23|Q24 $ & 1420 & 0.021913 & 0.896074 & \cr
380 | 0.98 | & $ R12|I13 $ & 2328 & 908.283714 & 0.896110 & \cr
381 | 0.98 | & $ G10|I20|A22|T23|K24 $ & 1415 & 0.007673 & 0.896763 & \cr
382 | 0.98 | & $ Q9|V18|K23 $ & 1572 & 162.149493 & 0.897472 & \cr
383 | 0.99 | & $ F17|T21|H33 $ & 1486 & 82.159457 & 0.898299 & \cr
384 | 0.99 | & $ T9|S18|K30 $ & 1425 & 25.486414 & 0.898892 & \cr
385 | 0.99 | & $ G8|A14|G18|H20 $ & 1399 & 0.016110 & 0.898964 & \cr
386 | 0.99 | & $ T12|S15|H30|I22|E23|K24 $ & 1393 & 0.000820 & 0.899782 & \cr
387 | 1.00 | & $ I1|Y4|-22|S23|R24 $ & 1393 & 0.040715 & 0.899788 & \cr
```

APPENDIX D

File probsort.pl: 1/1

```perl
$fm = $ARGV[0];

open (IN, $fm);
@prob = <IN>;
chop @prob;
close (IN);

@prob = grep (/cr/, @prob);

open (TEMP, "> probsort.temp");

foreach (@prob)
{
   print TEMP "$_\n";
} close (TEMP);

exit;

$fm = $fm . ".prob";

print "fm: $fm\n";

`sort -o prob.tmp -n01234567890. +9 probsort.temp`;
`rm probsort.temp`;

open (IN, "prob.tmp");
@m2 = <IN>;
chop @m2;
close (IN);

`rm prob.tmp`;

open (TEMP, "> $fm");

$total = scalar @m2;
$i = 0;
foreach (@m2)
{
   printf TEMP "%3d | %.2f | %s\n", $i, ($i / $total), $_;
   $i++;
}
```

APPENDIX E

A[GAP43 RATGAP43]            A[ODC RATODC]              B[nAChRa4 RATNARAA]    0.00000
D[nAChRd RNZCRD1]            D[nAChRe RNACRE]           A[CNTFR S54212]
A[PTN RATHBGAM]              B[FGFR RATFGFR1]           B[TGFR RATTGFBIIR]
D[Ins1 RNINS1]               A[cyclin A RATPCNA]        A[H2AZ RATHIS2AZ]
B[cjun RNRJG9]               A[TCP (I I)]               F[actin RNAC01]
A[CCO1 RATMTCYTOC]           A[CCO2 RATMTCYTOC]         A[SC1 RNU19135]
A[DD63.2 (I I)]

A[GAP43 RATGAP43]            A[GAD65 RATGAD65]          A[GRg2 (#)]            0.00000
B[nAChRa4 RATNARAA]          B[FGFR RATFGFR1]           B[cjun RNRJG9]
A[CCO2 RATMTCYTOC]

A[GAP43 RATGAP43]            F[NFM RATNFM]              A[G67I80/86 RATGAD67]  0.00000
C[mGluR2 RATMGLURB]          B[nAChRa4 RATNARAA]        B[nAChRa5 RATNACHRR]
B[FGFR RATFGFR1]             A[IGF I RATIGFIA]          B[cjun RNRJG9]
B[SOD RNSODR]                A[CCO2 RATMTCYTOC]

B[NMDA2D RNU08260]           D[nAChRe RNACRE]           C[mAChR4 RATACHRMD]    0.00000
B[EGF RATEPGF]               B[TGFR RATTGFBIIR]

B[G67I80/86 RATGAD67]        A[SOD RNSODR]              B[SC7 RNU19141]        0.00000

A[MAP2 RATMAP2]              A[GAP43 RATGAP43]          B[L1 S55536]           0.00000
A[synaptophysin RNSYN]       A[neno RATENONS]           F[GAT1 RATGABAT]
B[ChAT (*)]                  A[ODC RATODC]              B[NOS RRBNOS]
A[GRa2 (I)]                  A[GRa3 RNGABAA]            A[GRa5 (#)]
A[GRb3 RATGARB3]             A[GRg3 RATGABAA]           B[mGluR3 RATMGLURC]
C[mGluR8 MMU17252]           B[NMDA2B RATNMDA2B]        B[nAChRa4 RATNARAA]
D[nAChRa6 RATNARA6S]         D[nAChRd RNZCRD1]          B[5HT1b RAT5HT1BR]
A[trkB RATTRKB1]             A[CNTFR S54212]            A[MK2 MUSMK]
A[PTN RATHBGAM]              B[FGFR RATFGFR1]           D[Ins1 RNINS1]
B[IGF II RATGFI2]            A[IP3R2 RNITPR2R]          A[cyclin A RATPCNA]
A[H2AZ RATHIS2AZ]            B[cjun RNRJG9]             B[Brm (I I)]
A[TCP (I I)]                 F[actin RNAC01]            A[CCO1 RATMTCYTOC]
A[CCO2 RATMTCYTOC]           A[SC1 RNU19135]            D[SC6 RNU19140]
A[DD63.2 (I I)]

D[GFAP RNU03700]             D[GRb2 RATGARB2]           D[NMDA2C RATNMCA2C]    0.00000
A[NT3 RATHDNFNT]             B[CNTF RNCNTF]             D[bFGF RNFGFT]
C[PDGFb RNPDGFBCP]           B[PDGFR RNPDGFRBE]         A[cyclin B RATCYCLNB]
C[cfos RNCFOSR]

F[cellubrevin s63830]        D[G67I86 RATGAD67]         B[IGF I RATIGFIA]      0.00000
B[InsR RATINSAB]

A[GAD67 RATGAD67]            C[mGluR6 RATMGLUR6.]       C[mAChR3 RATACHRMB]    0.00000
B[5HT2 RATSR5HT2]            B[Ins2 RNINS2]

F[cellubrevin s63830]        D[mGluR6 RATMGLUR6.]       D[5HT3 MOUSE5HT3]      0.00000
B[InsR RATINSAB]             A[SC2 RNU19136]

A[nestin RATNESTIN]          B[TH RATTOHA]              C[mAChR4 RATACHRMD]    0.00000
B[CNTF RNCNTF]               B[EGF RATEPGF]

| | | | |
|---|---|---|---|
| A[nestin RATNESTIN]<br>A[MK2 MUSMK] | B[TH RATTOHA]<br>B[IGF II RATGFI2] | C[NGF RNNGFB]<br>B[Brm (I I)] | 0.00000 |
| A[ODC RATODC]<br>C[NGF RNNGFB]<br>A[MK2 MUSMK]<br>D[Ins1 RNINS1]<br>A[H2AZ RATHIS2AZ]<br>F[actin RNAC01]<br>A[DD63.2 (I I)] | D[nAChRd RNZCRD1]<br>D[trk RATTRKPREC]<br>A[PTN RATHBGAM]<br>B[IGF II RATGFI2]<br>B[Brm (I I)]<br>A[CCO1 RATMTCYTOC] | D[nAChRe RNACRE]<br>A[CNTFR S54212]<br>B[TGFR RATTGFBIIR]<br>A[cyclin A RATPCNA]<br>A[TCP (I I)]<br>A[SC1 RNU19135] | 0.00000 |
| A[GAP43 RATGAP43]<br>B[nAChRa4 RATNARAA]<br>B[FGFR RATFGFR1] | F[NFM RATNFM]<br>B[nAChRa5 RATNACHRR]<br>B[cjun RNRJG9] | C[mGluR2 RATMGLURB]<br>B[trkC RATTRKCN3]<br>A[CCO2 RATMTCYTOC] | 0.00000 |
| B[TH RATTOHA]<br>B[Brm (I I)] | A[MK2 MUSMK] | B[IGF II RATGFI2] | 0.00000 |
| D[mGluR1 RATGPCGR]<br>A[EGFR RATEGFR] | D[mGluR4 RATMGLUR4B]<br>A[IGFR1 RATIGFI] | D[nAChRa2 RATNNAR]<br>A[IGFR2 MMU04710] | 0.00000 |
| F[NFL RATNFL]<br>D[nAChRa2 RATNNAR]<br>A[SC2 RNU19136] | D[mGluR4 RATMGLUR4B]<br>D[5HT3 MOUSE5HT3] | D[mGluR6 RATMGLUR6.]<br>A[IGFR1 RATIGFI] | 0.00000 |
| D[MOG RATMOG]<br>D[mGluR4 RATMGLUR4B]<br>A[IGFR2 MMU04710] | B[GRa1 (#)]<br>D[nAChRa2 RATNNAR]<br>C[IP3R3 RATIP3R3X] | D[mGluR1 RATGPCGR]<br>A[EGFR RATEGFR] | 0.00000 |
| A[GAP43 RATGAP43]<br>B[nAChRa5 RATNACHRR]<br>B[cjun RNRJG9] | F[NFM RATNFM]<br>B[FGFR RATFGFR1]<br>A[CCO2 RATMTCYTOC] | B[nAChRa4 RATNARAA]<br>A[IGF I RATIGFIA] | 0.00000 |
| A[cellubrevin s63830]<br>A[CRAF RATRAFA] | A[GRb1 RATGARB1]<br>B[IP3R1 RATI145TR] | A[IGF I RATIGFIA] | 0.00000 |
| B[keratin RNKER19]<br>B[CNTF RNCNTF] | A[cellubrevin s63830]<br>A[IGF I RATIGFIA] | B[TH RATTOHA]<br>A[InsR RATINSAB] | 0.00000 |